(12) United States Patent
Laurence et al.

(10) Patent No.: US 7,599,059 B2
(45) Date of Patent: Oct. 6, 2009

(54) MONITORING MOLECULAR INTERACTIONS USING PHOTON ARRIVAL-TIME INTERVAL DISTRIBUTION ANALYSIS

(75) Inventors: Ted A. Laurence, Livermore, CA (US); Shimon Weiss, Los Angels, CA (US)

(73) Assignee: The Regents of the University of California, Oakland, CA (US)

( * ) Notice: Subject to any disclaimer, the term of this patent is extended or adjusted under 35 U.S.C. 154(b) by 190 days.

(21) Appl. No.: 10/521,632

(22) PCT Filed: Jul. 25, 2003

(86) PCT No.: PCT/US03/23252

§ 371 (c)(1),
(2), (4) Date: Feb. 9, 2006

(87) PCT Pub. No.: WO2004/011903

PCT Pub. Date: Feb. 5, 2004

(65) Prior Publication Data

US 2006/0176479 A1    Aug. 10, 2006

Related U.S. Application Data

(60) Provisional application No. 60/398,955, filed on Jul. 25, 2002.

(51) Int. Cl.
*G01J 3/30* (2006.01)
(52) U.S. Cl. ...................................... 356/317
(58) Field of Classification Search .................. 356/317, 356/318, 417; 250/458.1, 459.1, 461.2
See application file for complete search history.

(56) References Cited

U.S. PATENT DOCUMENTS 6,137,584 A    10/2000 Seidel et al.

(Continued)

FOREIGN PATENT DOCUMENTS

WO    WO 98/57150    12/1998

(Continued)

OTHER PUBLICATIONS

Walhout, A.J.M. and M. Vidal, *Protein interaction maps for model organisms*. Nat. Rev. Mol. Cell. Biol., 2001. 2(1): p. 55-62.

(Continued)

*Primary Examiner*—Gregory J Toatley, Jr.
*Assistant Examiner*—Abdullahi Nur
(74) *Attorney, Agent, or Firm*—Venable LLP; HHenry J. Daley

(57) ABSTRACT

A method for analyzing/monitoring the properties of species that are labeled with fluorophores. A detector is used to detect photons emitted from species that are labeled with one or more fluorophores and located in a confocal detection volume. The arrival time of each of the photons is determined. The interval of time between various photon pairs is then determined to provide photon pair intervals. The number of photons that have arrival times within the photon pair intervals is also determined. The photon pair intervals are then used in combination with the corresponding counts of intervening photons to analyze properties and interactions of the molecules including brightness, concentration, coincidence and transit time. The method can be used for analyzing single photon streams and multiple photon streams.

18 Claims, 13 Drawing Sheets

U.S. PATENT DOCUMENTS

2002/0008211 A1  1/2002  Kask
2003/0096433 A1*  5/2003  Meyer-Almes .............. 436/523

FOREIGN PATENT DOCUMENTS

WO   WO 99/21063   4/1999

OTHER PUBLICATIONS

Mendelsohn, A.R. and R. Brent, *Protein biochemistry—Protein interaction methods—Toward an endgame*. Science, 1999. 284(5422): p. 1948-1950.

Yanagida, M., *Functional proteomics; current achievements*. J. Chromatogr. B Analyt. Technol. Biomed. Life Sci., 2002. 771(1-2): p. 89-106.

Chalmers, M.J. and S.J. Gaskell, *Advances in mass spectrometry for proteome analysis*. Curr. Opin. Biotechnol., 2000. V11(N4): p. 384-390.

De Angelis, D.A., *Why FRET over genomics?* Physiol. Genomics, 1999. 1(2): p. 93-99.

Rigler, R. and E. Elson, *Fluorescence correlation spectroscopy : theory and applications*. 2001, Berlin ; New York: Springer. xx, 487.

Schwille, P., *Fluorescence Correlation Spectroscopy and Its Potential for Intracellular Applications*. Cell Biochemistry and Biophysics, 2001. 34: p. 383-408.

Rarbach, M., et al., *Dual-color fluorescence cross-correlation spectroscopy for monitoring the kinetics of enzyme-catalyzed reactions*. Methods, 2001. 24(2): p. 104-116.

Keller, R.A., et al., *Single Molecule Fluorescence Analysis in Solution*. Appl. Spectrosc., 1996. 50(7): p. A12-A32.

Fries, J.R., et al., *Quantitative identification of different single molecules by selective time-resolved confocal fluorescence spectroscopy*. J. Phys. Chem. A., 1998. 102(33): p. 6601-6613.

Dahan, M., et al., *Ratiometric measurement and identification of single diffusing molecules*. Chem. Phys. (Netherlands), 1999. 247(1): p. 85-106.

Deniz, A.A., et al., *Single-pair fluorescence resonance energy transfer on freely diffusing molecules: observation of Förster distance dependence and subpopulations*. Proc. Natl. Acad. Sci. U.S.A., 1999. 96(7): p. 3670-5.

Elson, E.L. and D. Magde, *Fluorescence correlation spectroscopy. I. Conceptual Basis and Theory*. Biopolymers, 1974. 13(1): p. 1-27.

Ehrenberg, M. and R. Rigler, *Rotational Brownian motion and fluorescence intensity fluctuations*. Chem. Phys. (Netherlands), 1974. 4(3): p. 390-401.

Widengren, J., U. Mets, and R. Rigler, *Fluorescence Correlation Spectroscopy of Triplet States in Solution—a Theoretical and Experimental Study*. J. Phys. Chem., 1995. 99(36): p. 13368-13379.

Widengren, J. and R. Rigler, *Mechanisms of photobleaching investigated by fluorescence correlation spectroscopy*. Bioimaging, 1996. 4(3): p. 149-57.

Magde, D., E. Elson, and W.W. Webb, *Thermodynamic fluctuations in a reacting system: measurement by fluorescence correlation spectroscopy*. Phys. Rev. Lett., 1972. 29(11): p. 705-8.

Magde, D., E.L. Elson, and W.W. Webb, *Fluorescence correlation spectroscopy. II. An experimental realization*. Biopolymers, 1974. 13(1): p. 29-61.

Doi, M. and S.F. Edwards, *The theory of polymer dynamics*. 1988, Oxford Oxfordshire, New York: Clarendon Press, Oxford University Press. xiii, 391.

Qian, H. and E.L. Elson, *On the analysis of high order moments of fluorescence fluctuations*. Biophys. J., 1990. 57(2): p. 375-80.

Qian, H. and E.L. Elson, *Distribution of molecular aggregation by analysis of fluctuation moments*. Proc. Natl. Acad. Sci. U.S.A., 1990. 87(14): p. 5479-83.

Palmer, A.G., III and N. L. Thompson, *Optical spatial intensity profiles for high order autocorrelation in fluorescence spectroscopy*. Appl. Opt., 1989. 28(6): p. 1214-20.

Chen, Y., et al., *The photon counting histogram in fluorescence fluctuation spectroscopy*. Biophys. J., 1999. 77(1): p. 553-67.

Kask, P., et al., *Fluorescence-intensity distribution analysis and its application in biomolecular detection technology*. Proc. Natl. Acad. Sci. U.S.A., 1999. 96(24): p. 13756-61.

Muller, J.D., Y. Chen, and E. Gratton, *Resolving heterogeneity on the single molecular level with the photon-counting histogram*. Biophys. J., 2000. 78(1): p. 474-486.

Chen, Y., et al., *Probing ligand protein binding equilibria with fluorescence fluctuation spectroscopy*. Biophys. J., 2000. 79(2): p. 1074-1084.

Margeat, E., et al., *The human estrogen receptor alpha dimer binds a single SRC-1 coactivator molecule with an affinity dictated by agonist structure*. J. Mol. Biol., 2001. 306(3): p. 433-42.

Van Rompaey, E., et al., *Fluorescence fluctuation analysis for the study of interactions between oligonucleotides and polycationic polymers*. Biol. Chem., 2001. 382(3): p. 379-86.

Scheel, A.A., et al., *Receptor-ligand interactions studied with homogeneous fluorescence-based assays suitable for miniaturized screening*. J. Biomol. Screen., 2001. 6(1): p. 11-18.

Rudiger, M., et al., *Single-molecule detection technologies in miniaturized high throughput screening: Binding assays for G protein-coupled receptors using fluorescence intensity distribution analysis and fluorescence anisotropy*. Journal of Biomolecular Screening, 2001. V6(N1): p. 29-37.

Chen, Y., et al., *Molecular brightness characterization of EGFP in vivo by fluorescence fluctuation spectroscopy*. Biophys. J., 2002. 82(1): p. 133-144.

Palo, K., et al., *Fluorescence intensity multiple distributions analysis: concurrent determination of diffusion times and molecular brightness*. Biophys. J., 2000. 79(6): p. 2858-66.

Schwille, P., F.J. Meyer-Almes, and R. Rigler, *Dual-color fluorescence cross-correlation spectroscopy for multicomponent diffusional analysis in solution* [see comments]. Biophys. J., 1997. 72(4): p. 1878-86.

Heinze, K.G., A. Koltermann, and P. Schwille, *Simultaneous two-photon excitation of distinct labels for dual-color fluorescence crosscorrelation analysis*. Proc. Natl. Acad. Sci. U.S.A., 2000. 97(19): p. 10377-82.

Schwille, P. and K.G. Heinze, *Two-photon fluorescence cross-correlation spectroscopy*. Chemphyschem, 2001. 2(5): p. 269-272.

Deniz, A.A., et al., *Ratiometric single-molecule studies of freely diffusing biomolecules*. Annu. Rev. Phys. Chem., 2001. 52: p. 233-253.

Tellinghuisen, J., et al., *Analysis of Fluorescence Lifetime Data for Single Rhodamine Molecules in Flowing Sample Streams*. Anal. Chem., 1994. 66(1): p. 64-72.

Eggeling, C., et al., *Monitoring conformational dynamics of a single molecule by selective fluorescence spectroscopy*. Proc. Natl. Acad. Sci. U.S.A., 1998. 95(4): p. 1556-61.

Kask, P., et al., *Two-dimensional fluorescence intensity distribution analysis: theory and applications*. Biophys. J., 2000. 78(4): p. 1703-13.

Reynaud, S., *Resonance fluorescence: the dressed atom approach*. Ann. Phys., 1983. 8(4): p. 315-70.

Edman, L. and R. Rigler, *Memory landscapes of single-enzyme molecules*. Proc. Natl. Acad. Sci. U.S.A., 2000. 97(15): p. 8266-71.

Schatzel, K., *New concepts in correlator design*. Inst. Phys. Conf. Ser. No. 77: session 4, 1985. No. 77: session 4: p. 175-185.

Schatzel, K. and R. Peters, *Noise on Multiple-Tau Photon Correlation Data*. SPIE vol. 1430 Photon Correlation Spectroscopy: Multicomponent Systems, 1991. 1430: p. 109-115.

Press, W.H., S. A. Teukolsky, W. T. Vetterling, and B. P. Flannery, *Numerical recipes in C : the art of scientific computing*. 2nd ed. 1992, Cambridge, U.K.: Cambridge University Press. xxvi, 994.

Rigler, R., et al., *Fluorescence Correlation Spectroscopy With High Count Rate and Low Background—Analysis of Translational Diffusion*. Eur. Biophys. J., 1993. 22(3): p. 169-175.

Mets, U., *Antibunching and Rotational Diffusion in FCS*, in *Fluorescence Correlation Spectroscopy*, R. Rigler, and E.S. Elson, Editor. 2001, Springer. p. 346-359.

Creighton, T.E., *Proteins : structures and molecular principles*. 1983, New York: W.H. Freeman. xi, pp. 338-340, 344-346.

Enderlein, J., David L. Robbins, W. Patrick Ambrose, Peter M. Goodwin, and Richard A. Keller, *Statistics of Single-Molecule Detection*. J. Phys. Chem. B, 1997. 101: p. 3626-3632.

Maiti, S., U. Haupts, and W.W. Webb, *Fluorescence correlation spectroscopy: diagnostics for sparse molecules*. Proc. Natl. Acad. Sci. U.S.A., 1997. 94(22): p. 11753-7.

Kubo, R.o., M. Toda, and N. Hashitsume, *Statistical physics II : nonequilibrium statistical mechanics*. 2nd ed. Springer series in solid-state sciences ; 31. 1991, Berlin ; New York: Springer. 279.

Enderlein, J., *Path Integral Approach to Fluorescence Correlation Experiments*. Phys. Lett. A, 1996. 221(6): p. 427-433.

Gardiner, C.W., *Handbook of stochastic methods for physics, chemistry, and the natural sciences*. 2nd ed. 1985, Berlin ; New York: Springer-Verlag. xix, 442.

Mandel, L., *Fluctuations of Photon Beams and their Correlation*. Proc. Phys. Soc., 1958. 72: p. 1037-1048.

Mandel, L., *Fluctuations of Photon Beams: The Distribution of the Photo-Electrons*. Proc. Phys. Soc., 1959. 74(3): p. 233-243.

Sambrook, J. and D.W. Russell, *Molecular cloning : a laboratory manual*. 3rd ed. 2001, Cold Spring Harbor, N.Y.: Cold Spring Harbor Laboratory Press. 3 v.

Mukhopadhyay, J., et al., *Translocation of sigma(70) with RNA polymerase during transcription: fluorescence resonance energy transfer assay for movement relative to DNA*. Cell, 2001. 106(4): p. 453-63.

Murakami, K.S., et al., *Structural basis of transcription initiation: an RNA polymerase holoenzyme-DNA complex*. Science, 2002. 296(5571): p. 1285-90.

Wohland, T., R. Rigler, and H. Vogel, *The standard deviation in fluorescence correlation spectroscopy*. Biophys. J., 2001. 80(6): p. 2987-99.

Richards, B. and E. Wolf, *Electromagnetic diffraction in optical systems. II. Structure of the image field in an aplanatic system*. Proc. Phys. Soc. A, 1959. 253: p. 358-379.

Wolf, E., *Electromagnetic diffraction in optical systems. I. An integral representation of the image field*. Proc. Phys. Soc. A, 1959. 253: p. 349-357.

Cantor, C.R. and P.R. Schimmel, *Biophysical chemistry*. 1980, San Francisco: W. H. Freeman. v. <1 >.

Lide, D.R., *CRC handbook of chemistry and physics*. 3rd electronic ed ed. 2001, Boca Raton, FL: CRC Press.

Efron, B. and R. Tibshirani, *An introduction to the bootstrap*. Monographs on statistics and applied probability ; 57. 1993, New York: Chapman & Hall. xvi, 436.

Eigen, M. and R. Rigler, *Sorting Single Molecules—Application to Diagnostics and Evolutionary Biotechnology*. Proc. Natl. Acad. Sci. U.S.A., 1994. 91(13): p. 5740-5747.

Laurence, T.A., *Photon-counting single-molecule spectroscopy for studying conformational dynamics and macromolecular interactions*, in *Physics*. 2002, University of California: Berkeley, CA. p. 182.

Widengren, J. and P. Schwille, *Characterization of photoinduced isomerization and back-isomerization of the cyanine dye Cy5 by fluorescence correlation spectroscopy*. J. Phys. Chem. A., 2000. 104(27): p. 6416-6428.

Hess, S.T. and W.W. Webb, *Focal volume optics and experimental artifacts in confocal fluorescence correlation spectroscopy*. Biophys. J., 2002. 83(4): p. 2300-17.

Deniz, A.A., et al., *Single-molecule protein folding: diffusion fluorescence resonance energy transfer studies of the denaturation of chymotrypsin inhibitor 2*. Proc. Natl. Acad. Sci. U.S.A., 2000. 97(10): p. 5179-84.

Dittrich, P.S. and P. Schwille, *Photobleaching and stabilization of fluorophores used for single-molecule analysis with one- and two-photon excitation*. Applied Physics B-Lasers and Optics, 2001. 73(8): p. 829-837.

Hebert, T.E. and M. Bouvier, *Structural and functional aspects of G protein-coupled receptor oligomerization*. Biochem. Cell. Biol., 1998. 76(1): p. 1-11.

Bieschke, J., et al., *Ultrasensitive detection of pathological prion protein aggregates by dual-color scanning for intensely fluorescent targets*. Proc. Natl. Acad. Sci. U.S.A., 2000. 97(10): p. 5468-73.

Cohen, F.E., *Protein misfolding and prion diseases*. J. Mol. Biol., 1999. 293(2): p. 313-20.

Prusiner, S.B., *Prions*. Proc. Natl. Acad. Sci. U.S.A., 1998. 95(23): p. 13363-83.

Tjernberg, L.O., et al., *Amyloid beta-peptide polymerization studied using fluorescence correlation spectroscopy*. Chem. Biol., 1999. 6(1): p. 53-62.

Pitschke, M., et al., *Detection of single amyloid beta-protein aggregates in the cerebrospinal fluid of Alzheimer's patients by fluorescence correlation spectroscopy*. Nat. Med., 1998. 4(7): p. 832-4.

Bacia, K., I.V. Majoul, and P. Schwille, *Probing the endocytic pathway in live cells using dual-color fluorescence cross-correlation analysis*. Biophys. J., 2002. 83(2): p. 1184-93.

Abstract, Laurence, et al.—PAID—A New Method to Simultaneously Analyze Brightness . . . Solution Feb. 2001.

\* cited by examiner

MONITORING MOLECULAR INTERACTIONS USING PHOTON ARRIVAL-TIME INTERVAL DISTRIBUTION ANALYSIS

CROSS REFERENCE TO RELATED APPLICATIONS

This application claims priority to U.S. Provisional Application No. 60/398,955, filed Jul. 25, 2002, and to International Application No. PCT/US2003/023252, filed Jul. 25, 2003, the entire contents of which are incorporated herein by reference.

STATEMENT REGARDING FEDERAL FUNDING

This invention was made with U.S. Government support under U.S. Department of Energy Contract No. DE-AC03-76SF00098. The U.S. Government has certain rights in this invention.

BACKGROUND OF THE INVENTION

1. Field of the Invention

The present invention relates generally to fluorescence correlation spectroscopy (FCS). Particularly, the present invention relates to improved data analysis of photon arrival and photon count data typically supplied to FCS analysis by utilizing Photon Arrival time Interval Distribution (PAID) analysis techniques.

2. Description of Related Art

The publications and other reference materials referred to herein to describe the background of the invention and to provide additional detail regarding its practice are hereby incorporated by reference. For convenience, the reference materials are numerically referenced and grouped in the appended bibliography. The contents of these publications and other reference materials are hereby incorporated by reference.

With the availability of the complete sequences of genomes of several organisms, it is critical to determine the biological function of the proteins coded by those genomes. Analysis of protein-protein interactions is important for this process since it can produce protein-protein interaction maps that place each protein in its cellular context, from which it is hoped to infer the protein's function. [1, 2]. Several existing methods that monitor protein-protein interactions are: conventional and modified yeast two-hybrid systems along with reconstitution systems, phage display, fluorescence resonance energy transfer (FRET) methods, mass spectrometry, protein chips, and evanescent wave methods [1-5].

Fluorescence correlation spectroscopy (FCS) and related single-molecule methods are important tools for the in vitro analysis of macromolecular interactions, and are potentially useful for in vivo analysis [6, 7]. FCS-related methods can detect these interactions in a distance-independent fashion, unlike FRET. [8]. FCS-related methods detect macromolecular interactions by monitoring fluorescence fluctuations that result when fluorescent molecules diffuse or flow across a tightly focused laser excitation volume (femtoliter confocal detection volume). At concentrations less than 1 nM, the average molecular occupancy of the detection volume is smaller than one, allowing the detection of photon-bursts generated by single molecules. This is commonly referred to as the "low occupancy" regime. A "photon burst" is the set of all photons detected from a single molecule during its transit through the confocal detection volume. Analysis of these photon-bursts has been used to measure the distribution of molecular properties, such as fluorescence lifetime, polarization anisotropy, and fluorescence resonance energy transfer (FRET) [9-12]. At concentrations between 1 nM-100 nM, the molecular occupancy is still low enough to be sensitive to the addition or subtraction of one molecule within that volume. This is referred to as the "intermediate occupancy" regime. Although it is not possible to separate the photons into bursts from single molecules, the resulting fluctuating fluorescence signal contains dynamic information about several processes such as translational diffusion [13], rotational diffusion [14], intersystem crossing to triplet states [15], and photobleaching [16]. At concentrations greater than 100 nM, many molecules occupy the detection volume and the fluctuations are averaged out. This is known as the "high occupancy" regime. The primary drawback of using FCS-related methods for monitoring macromolecular interactions is the dynamic range over which binding can be detected. These methods are most sensitive in the nM concentration regime, whereas binding constants of protein-protein interactions often correspond to higher concentrations (this limitation is partially offset by the ability of FCS-related methods to detect small subpopulations).

Fluorescence bursts or fluctuations are ideally suited to the study of macromolecular interactions. FIG. 1 shows how the properties of the sample translate into features of the fluorescence signal for a detection volume with low occupancy. Macromolecular interactions such as homo-dimerization and aggregation can be measured using single-channel methods. FIG. 1A depicts a single-channel measurement on a sample containing a mixture of monomers carrying one yellow fluorescent label and tetramers carrying four yellow fluorescent labels in solution. The laser excitation profile (shown in green) and the detection pinhole define the effective detection volume. As these molecules diffuse in and out of the laser excitation profile, bursts of fluorescence photons are detected, shown as an intensity time trace to the right. The three basic characteristics of a single-channel photon burst are: (1) the brightness of the bursts (blue arrows), which is proportional to the number of fluorescence labels detected, (2) the duration of the burst (red arrows), which is related to the diffusion time of the molecule across the laser beam, and (3) the time between bursts of the same species (green arrows) which is inversely proportional to the concentration of that species. The same characteristics apply for the fluctuation analysis used at higher concentrations (intermediate occupancy). In general, the fluorescence signal from an interacting pair of molecules or an aggregate has different characteristics than that from a free single molecule. The complex or aggregate has a larger hydrodynamic radius, which results in a longer diffusion time. It also has more labels than free molecules, which results in increased brightness of the bursts (fluorescence quenching and incomplete labeling are ignored at this stage). To most effectively detect binding or aggregation, a data analysis scheme that measures all these properties at the same needs to be developed.

For interactions between macromolecules of different types (for example hetero-dimerization of two proteins), extending the analysis to two channels improves the sensitivity over one channel analysis [8]. The molecules of one type are labeled with one color (eg. yellow), and the molecules of the other type are labeled with another color (eg. red.) A complex of the two types of molecules has both labels. This is the situation shown to the left of FIG. 1B. Signal from the two fluorophores is separated spectrally onto two detector channels, yellow and red. In addition to the ways described for the single-channel case, the binding of two molecules labeled with the yellow and red fluorophores can be indicated by the detection of simultaneous photon bursts on both channels (orange arrow in FIG. 1B). This coincident detection indicates that both fluorescence labels are present, and thus the two molecules are bound.

Single-channel Data Reduction and Analysis: The task of the data analysis performed on these fluorescence signals is to extract these parameters using all of the information possible, and to present an interpretable graphical representation of the data that summarizes the relevant information in the data set. Several methods summarized below have been developed to perform this task. All of these methods are able to handle vast amounts of data by "reducing" the data to a one- or multi-dimensional histogram, from which the information on the diffusing species is extracted. The trick is to reduce the data, but not too much. As much information as practically possible should be retained to characterize the sample.

Fluorescence Correlation Spectroscopy (FCS): FCS analyzes fluorescence fluctuations through the use of the correlation function [13, 17, 18]. Correlation functions calculated from the intensity signal reveal the time scale and amplitude of various molecular processes, but do not reveal the brightness of each source. In single-channel applications, macromolecular interactions can be detected by monitoring the change in diffusion time resulting from the interaction of two molecules. However, binding often does not produce a large change in diffusion time: for a sphere, doubling the hydrodynamic volume (for instance by binding two equally sized subunits) produces only a 26% increase in diffusion time (since the diffusion time scales with the hydrodynamic radius, which roughly scales as [molecular weight]$^{1/3}$). Therefore, a large change in size is required to measure binding using diffusion constants. A further complication is that the shape of the bound molecules is also important; there is no general relationship between diffusion time and the number of subunits. For example, a short, rod-like dsDNA fragment will diffuse more slowly than a globular protein with the same volume (compare the diffusion constant calculations for a sphere with those for a rod in [19]).

Brightness is a reporter of binding events (ignored by FCS) that can in fact be more sensitive than the diffusion time. If two interacting macromolecules are both labeled, the brightness of the interacting complex is double the brightness of the individual subunits, provided that the quantum yield does not change (which is not always the case.) Brightness has the advantage that the shape of the molecule does not affect it, unlike the diffusion time. Several methods have been developed to use this information.

Moment Analysis of Fluorescence Intensity Distribution (MAFID) and Higher order correlation amplitudes: Moments of the photon counting histogram can be used to monitor occupancy and brightness of labeled macromolecules [20, 21]. By comparing the values of the mean (first order moment), the variance (second order moment), and the third order moment, values for the occupancy and brightness of two species can be extracted. In this way, macromolecular interactions can be monitored by taking advantage of the change in molecular brightness when labeled molecules interact. Another method discussed in [22] uses the amplitudes of higher order correlations to extract the occupancy and brightness, but turns out to be equivalent.

Photon Counting Histogram (PCH) and Fluorescence Intensity Distribution Analysis (FIDA): Rather than calculating the moments of the photon counting histogram as described above, it is possible to fit the histogram directly, thereby using more information to extract brightness and occupancy [23, 24]. In this way, sub-populations with different brightness can be separated [25]. The PCH and FIDA methods differ mainly in their treatment of the shape of the detection volume. PCH has been used to monitor ligand-protein binding equilibria [26], to probe the stoichiometry of protein complexes [27], and to study oligonucleotide-polymer interactions [28]. FIDA has been used to probe receptor-ligand interactions in a format compatible with ultra-high throughput screening [29, 30].

The PCH and FIDA methods contain information about the brightness and occupancy of fluorescent species, but lack the information on dynamics contained in the correlation function. For a sample with a single species, it is possible to perform FCS and PCH or FIDA on the same data set to extract both the brightness and diffusion time [31]. However, if there are multiple species, each with a different diffusion time and brightness, there is no direct way to relate each diffusion time found to its corresponding brightness. A method that simultaneously tracks diffusion time and brightness is necessary to address such heterogeneous samples.

Fluorescence Intensity Multiple Distribution Analysis (FIMDA): By using a series of photon count histograms with multiple time bin widths, it is possible to obtain the same temporal information as FCS while gaining the information on brightness [32, 79]. This is because the shape of the photon count histogram is affected by the fluctuations that occur on the time scale of the time bin width. This method is termed Fluorescence Intensity Multiple Distribution Analysis (FIMDA). Macromolecular interactions can be tracked using FIMDA by monitoring brightness and diffusion time simultaneously.

The type of information that is available from each of the previously described methods is as follows: FCS extracts concentration and diffusion time (and other temporal dynamics), but not brightness; MAFID, PCH, and FIDA extract concentration and brightness, but not diffusion time; and FIMDA extracts concentration, brightness, and diffusion time (and other temporal dynamics).

Multiple-channel Data Reduction and Analysis: Coincident detection of two fluorophores of different colors is a more sensitive indicator of binding events than brightness or diffusion time used in single-channel studies [8]. This is because: (1) coincident bursts are only detected when two molecules are associated, (2) it is less sensitive to quenching of fluorescence, and (3) coincident detection in two channels benefits from the properties of ratiometric measurement. If two interacting molecules are labeled with the same fluorophore, it is necessary to detect distinct subpopulations with a factor of 2 difference in brightness. If they are instead labeled with different-color fluorophores, the experiment is reduced to a simple "yes or no" question. A signal in each channel indicates the presence of the corresponding species. A simultaneous signal in both channels indicates a complex (1:1 ratio between channels), and a signal on only one channel indicates a free molecule (1:0 or 0:1 ratio between channels; random coincidence of signals also needs to be taken into account). The benefit of ratiometric measurement is described in the following. If a fluorescent molecule traverses the same path through the detection volume many times (ignoring triplet-state-induced fluctuations), the number of photons detected from the molecule during those traversals would follow a Poisson distribution, characterized by a mean number of photons (this noise, which is inherent in photon counting experiments, is referred to as "shot noise"). This mean number of photons depends on the path the molecule takes through the detection volume. Taking into account all possible paths through the detection volume, the distribution in photon counts is considerably widened in comparison to shot noise. In contrast, the ratio between the intensity of two channels for an isolated burst is less affected since the mean value of this ratio does not depend on the path taken through the detection volume (the width of the distribution in ratios, however, does depend on the path of the molecule). Measurements using the ratio between two channels (or that consider joint distributions for the two channels) reduce the noise due to differing paths through the detection volume, and are thus more sensitive [11].

Dual-color Cross-correlation FCS: In dual-color cross-correlation FCS, interactions between molecules labeled with two different colors are monitored using the cross-correlation amplitude [8, 33-35]. Significant correlation amplitudes result only when a diffusing species contributes to both channels. By choosing different-color fluorophores that can be separated into different channels with minimal leakage and characterizing the background, it is possible to read the occupancy of bound molecules directly as the amplitude of the cross-correlation. As with single-channel FCS, the diffusion time of the complex can be extracted. The occupancy and diffusion times of the free components can also be extracted by analyzing the autocorrelation of each channel. However, it is necessary to measure using a different method or to assume values for the relative brightness of the different species in order to extract the occupancies and diffusion times.

Ratiometric single-molecule methods [multi-parameter fluorescence detection (MFD), two-dimensional fluorescence intensity distribution analysis (2D-FIDA), single-pair Fluorescence Resonance Energy Transfer (spFRET)]: Photon burst analysis based on ratiometric methods has been developed for monitoring FRET, polarization anisotropy, and spectral fluctuations [11, 36]. If the distance between two labeled molecules is in the 2-8 nm range, FRET can be used to monitor the interaction. For example, single-pair FRET has been used to monitor the cleavage of DNA by a restriction enzyme in solution [12]. The same ratiometric data analysis can also be applied to macromolecular interactions where the separation between fluorophores is greater than the 20-80 Å nm range for FRET, although this has not been done. In this case, it is necessary to excite both fluorophores individually and perform coincidence detection.

Multi-parameter fluorescence detection (MFD) and 2D-FIDA perform tasks similar to the ratiometric single-molecule methods, with additional capabilities. MFD has the additional ability to measure fluorescence lifetime [9, 37, 38], and can also be used to obtain the brightness information available with PCH and FIDA [10]. Originally, the single-molecule measurements with fluorescence lifetime were performed with a single detector, although now they have been extended to multiple channels. 2D-FIDA is the extension of the single-channel FIDA method described above to two channels. In extracting the occupancy and brightness in each channel, it takes advantage of both the ratiometric and brightness information. It can be used for samples in the low and intermediate occupancy regimes [39].

The type of information that is available from each of the previously described multiple-channels method is as follows: Cross-correlation FCS extracts coincidence, concentration and diffusion time (and other temporal dynamics), but not brightness; MFD can detect coincidence and extract brightness and ratiometric information for multiple channels, and diffusion time, however, it can only work with low occupancy samples; and 2D-FIDA can detect coincidence, and extract brightness and ratiometric information for multiple channels. It can work with low and intermediate occupancy samples, but does not extract diffusion time (or other temporal dynamics).

What is lacking in the existing methods is a way to combine the dynamic information available using cross-correlation FCS with the ratiometric and brightness information available with MFD, 2D-FIDA, and ratiometric single-molecule methods, while allowing analysis to be performed at concentrations corresponding to low and intermediate occupancies.

SUMMARY OF THE INVENTION

In accordance with the present invention, a new multi-dimensional data analysis method termed PAID is provided that allows the extraction of information about temporal fluctuations (diffusion), brightness, and coincidence between multiple channels in a unified manner, so that all of the characteristics of each species can be used for identification and for separation from other species. PAID also presents a convenient visual representation of the data that is useful because it focuses on photon-rich regions.

Photon Arrival time Interval Distribution (PAID) is a new method for monitoring both molecular and macromolecular interactions capable of independent and simultaneous determination of coincidence, brightness, diffusion time, and concentration of fluorophore-labeled molecules undergoing diffusion within a confocal detection volume. The method is based on recording the time of arrival of all detected photons, and then forming a multi-dimensional histogram of photon pairs, where one axis is the time interval between two photons and the second axis is the number of other photons detected between that photon pair. PAID is related to cross-correlation Fluorescence Correlation Spectroscopy (FCS) by a projection of this histogram onto the time axis. PAID extends cross-correlation FCS by measuring brightness in addition to diffusion time. Data-fitting analysis based on Monte Carlo simulations of diffusion paths through the detection volume is provided that can be used to simultaneously extract brightness, diffusion time, and concentration from experimental and simulated data. The performance of PAID was compared to other FCS-related methods, such as FIDA, PCH, FIMDA and cross-correlation FCS. The statistical accuracy of the parameters extracted using PAID compares favorably with the FCS-related methods, while providing additional information.

The present invention provides methods for analyzing/monitoring the properties of molecules, including marcromolecule, that are labeled with fluorophores. The method uses a detector to detect a plurality of photons in a photon burst or other photon stream. The arrival time of each of the detected photons is determined. The interval of time between various photon pairs is then determined to provide photon pair intervals. The number of photons that have arrival times within the photon pair intervals is also determined. The photon pair intervals are then used in combination with the corresponding counts of intervening photons to analyze properties and interactions of the molecules including brightness, concentration, coincidence and diffusion. The PAID mathematical model and resulting histograms provide useful ways of depicting the information that is obtained from photon streams when analysis is based on photon-pair time intervals in accordance with the present invention and not fixed time intervals.

The above discussed and many other features and attendant advantages of the present invention will become better understood by reference to the detailed description when taken in conjunction with the accompanying drawings.

BRIEF DESCRIPTION OF THE DRAWINGS

In FIG. 1A left panel, two monomers and a tetramer of a fluorescently-labeled species traverse the laser excitation profile (in green). In FIG. 1A right panel, corresponding fluorescence bursts along with their major properties: width (red arrows; related to the size of species); height or intensity (blue arrows; related to the number of fluorophores on species); and time interval between bursts from identical species (green arrows; related to the occupancy of species). In FIG. 1B left panel, two different molecules (one labeled with a red fluorophore, and the other with a yellow fluorophore) interact to form a complex. In FIG. 1B right panel, free species emit only in one color, complexes emit in both colors. Coincident detection of red and yellow fluorescence (orange arrow) indicates a complex.

FIG. 3A depicts photon streams from 3 channels (start, stop, and monitor). Time axis is shown in discrete clock units. A filled square indicates photon detection at that specific time position. Start photons are identified with different colors, stop photons with different letters, and monitor photons with different numbers. Each photon in the start channel is paired with each stop-channel photon occurring later in time. FIG. 3B depicts a PAID histogram. x-axis, time interval between the start and stop photons; y-axis, number of monitor photons counted in the time interval between the start and stop photons. Example photon pair: the blue start photon is paired with stop photon "d". The time interval between these two photons is 7 clock units, and there are 3 monitor photons (numbers 1, 2, and 3) between them. The corresponding entry into the histogram in B is coded with the blue background and the letter "d".

In FIG. 4A, photons detected in the start, monitor, and stop channels (filled squares) in the time axis (shown with discrete clock units, FIG. 3). The contribution to the PAID histogram for the first start photon, marked with the top black arrow, is shown in FIG. 4B. The time interval bins are shown as gray and white bands between the start channel and the monitor channel. The bins are log-spaced, with 2, 4, 8, 16, . . . clock units. The monitor photon count bins are shown as gray and white bands between the monitor channel and the stop channel. These bins are also log-spaced, with 1, 2, 4, 8, . . . photon counts. The gray and white bands below the stop photon channel show how the time interval and monitor photon count bins combine to form the two-dimensional histogram bins. Each bin is labeled with the number of stop photons counted within the bin, subsequently transferred to the histogram in FIG. 4B.

FIGS. 6B-F illustrate how changes in the parameters of the diffusing species, the background count rate, and the sample composition affect the PAID histogram. Arrows indicate changes in features (see text for details). In FIG. 6B, the occupancy is increased 10-fold, $c'_1=10\times c_1$. In FIG. 6C, the brightness per molecule is increased 10-fold, $q'_{11}=10\times q_{11}$. In FIG. 6D, the diffusion time of the molecule is increased 10-fold, $\tau'^D_1=10\times\tau_1^D$. In FIG. 6E, a background component is added, $k'_{01}=5$ kHz. In FIG. 6F, a species with 4 times the brightness is introduced, $q_{21}=200$ kHz, along with a background $k'_{01}=0.8$ kHz (values chosen so that autocorrelations corresponding to FIG. 6A and FIG. 6F overlap). In FIG. 6G, autocorrelations, corresponding to the collapse of the PAID histograms in FIGS. 6A-F onto the time interval axis, are shown for comparison with FCS.

In FIG. 7A, the PAID histogram for the simulation is depicted (parameters as in FIG. 6A). FIG. 7B shows the fitted PAID histogram. FIG. 7C shows horizontal slices of PAID histograms. FIG. 7D shows vertical slices of PAID histograms. Slices of the simulation, black; slices of the fit, red.

FIGS. 8A, D, G, and J, are PAID histograms RYR, RRR, RRY, and YYR of a mixture containing $A^y$ ($c_1=0.05$, $\tau_1^D=300$ µs, $q_{1R}=5$ kHz, and $q_{1Y}=45$ kHz), $B^r$ ($c_2=0.05$, $\tau_2^D=300$ µs, $q_{2R}=50$ kHz, and $q_{2Y}=0$ kHz), and $A^yB^r$ ($c_3=0.05$, $\tau_3^D=400$ µs, $q_{3R}=55$ kHz, and $q_{3Y}=45$ kHz). The background in each channel was $k_{0R}=k_{0Y}=2$ kHz. In FIGS. 8B, E, H, and K, the mixture does not contain the complex ($A^yB^r$) present in FIGS. 8A, D, G, and J. The effect of the absence of $A^yB^r$ is seen by comparing FIG. 8A with FIG. 8B; FIG. 8D with FIG. 8E; FIG. 8G with FIG. 8H; and FIG. 8J with FIG. 8K. Differences are pointed to by arrows and discussed in the Detailed Description of the Invention. Vertical slices from the PAID histograms at time interval $\tau=1$ ms are shown in FIGS. 8C, F, I, and L, showing the difference between the histograms with and without $A^yB^r$.

FIG. 9A shows that a two-monitor channel PAID histogram is three-dimensional, so three two-dimensional slices at $\tau=100$ µs, τ=1 ms, and τ=10 ms are shown for each histogram. In FIG. 9A, both free species and complex are present. In the τ=1 ms slice, a cartoon of each diffusing species is placed next to the contribution from that species. In FIG. 9B, the complex is absent.

FIGS. 10B, E, H, and K, are PAID histograms of a $DNA^{Cy5,1T}$ and $DNA^{Cy3,65B}$ mixture. Differences in the histograms (due to the absence of $DNA^{Cy5,1T/Cy3,65B}$) are pointed to by arrows. Due to the inactive component of Cy5, the occupancy of the dual-labeled species is significantly lower than the other species, lowering the peaks corresponding to the dual-labeled species (cf. FIG. 8).

FIG. 11A is the PAID histogram for the data. FIG. 11B is the fit to PAID histogram (1 of 8 histograms fitted simultaneously). Horizontal slices of both are shown in FIG. 11C, and vertical slices are shown in FIG. 11D. The slices of the simulation are shown in black with error bars, and the slices of the fit are shown in red.

DETAILED DESCRIPTION OF THE INVENTION

Figure 1:
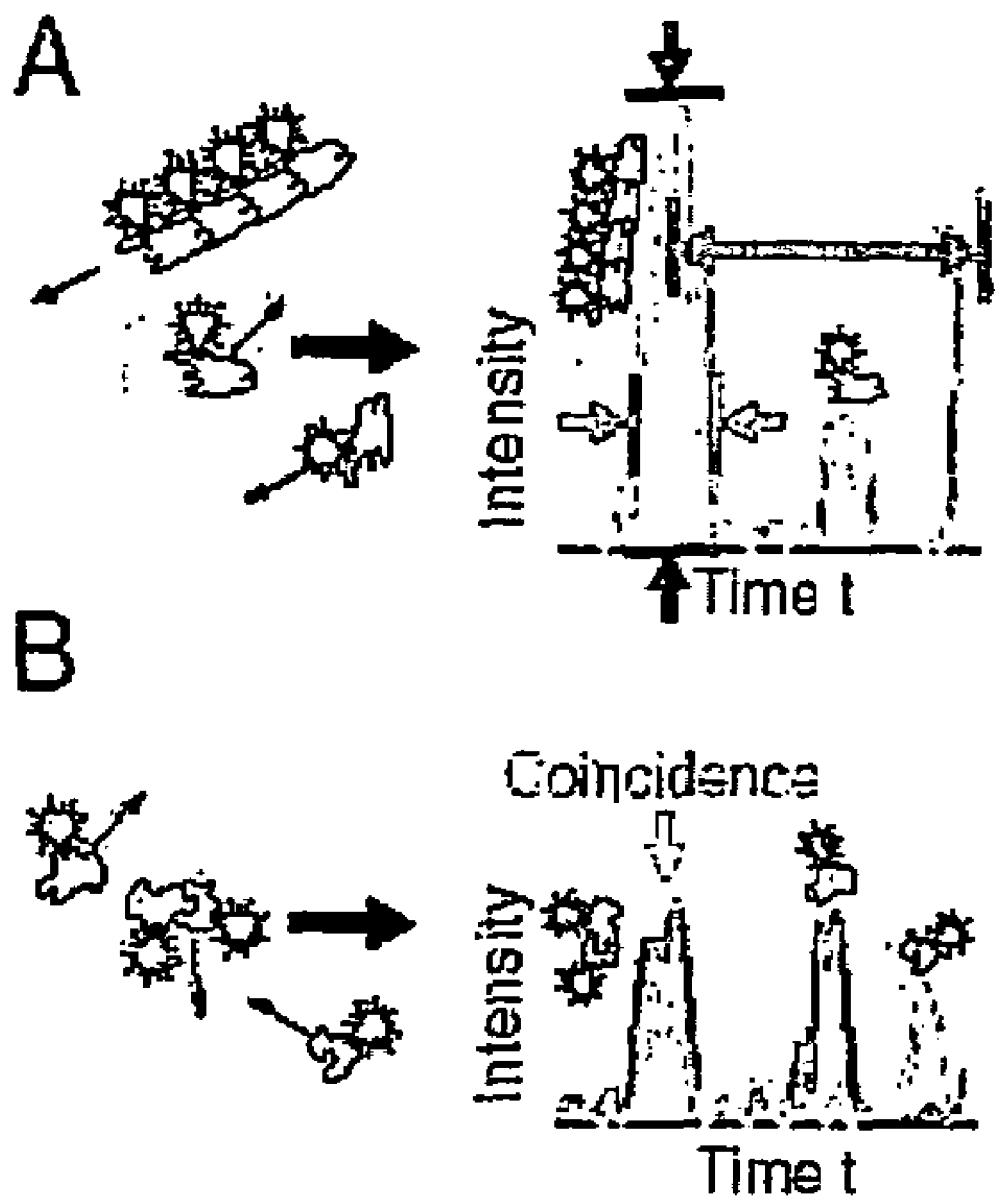
FIG. 1 is a diagrammatic representation of the detection of macromolecular interactions using fluorescence fluctuation signals.

PAID in accordance with the present invention is based on the discrete format of single photon-timing data (FIG. 2), which treats signals as photons streams, rather than analog signals. Using a dual-channel microscope with avalanche photodiode detectors (APDs), streams of electronic pulses corresponding to single photons are generated, and the arrival time of each pulse is recorded, resulting in streams of photon-arrival times, where $t_{Ai}$ is the arrival time of the $i^{th}$ photon from APD-channel A. The photon stream is represented as a sum of Dirac delta functions (which allow representation of discrete events over the continuous variable (t):

$$I_A(t) = \sum_{i=1}^{N_A} \delta(t - t_{Ai}). \tag{1}$$

where $N_A$ is the total number of photons detected in channel A; the number of photons arriving between times $t_{min}$ and $t_{max}$ is $$n = \int_{t_{min}}^{t_{max}} dt I_A(t).$$

All sources of uncertainty in specifying arrival times are shorter than the >1 μs timescale studied here (uncertainty arises from the Heisenberg uncertainty principle (λ/c~2 fs), the APD response time (300-500 ps), and the resolution of the digital clock (Δt=12.5 ns for NI 6602 counting board that times electronic pulses)). The arrival time $t_{Ai}$ of each photon is recorded as an integer $t_{Ai}t$ with $t_{Ai}=[t_{Ai}/\Delta t]$, (brackets indicate the greatest integer function, e.g. [3.14]=3). The arrival time is recovered with accuracy Δt by multiplication with the recorded integer: $t_{Ai} \approx t_{Ai}\Delta t$. For duration T, $t_{Ai}t$ will be in the range 0,1, . . . ,T, where T=[T /Δt], converting Eq. (1) to:

$$I_A(t) = \sum_{i=1}^{N_A} \delta(t, t_{Ai}). \tag{2}$$

δ is the Kronecker delta function: $\delta(t,t_{Ai})=1$ if $t=t_{Ai}$, and $\delta(t,t_{Ai})=0$ if $t \neq t_{Ai}$. In the following, it is assumed that the time scales of interest are much greater than the time resolution Δt, so most of the expressions are written with the discrete time variable t.

In FCS and FCCS, the relationship between a photon stream at one time $I_S(t)$ and a second photon stream at a later time $I_T(t+\tau)$ as a function of the time interval τ is measured using the cross-correlation (auto-correlation is a specialization of this function), $$C_{ST}(\tau) = \langle I_S(t)I_T(t+\tau)\rangle/\langle I_S(t)\rangle\langle I_T(t)\rangle \tag{3}$$

Assuming a stationary stochastic process, the ensemble averages denoted by the angle brackets can be evaluated as time averages:

$$\langle \ldots \rangle \to \lim_{T \to \infty} \frac{1}{T} \sum_{t=0}^{T} (\ldots).$$

By switching to temporal averaging over a finite experiment of duration T, Eq. (3) is converted into the following histogram used to estimate the cross-correlation (the hat denotes an estimator), $$\hat{C}_{ST}(\tau) = T \sum_{i=1}^{N_S} \sum_{j=1}^{N_T} \delta(\tau, t_{Tj} - t_{Si})/N_S N_T \tag{4}$$

The cross-correlation histogram is formed by comparing the arrival times of each pair of photons $t_{Si}$ and $t_{Tj}$, and adding 1 to a histogram at the bin corresponding to the interval $\tau=t_{Tj}-t_{Si}$. The cross-correlation histogram can be viewed as a distribution of time intervals between photon arrivals (since swapping the roles of $I_S$ and $I_T$ is equivalent to changing the sign of $\tau$, we can specify $\tau \geq 0$ without loss of generality). $I_S$ and $I_T$ are defined as the "start" and "stop" photon streams respectively; all quantities associated with the start and stop photon streams are labeled with the subscripts S and T, respectively. While $I_S(t)$ and $I_T(t)$ are kept formally distinct, the same photon stream can be assigned to both so that $I_S(t)=I_T(t)$. In this case, Eq. (4) becomes an autocorrelation.

To include the brightness information lacking in the cross-correlation, PAID adds a new photon-counting dimension n to the cross-correlation histogram of FCS, showing the contribution of each species to the cross-correlation amplitude. The number of photons $n_M$ that arrive between times $t_{Si}$ and $t_{Tj}$ are counted (Eq. (4)) in an additional photon stream $I_M(t)$ (the "monitor" photon stream), with photon arrival times $t_{Mk}$:

$$n_M(t_{Si}, t_{Tj}) \equiv \sum_{t=t_{Si}+1}^{t_{Tj}-1} I_M(t). \quad (5)$$

It should be noted that $I_M(t)$ is formally distinct from $I_S$ and $I_T$, but can be set to be identical to one or both. By counting photons in each time interval as well as measuring its duration, the cross-correlation estimate is spread over the photon-counting dimension n, providing an additional history of the interval between the detection of the start and stop photons. In terms of ensemble averages, the PAID function is $$C_{STM}(\tau,n)=\langle I_S(t)I_T(t)\delta[n,n_M(t,t+\tau)]\rangle/\langle I_S(t)\rangle\langle I_T(t)\rangle \quad (6)$$

This function can be graphed in two dimensions (n and $\tau$), where the additional n axis slices the cross-correlation into strips with different numbers of counted monitor photons along the vertical axis. Rather than a photon count probability distribution (the photon counting histogram of PCH/FIDA), the PAID function acts as a photon-count distribution of correlations. For an experiment of duration T, Eq. (6) can be estimated by a digital double summation histogram, $$\hat{C}_{STM}(\tau, n) = T \sum_{i=1}^{N_S} \sum_{j=1}^{N_T} \delta(\tau, t_{Tj} - t_{Si})\delta[n, n_M(t_{Si}, t_{Tj})] / N_S N_T \quad (7)$$

Figure 3:
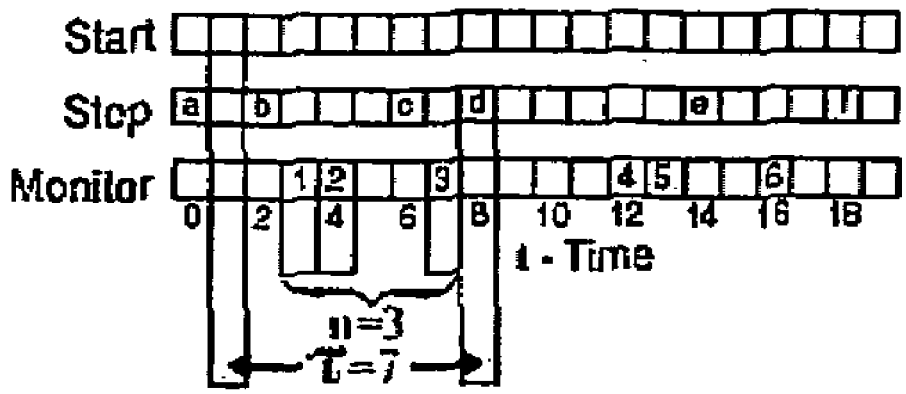
FIG. 3 shows how a PAID histogram in accordance with the present invention is generated.
Figure 3:
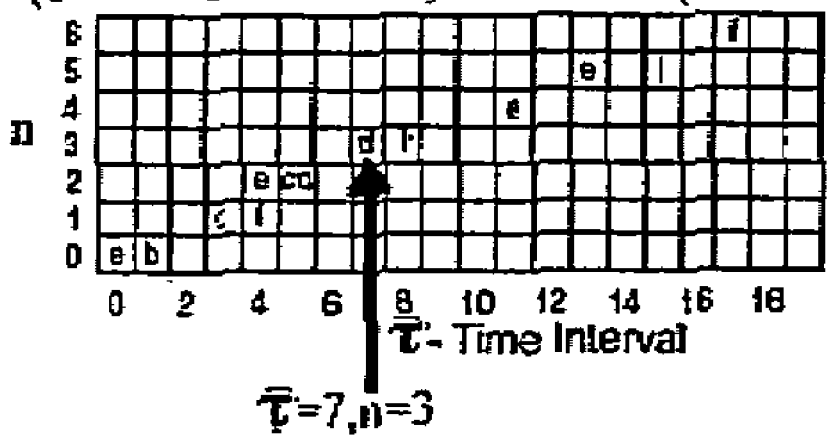

The PAID histogram $C_{STM}(\tau,n)$ describes the distribution of count rate in the stop channel over the number n of intervening photons in the monitor channel within a time interval $\tau$ since receiving a start photon. For each pair of photons $t_{Si}$ and $t_{Tj}$, an event is placed in a 2D histogram, where one axis is the time interval $\tau=t_{Tj}-t_{Si}$, and the other axis is the number of monitor photons counted $n=n_{Mj}$. FIG. 3 shows how a PAID histogram is formed from the start, stop, and monitor photon streams using Eq. (7). To capture a wide dynamic range, log or quasi-log axes are used for the histograms. By summing over n and comparing to Eq. (4), the following is obtained:

$$\hat{C}_{ST}(\tau) = \sum_{n=0}^{\infty} \hat{C}_{STM}(\tau, n) \quad (8)$$

showing that the cross-correlation histogram is the collapse of $\hat{C}_{STM}(\tau,n)$ onto the time interval $\tau$ axis.

For a single-channel experiment, a single channel constitutes the start, stop, and monitor channels, [S=T=M]; the number of photons counted between each pair of photons is n=j−i−1 for the start photon indexed by i, and the stop photon indexed by j. This special case of the PAID histogram is written for a finite experiment of duration T, $$\hat{C}_{SSS}(\tau, n) = T \sum_{i=1}^{N_S} \sum_{j=1}^{N_S} \delta(\tau, t_{Sj} - t_{Si})\delta(n, j-i-1)/N_S^2 \quad (9)$$

This PAID histogram is the series of waiting-time distributions to the $n^{th}$ photon (useful concept for autocorrelations that cannot be extended to cross-correlations); similar constructions with a single value of n were used as criteria in sifting for bursts [10]. By applying Eq. (8) to the single-channel result in Eq. (9), the result is recovered that summing the series of waiting-time distributions to the nt photon gives the autocorrelation function [40].

Equation (7) is extended to include higher order temporal correlations, or more monitor photon streams, by adding factors of the form $\delta(\tau_2,t_{T_{2j}}-t_{S_{2i}})$ for temporal correlations, and factors of the form $\delta(n_2,n_{M_{2ij}})$ for additional monitor photon streams ($S_2$, $T_2$, and $M_2$: additional formal photon streams; $n_2$ and $\tau_2$: additional photon counting and time interval variables). Higher-order temporal correlations are useful for monitoring non-Markovian dynamics [41], and multiple monitor photon count axes in a single histogram can take advantage of ratiometric measurements for better separation of species.

Bin Specification and Normalization for PAID Histogram:

When forming a PAID histogram for the large number of photons obtained in fluorescence fluctuation experiments, it is more meaningful to place events in bins than to make a scatter plot. In choosing the size and spacing of bins, one needs to consider that fluorescence fluctuations occur over a large range of time scales. To cover a large range of time scales with a minimum number of histogram bins, log or quasi-log time bins are commonly used in FCS. For the PAID histogram, one chooses the bins for the time interval $\tau$ axis to be log-spaced, with 10 bins per decade. To use a log scale for the monitor photon axis is more problematic (especially at low photon counts) since the number of monitor photons that arrive is strictly an integer. The clock time resolution $\Delta t$ can be chosen to be small enough to make the integer nature of the discrete time interval variable $\tau=[\tau/\Delta t]$ negligible in the 1s regime, but this cannot be done with the number of monitor photons counted. Unless one is willing to use a spacing of bins that is extremely sparse (factors of 2,3,4 . . . ), the discrete spacing of the number of monitor photons will cause log bins to be inconsistently occupied at low n; some bins may not even have an integer in them. So, a quasi-log scale is used that is adapted from the multiple tau correlation technique [42, 43]. The first 16 bins are evenly spaced with increments of 1, $(n_1, \ldots, n_{16})=(0,1, \ldots, 15)$; then, with each set of 8 bins, the increment is doubled (different increments may be used). The next 8 bins are $(n_{17}, \ldots, n_{24}) = (16\text{-}17, 18\text{-}19, \ldots, 30\text{-}31)$ with an increment of 2, followed by $(n_{25}, \ldots, n_{32}) = (32\text{-}35, 36\text{-}39, \ldots, 60\text{-}63)$ with an increment of 4, etc. On the large scale these bins are log-spaced, while on the small scale they are linearly spaced. In this way, a large dynamic range of integers can be covered in a consistent manner with a small number of bins. After placing events in the histogram bins, normalization is necessary to obtain $C_{STM}(\tau,n)$. First, the histogram is multiplied by $T/N_S N_T$ in Eq. (7). Second, for a bin that has time interval axis limits $\tau_{low}$ and $\tau_{high}$ and monitor photon axis limits that include the integers $n_{low}$ through $n_{high}$, one divides by the size of the bin $(\tau_{high} - \tau_{low})(n_{high} - n_{low} + 1)$. The value for the bin is an average of $C_{STM}(\tau,n)$ over the bin limits, rather than an integral over the bin limits. This normalizes the histogram, providing $C_{STM}(\tau,n)$, a non-ideal representation for a log scale: when plotting a slice of the histogram in the log scale of the monitor photon count axis, for a constant time interval, it is desirable that the actual area under the curve correspond to the value of the correlation $C_{ST}(\tau)$. To do this, one approximates the photon monitor variable n as a continuous variable n, then converts to a log scale using the expression $\zeta = \log_{10} n$. The relation in Eq. (8) is kept valid in the new variable. The sums over n are approximated as integrals over a continuous variable n, and converted to the log variable $\zeta$:

$$C_{ST}(\tau) = \sum_{n=0}^{\infty} C_{STM}(\tau, n) \qquad (10)$$
$$= \int_0^{\infty} dn C_{STM}(\tau, [n])$$
$$= \int_{-\infty}^{\infty} d\zeta (n \ln 10) C_{STM}(\tau, [n])$$
$$\equiv \int_{-\infty}^{\infty} d\zeta C'_{STM}(\tau, \zeta)$$

By looking at the differentials, one finds that by changing variables from n to $\zeta$ the amplitude of the PAID histogram is changed by a factor $(\ln 10)n$. So, the histogram bins are in addition weighted by a factor of $(n+0.5)\ln 10$. We add 0.5 because we consider each bin in n as covering a range between n and n+1, and the average over this range is n+0.5. This only makes a difference at low n, and causes the n=0 bin to be weighted by the factor 0.5 rather than 0. It should be emphasized that this rescaling is made to improve the visual display of the histogram, and in no way affects the statistical characteristics of the histogram.

Figure 4:
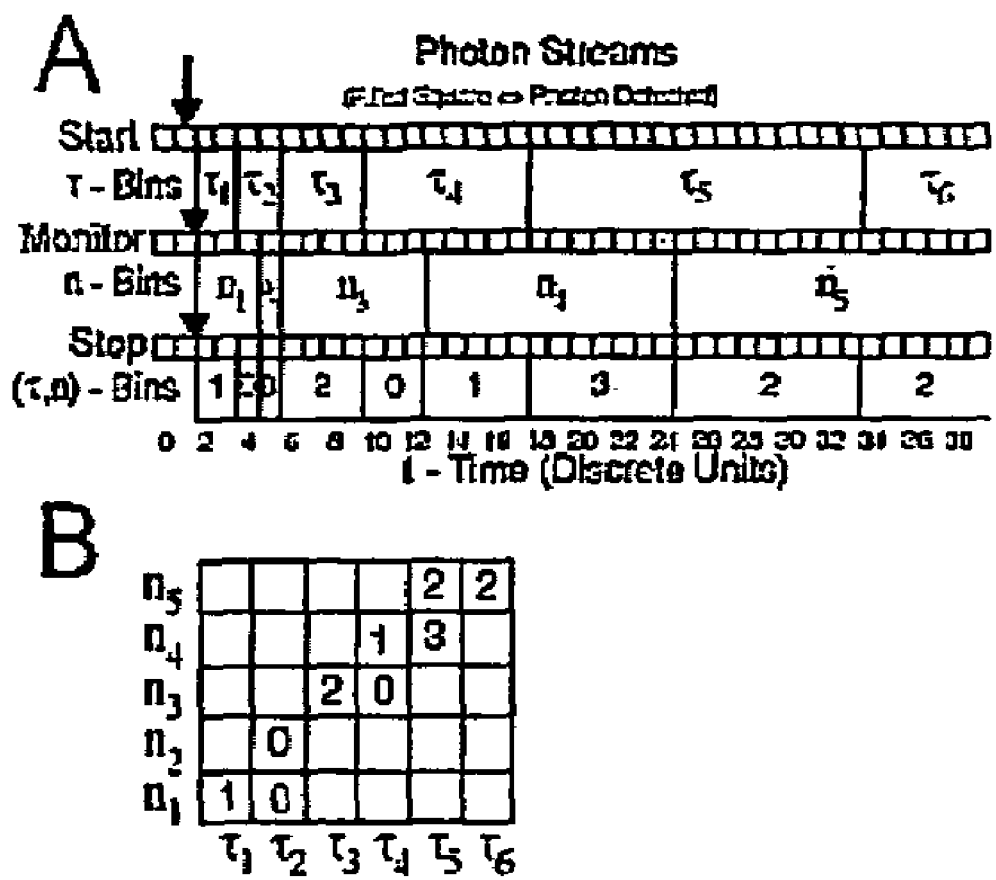
FIG. 4 depicts the generation of 2D-PAID histograms with log time-interval axis and log or quasi-log monitor photon count axis.

Efficient Algorithms for Constructing PAID Histograms:

A direct algorithm to form PAID histograms from photon streams compares each photon from the start channel with each photon in the stop channel, then calculates the number of monitor photons that fall between each start and stop photon. If there are $N_S$ photons in the start channel, and $N_T$ photons in the stop channel, there are $N_S N_T$ entries into the histogram, making the algorithm $O(N^2)$, and limiting the dynamic range of the PAID histogram. A more efficient algorithm exploits the log spacing of the time interval bins $\tau_a$ and the quasi-log spacing of the monitor photon count bins $n_b$ (FIG. 4A; filled square placed at the integer-valued time of arrival of each detected photon, $t_i^S$; time interval and monitor photon count bins corresponding to the first start photon are denoted by the arrow at the top). The time interval bins, log-spaced with integer time intervals 2,4,8,16, . . . are shown below the S photon stream. The monitor photon count bins, log-spaced with monitor photon counts 1,2,4, . . . are shown below the M photon stream. The time interval and monitor photon count bins, combined to form the 2D-histogram bins, are shown below S. The number of stop photon inside each bin is shown. These values are transferred to the 2D-histogram in FIG. 4B. The algorithm: (1) consider each start photon arrival time $t_i^S$, and search for photons in T and M that are closest to this time; (2) set the current time interval ($\tau$) bin to $a_{curr}=1$, and the current monitor photon count (n) bin to $b_{curr}=1$; (3) calculate the time interval $\tau_M$ at which M switches to the next monitor count bin $b_{curr}+1$; (4) if $\tau_M$ is less than the time interval of the $(a_{curr}+1)^{th}$ $\tau$ bin, perform a binary search on T to find the photon arriving just after $\tau_M$, to determine how many stop photons arrive in the current bin and add them to the $(a_{curr}, b_{curr})$ bin of the histogram; advance $b_{curr}=b_{curr}+1$, and go to step 3; (5) otherwise, perform a binary search on T to find how many stop photons arrive up to the time of the $(a_{curr}+1)^{th}$ $\tau$ bin, and add them to the $(a_{curr}, b_{curr})$ bin of the histogram and advance $a_{curr}=a_{curr}+1$; go to step 3, till there are no more stop photons or $(a_{curr}, b_{curr})$ is outside of the histogram; (6) go to step 1 till there are no more start photons.

This algorithm uses the fact that the start, stop, and monitor channels are ordered lists (each successive photon is at a later time) by performing binary searches. A modified search algorithm that uses increments of increasing size from the initial search index to bracket the desired value before performing a standard binary search was found to be most effective (see description of hunt in [44].) Also, because of the log spacing on both axes, a small number of binary searches can cover a large dynamic range. The algorithm is extendable to multiple monitor channels. On a 1.2 GHz Pentium 3 based PC, the algorithm shown here is able to form the PAID histogram of a 10 sec data set with 3,750,000 photons in 2 minutes and the PAID histogram of a 30 sec data set with 150,000 photons in 4.4 seconds, scaling nearly linearly with the number of photons in the data set.

Figure 2:
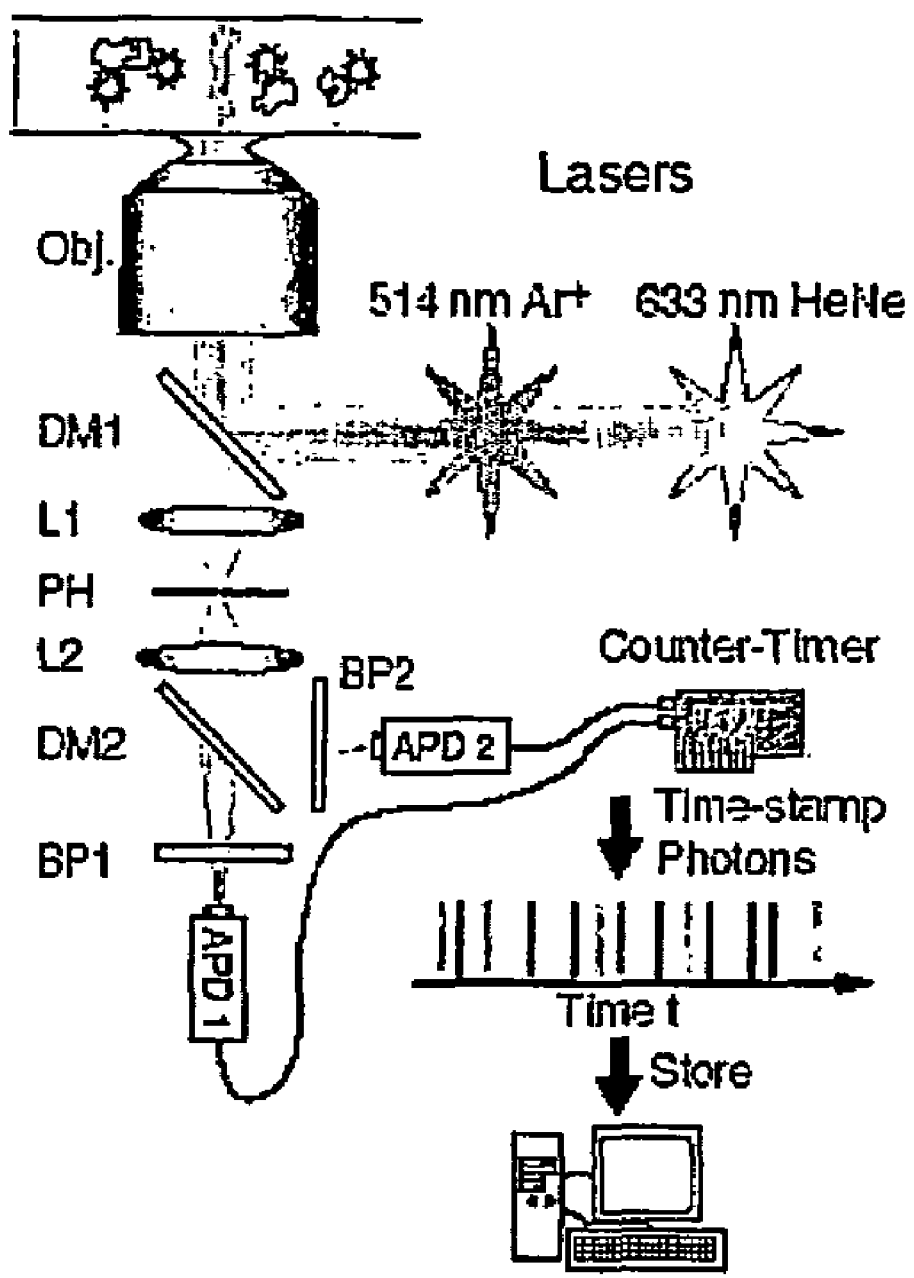
FIG. 2 is a schematic representation of exemplary instrumentation that is used for two-color cross-correlation measurements. Two laser sources (514 and 633 nm) are introduced into an inverted microscope; reflected by a dichroic mirror (DM1), and focused into a sample cell assembled using two glass coverslips separated by a 1 mm-thick silicone gasket by a 1.3 NA oil-immersion objective. Fluorescence from the sample is collected through the objective, transmitted through DM1, and focused onto a pinhole (PH) by the microscope tube lens (L1). After a second lens (L2), the fluorescence is split by a dichroic mirror (DM2) into red and yellow channels. Red and yellow fluorescence pass through bandpass filters (BP1 and BP2, respectively), and are detected using APD1 and APD2, respectively. The APDs emit an electronic pulse for every photon detected, and the pulses are time-stamped using a counter-timer board and stored in a PC (the timed photons are represented in the figure as bars where the color of the bar represents whether the red or yellow channel detected the photon).

Application of PAID to Fluorescent Species Diffusing in Solution:

Fluorescent molecules diffusing in solution are excited and detected using a single-molecule epi-fluorescence confocal microscope (FIG. 2). The fluorescence signal is split into spectral regions matching the emission spectra of the fluorophores. For F freely diffusing, fluorescent species in solution, the species is specified by an index with values $\alpha=1\ldots F$; $\alpha=0$ is associated with a constant background exhibiting Poisson statistics. The tightly-focused laser excitation and detection pinhole define the effective detection volume $V_{eff}$. $Exc(\tilde{x})$ is the excitation profile of the laser beam, and $CEF(\tilde{x})$ is the collection efficiency function of the collection optics [45]. $V_{eff}$ is defined by the detectivity, which is the product of the excitation and detection efficiency profiles $\phi(\tilde{x})=Exc(\tilde{x})CEF(\tilde{x})$: $V_{eff}=(\int dV \phi(\tilde{x}))^2/\int dV \phi^2(\tilde{x})$. For simulations, a Gaussian detectivity is assumed, $\phi(\tilde{x})=\exp[-2(x^2+y^2)/\omega^2 - 2z^2/l^2]$, where $\omega$ is the $1/e^2$ width of the confocal volume in the x and y directions, and l is length of the volume in the z direction ($V_{eff}=\pi^{3/2}\omega^2 l$). For examples, a numerically calculated confocal detection volume is used.

The primary parameters of a diffusing species $\alpha$ extracted from fluorescence fluctuation measurements are: (1) $c_\alpha$, the occupancy or average number of molecules in $V_{eff}$; the concentration $[\alpha]$ is obtained by dividing $[\alpha] = c_\alpha/V_{eff}$; (2) $\tau_\alpha^D$, the diffusion time of a molecule across $V_{eff}$ or the time at which the autocorrelation amplitude decays by a factor of 2 (excluding other fluctuations); for a Gaussian detection volume with l $\omega$, $$\tau_\alpha^D = \frac{\omega^2}{4D_\alpha},$$

where $D_\alpha$ is the diffusion constant; and (3) $q_{\alpha A}$, the brightness or count rate per molecule averaged over $V_{\it eff}$ in channel A. The average count rate for species $\alpha$ in channel A is $k_\alpha A = c_\alpha q_{\alpha A}$. For background, the only parameter is $\{k_{0_A}\}$, the count rate in each channel. PAID histograms are fitted to extract all the listed parameters for the diffusing species. Other properties extractable from fluorescence fluctuation measurements based on extensions of PAID modeling, include rates for intersystem crossing, triplet-state lifetimes, photobleaching rates, singlet-state lifetimes, and photon antibunching [46].

Application of PAID to Molecular Interactions:

The simplest molecular interactions are those between two species A and B, each with only one interaction site for the other. For the equilibrium, $A+B \rightleftharpoons AB$, the concentrations of A, B, and AB are related by the expression $K_d = [A][B]/[AB]$, where $K_d$ is the dissociation constant [47]. Macromolecular interactions are studied by fitting PAID histograms and extracting occupancy, diffusion time, and brightness for A, B, and AB. Since occupancies are directly proportional to concentration of species, they can be used to assess the affinity of the interaction; e.g., the $K_d$ can be determined by applying PAID to a series of measurements using increasing concentrations of B with respect to A. For interacting species, the F diffusing species (see previous section) are A, B, and AB. If A and B are labeled with the same fluorophore, they are distinguishable from AB because of differences in brightness (AB carries two fluorophores whereas A and B carry only one), and diffusion time. If A and B are labeled with fluorophores with distinct emissions detected by two different detection channels, they are also distinguishable from AB because of the difference in the relative number of photons detected in each channel (AB carries both fluorophores and is detected in both channels, whereas A and B carry only one and are detected in only one channel; see Introduction).

The dissociation constant can also be expressed in terms of the association rate constants $k_a$ and dissociation rate $k_d$, $K_d = k_d/k_a$. An upper bound for the association rate can be found considering diffusion-limited encounter rates between macromolecules A and B [47]. If A and B are modeled as spheres of radii $r_A$ and $r_B$, the diffusion-limited rate constant is given by $k_D = 4\pi N_A(D_A+D_B)(r_A+r_B)$. By assuming that A and B have equal sizes ($r_A = r_B$), and species B is present at 1 nM concentration, the encounter rate of any molecule of species A with molecules of the species B is $k_{encounter} < 10$ s$^{-1}$, <100-fold slower than typical diffusion times. Conversely, if species A is present at 1 nM concentration, the encounter rate of any molecule of species B with molecules of the species A is also $k_{encounter} < 10$ s$^{-1}$. To obtain a significant population of AB, the dissociation rate $k_d$ must be similar to or slower than the encounter rate. So, at nM concentrations, any association or dissociation events are extremely rare within the diffusion timescale, therefore, one only observes A, B, and AB (but not any association/dissociation events) and can treat the diffusing species as "static" species.

Model for PAID:

The model for the PAID function will now be described in detail. As an introduction, a general outline and the guiding principles of the model are given, which are used to fit the data using non-linear least squares method.

The assumption that the molecules in solution diffuse independently, with the time between association and dissociation events much longer than the diffusion time, allows the PAID function for all molecules to be expressed as a sum of convolutions of the PAID function for a single molecule with the photon count probability distributions for many molecules.

The expressions for single molecules are approximated by Monte Carlo simulation of possible diffusion paths through the confocal detection volume [48]. A scaling law is used to model changes in brightness or diffusion time (Eq. (36) and Eq. (46)). Depending on the accuracy desired, the confocal detection volume is set as an analytical Gaussian detection volume, as a numerical approximation, or as an experimentally measured detection volume, allowing the direct application of the expected detection volume to the model. The PAID model is able to account for the possible diffusion paths through that volume, in contrast to either FIDA or FIMDA [24, 32]. For FIDA or FIMDA, only the volume density for a given brightness value is required. This indeed simplifies these two models, but comes at the expense of not being able to model the possible diffusion paths.

To obtain the final expressions for the PAID function through the combination of the single-molecule expressions, it is necessary to compute many convolutions, which produces the primary bottleneck in the model calculation. Because of the wide temporal and dynamic ranges over which fluorescence fluctuations occur, logarithmic axes are desirable. For the most efficient calculation, the convolution method used must work in a logarithmic domain. However, pure Fast Fourier Transform (FFT) methods demand linearly spaced data, which quickly produces huge arrays. A method is presented below in accordance with the present invention that combines the use of the FFT with a quasi-logarithmic scale, making the model calculation practical.

Supporting Theory of Model for PAID:

A model of the PAID function in accordance with the present invention is provided for several species of diffusing molecules with a Poisson background in a tightly focused laser excitation volume. The PAID function is expressible in terms of the photon counting probability distributions and the PAID function for single molecules. The photon count probability distribution and the PAID function for single molecules are expressed in terms of four path integrals, which estimate using Monte Carlo simulations of diffusion paths. These path integrals need only be calculated once; changes in the diffusion time and brightness parameters can be accounted for by a scaling law. This means that, although the model is not expressed in closed form, it can still be used in a fitting routine.

Precise definitions of the effective detection volume $V_{\it eff}$ and the brightness per molecule in detector channel A, $q_{\alpha A}$ are needed. As a function of a molecule's spatial position, $\tilde{x} = [x,y,z]$, neglecting intersystem crossing to triplet states and assuming that the fluorescence lifetime is zero, the rate of photons $\lambda_{\alpha A}(\tilde{x})$ coming from a fluorescent molecule of species $\alpha$ is $$\lambda_{\alpha A}(\tilde{x}) = \sigma_\alpha \phi_\alpha I_0 d_{\alpha A} \text{Exc}(\tilde{x}) \text{CEF}(\tilde{x}) \tag{11}$$

$I_0$ is the excitation intensity at the center of the confocal volume, $\sigma_\alpha$ is the absorption cross-section of the fluorophore, $\phi_\alpha$ is the quantum efficiency of the fluorophore, and $\phi_{\alpha A}$ is the detection efficiency at the center of the confocal volume for detectors A. These can be grouped into one parameter $q_{\alpha A}^0 = d_{\alpha A} I_0 \sigma_\alpha \phi_\alpha$, the brightness at the center of the confocal volume for detector A. $\text{Exc}(\tilde{x})$ is the excitation profile of the laser beam, and $\text{CEF}(\tilde{x})$ is the collection efficiency function of the collection optics [45]. If there is more than one laser source, then Exc($\tilde{x}$) may be different for each. CEF($\tilde{x}$) in general varies as a function of detection wavelength. For simplicity, one uses the same Exc($\tilde{x}$) and CEF($\tilde{x}$) for each excitation and each detection wavelength. The detectivity is defined as the product of the excitation and detection efficiency profiles $\phi(\tilde{x}) \equiv Exc(\tilde{x})CEF(\tilde{x})$. For simulations, a Gaussian detectivity is assumed, $\phi(\tilde{x})=\exp[-2(x^2+y^2)/\omega^2-2z^2/l^2]$, where $\omega$ is the $1/e^2$ width of the confocal volume in the x and y directions, and l is length of the volume in the z direction. For the examples, we use the confocal detection volume for the oil immersion objective described below. With the new definitions, Eq. (11) can be written $$\lambda_{\alpha A}(\tilde{x}) = q_{\alpha A}{}^0 \phi(\tilde{x}) \quad (12)$$

The brightness per molecule $q_{\alpha A}$ is defined as the average photon count rate in detector channel A over the detection profile $\phi(\tilde{x})$, $$q_{\alpha A} = \frac{\int \lambda_{\alpha A}(\vec{x}) \phi(\vec{x}) dV}{\int \phi(\vec{x}) dV} = q_{\alpha A}^0 \frac{\int \phi^2(\vec{x}) dV}{\int \phi(\vec{x}) dV}, \quad (13)$$

where dV=dxdydz is an infinitesimal volume element. For the Gaussian detection profile, this equation reduces to $$q_{\alpha A} = \frac{q_{\alpha A}^0}{2^{3/2}}.$$

The effective detection volume is defined as in [20, 22, 49]:

$$V_{eff} = \frac{\left[\int \phi(\vec{x}) dV\right]^2}{\int \phi^2(\vec{x}) dV}. \quad (14)$$

For the case of the Gaussian detection volume above, this equation becomes $V_{eff}=\pi^{3/2}\omega^2 l$. With this definition; Eq. (12) is now written $$\lambda_{\alpha A}(\vec{x}) = (q_{\alpha A} V_{eff}) \frac{\phi(\vec{x})}{\int \phi(\vec{x}) dV}. \quad (15)$$

The occupancy $c_\alpha$ is the average number of molecules of species $\alpha$ within the detection volume. If there are $N_\alpha$ molecules of the diffusing species $\alpha>0$ in solution, and the volume of the solution is $V_{sol_1} V_{eff}$, then the following relationship with the occupancy $c_\alpha$ holds, $$\frac{N_\alpha}{V_{sol}} = \frac{c_\alpha}{V_{eff}}.$$

The density of molecules as a function of spatial position for species $\alpha$ is $$\rho_\alpha(\vec{x}) = \frac{c_\alpha}{V_{eff}}.$$

To calculate the average count rate from diffusing species $\alpha$, one integrates the density of molecules multiplied by the intensity as a function of spatial position, $$k_{\alpha A} = \int \rho_\alpha(\vec{x}) \lambda_{\alpha A}(\vec{x}) dV = c_\alpha q_{\alpha A} \quad (16)$$

The average count rate $k_{\alpha A}$ from a diffusing species $\alpha$ in detection channel A is the product of the occupancy $c_\alpha$ and the average brightness $q_{\alpha A}$. The total average count rate in detector A is the sum of the average rate of photons of all species and background $$k_A \equiv k_{0A} + \sum_{\alpha=1}^{N} k_{\alpha A}. \quad (17)$$

Average intensities are denoted by k, and instantaneous intensities are denoted by $\lambda$.

Spatial Distribution of Molecules Upon Detection of Start Photon:

The first step in modeling the PAID function is to obtain expressions for the spatial distribution of the fluorescent molecules at the time a start photon is received. At the time a start photon arrives from a diffusing source $\alpha>0$ (defined as time interval $\tau=0$), the molecule that emitted the photon is inside the effective detection volume, meaning that the spatial probability distribution for that molecule matches the excitation-detection volume. This can be seen as follows. Consider the intensity in the start detection channel of a molecule of species $\alpha$ as a function of spatial position, $\lambda_{\alpha S}(\tilde{x})$, given by Eq. (15) while specifying the detector channel A=S. The probability that a start photon is received from the molecule at a specific spatial position is directly proportional to the intensity in the start detection channel of the molecule at that position. So, the probability distribution $P_{\alpha h}^{corr}(\tilde{x})$ for the position of a molecule of species $\alpha$ when it emits a photon can be obtained by dividing the intensity $\lambda_{\alpha S}(\tilde{x})$ by its integral over all space, $$P_\alpha^{corr}(\vec{x}) = \frac{\lambda_{\alpha S}(\vec{x})}{\int dV \lambda_{\alpha S}(\vec{x})} = \frac{\phi(\vec{x})}{\int dV \phi(\vec{x})}, \quad (18)$$

where dV=dxdydz is an infinitesimal volume element. This expression assumes that there is no triplet state saturation, and that there is no significant diffusion within the fluorescence lifetime. The superscript "corr" means correlated, signifying that the subsequent photons coming from this molecule are correlated with the start photon.

In contrast, the molecules of a diffusing species $\alpha>0$ that did not emit the start photon are equally likely to be anywhere in the solution at $\tau=0$, so the probability distribution for these molecules is $$P_\alpha^{unc}(\vec{x}) = \frac{1}{V_{sol}}. \tag{19}$$

The superscript "unc" means uncorrelated, signifying that the photons coming from these molecules are uncorrelated with the start photon.

Calculation of the Cross-Calculation:

The cross-correlation measures the average rate of photons received in the stop detection channel T upon receiving a photon in the start detection channel S, normalized by the average count rate in the stop detection channel. As the main task in calculating the cross-correlation, we obtain the average rate of receiving stop photons from a source $\beta$ a time interval $\tau$ after receiving a start photon from source $\alpha$, $k_{\alpha A \to \beta T}(\tau)$. This is the rate averaged over all possible initial spatial positions as well as all possible later spatial positions. Although this will allow one to calculate the cross-correlation function, it will not allow the calculation of the PAID function without the further development of the theory as set forth below. To obtain the total density of molecules of a species $\beta$ at time interval $\tau=0$, upon receiving a start photon from a molecule of species $\alpha$, one adds the "correlated" and "uncorrelated" components:

$$\rho_{\alpha S \to \beta}(\vec{x},\tau=0) = P_\alpha^{corr}(\vec{x},\tau=0)\delta(\alpha,\beta) + N_\beta P_\beta^{unc}(\vec{x},\tau=0) \tag{20}$$

The second term on the right is the contribution of the $N_\beta$ molecules of species $\beta$ that did not emit the photon. If $\alpha=\beta$, then the molecule that emitted the photon gives the contribution indicated in the first term on the right, and there are $N_\beta-1$ uncorrelated molecules. Since $N_\beta \gg 1$, one can approximate $N_\beta - 1 \approx N_\beta$.

In order to obtain the cross-correlation from this initial distribution, the density of molecules at a later time can be calculated by integration against the Green's function for three-dimensional diffusion of species $\beta$ [50], $$g_\beta(\vec{x},\tau|\vec{x}_0) = (4\pi D_\beta \tau)^{-3/2} \exp\left[-\frac{(\vec{x}-\vec{x}_0)^2}{4D_\beta \tau}\right]. \tag{21}$$

The resulting density of molecules as a function of the spatial variables $\tilde{x}$ and time interval $\tau$ is $$\rho_{\alpha S \to \beta}(\vec{x},\tau) = \int dV_0 \rho_{\alpha S \to \beta}(\vec{x},\tau=0) g_\beta(\vec{x},\tau|\vec{x}_0) \tag{22}$$

or substituting Eqs. (18)-(20), and simplifying, $$\rho_{\alpha S \to \beta}(\vec{x},\tau) = \frac{c_\beta}{V_{eff}} + \delta(\alpha,\beta)\frac{\int dV_0 \phi(\vec{x}_0) g_\beta(\vec{x},\tau|\vec{x}_0)}{\int dV_0 \phi(\vec{x}_0)}, \tag{23}$$

The total count rate on the stop detector T for photons coming from molecules of species $\beta$ given that the start photon was from species $\alpha$, $k_{\alpha S \to \beta T}(\tau)$, is equal to the integral over space of the number density for molecules of species $\beta$ multiplied by the intensity in the stop photon stream of a molecule of species $\beta$ as a function of spatial position $\lambda_{\beta T}(\tilde{x})$:

$$k_{\alpha S \to \beta T}(\tau) = \int dV \rho_{\alpha S \to \beta}(\vec{x},\tau) \lambda_{\beta T}(\vec{x}) \tag{24}$$

Using Eq. (15) and Eq. (23), this expression becomes $$k_{\alpha S \to \beta T}(\tau) = k_{\beta T} + \delta(\alpha,\beta) q_{\beta T} \frac{\int dV \phi(\vec{x}) \int dV_0 \phi(\vec{x}_0) g_\beta(\vec{x},\tau|\vec{x}_0)}{\int dV \phi^2(\vec{x}_0)}. \tag{25}$$

The first term is the contribution of the uncorrelated molecules of species $\beta$ that did not emit the start photon. The second term is the contribution of the molecule that emitted the photon, if $\alpha=\beta$. This expression is valid for all diffusing species $\alpha,\beta > 0$. If the start photon came from the background process so that $\alpha=0$, there is no difference between the count rate at an arbitrary time t and at the moment the start photon is received. So, for $\beta=0$, the source $\alpha$ of the start photon does not matter, $$k_{\alpha S \to 0T}(\tau) = k_{0T} \tag{26}$$

For $\beta>0$, Eq. (25) is still valid if the start photon is from the background source, $\alpha=0$.

Equations (25) and (26) give us the average count rate in the stop detector channel T given that a photon was received in the start detector channel S from source $\alpha$. These can be used to calculate the cross-correlation function by summing $k_{\alpha\beta T}(\tau)$ over all sources $\beta$, as well as all possible sources $\alpha$ for the start photon. Each term is weighted with the count rate of each source $\alpha$ in the start detector channel S, $k_{\alpha S}$. To normalize the result, one divides by the product of the total count rate in the start channel $k_S$ multiplied by the total count rate in the stop channel $k_T$, as in Eq. (3). This gives the cross-correlation function for channel S and channel T, $$C_{ST}(\tau) = \frac{\sum_{\alpha=0}^{M}\sum_{\beta=0}^{M} k_{\alpha S} k_{\alpha S \to \beta T}(\tau)}{k_S k_T} \tag{27}$$

If a Gaussian detection volume is used for the detectivity $\phi(\tilde{x})$, the standard formulas for FCS are recovered.

While the above arguments using the density of molecules provide the correlation function, they will not be sufficient to calculate the PAID function $C_{STM}(n|\tau)$. The initial density of molecules given by Eq. (20) is still correct, but the information contained in the density of molecules is not sufficient to determine the distribution of correlation in the monitor photon count axis n. To be able to model the PAID function, it is necessary to know the history of the molecules, the possible diffusion paths of the molecules.

Photon Count Probability Distribution for a Single Path of a Single Molecule:

Before calculating the PAID function, the photon count probability distribution is obtained for the monitor detection channel given that a start photon was received from a molecule of species $\alpha$ at time interval $\tau=0$. A possible diffusion path l of a molecule in solution is defined by its spatial position as a function of time interval $\tau$, $\tilde{x}_l(\tau) = [x_l(\tau), y_l(\tau), z_l(\tau)]$. S is defined as the set of all possible paths l from all starting positions at time interval $\tau=0$ to all ending positions at time interval $\tau$. At time interval $\tau=0$, the probability distribution for the initial position is given by Eq. (18) for the molecule from species $\alpha$ that emitted the start photon $P(\tilde{x}_l(0)) = P_\alpha^{corr}(\tilde{x}_l(0))$ and by Eq. (19) for the molecules of species $\beta$ that did not, $P(\tilde{x}_l(0)) = P_\beta^{unc}(\tilde{x}_l(0))$. Each of the expressions for photon count probability distributions in this section and the following section can be applied to both correlated and uncorrelated molecules, so the superscript "corr" or "unc" is omitted. When the combination of the distributions of all molecules is described, these superscripts will be present. For species $\beta$, the probability for the whole path up to time interval $\tau$ is given by the following expression (following Eq. 8 in [51]):

$$P_\beta(l|\tau) = \lim_{\Delta\tau \to 0} \left( \prod_{h=0}^{\tau/\Delta\tau} \int_{dV} \frac{d\vec{x}_l}{(4\pi D_\beta \Delta\tau)^{3/2}} \right) P(\vec{x}_l(0)) \exp\left\{ -\frac{|\vec{x}_l^{h+1} - \vec{x}_l^h|^2}{4D_\beta \Delta\tau} \right\} \quad (28)$$

$$= P(\vec{x}_l(0)) \exp\left\{ -\int d\tau \frac{[\dot{\vec{x}}_l(\tau)]^2}{4D_\beta} \right\}$$

To specify that correlated paths are used, the superscript "corr" is added. To specify that uncorrelated paths are used, a superscript "unc" is added instead. The probability for the path l is obtained by multiplying the probability density for the initial position by the transition probability to every subsequent position spaced by a time interval $\Delta\tau$. The transition probability is the Green's function for three-dimensional diffusion given in Eq. (21).

The intensity in the monitor detector channel M for the molecule of species $\beta$ as a function of time is found using Eq. (15), $$\lambda_{\beta Ml}(\tau) = \lambda_{\beta M}[\vec{x}_l(\tau)] \quad (29)$$

This expression translates, for a path l, a diffusion path into an intensity path. Note that this expression gives the instantaneous intensity at the spatial positions along a diffusion path, not the intensity averaged over all possible spatial positions as was used in the previous section.

For a given path l of one molecule, the probability that n photons have been received at a time interval $\tau$ in detection channel M is $^1P_{\beta Ml}(n|\tau)$. The 1 indicates that it is for a single molecule. A differential equation-based approach is taken to obtain the distribution of photon counts, modified from [52], which contains the same information as the approach in [53]. The differential equation governing the time evolution of $^1P_{\beta Ml}(n|\tau)$ is:

$$\frac{\partial^1 P_{\beta Ml}(n|\tau)}{\partial \tau} = \lambda_{\beta Ml}(\tau)^1 P_{\beta Ml}(n-1|\tau) - \lambda_{\beta Ml}(\tau)^1 P_{\beta Ml}(n|\tau). \quad (30)$$

This equation gives the rate of change in the probability that n photons have been detected at a time $\tau$. The first term on the right gives the increase in this probability due to a photon detected when n−1 had previously been received. The rate of such photons is given by multiplying the total count rate $\lambda_{\beta Ml}(\tau)$ by the probability to have detected n−1 photons, $^1P_{\beta Ml}(n-1|\tau)$. The second term gives the decrease in the probability to have detected n photons due to a photon detected when n had previously been detected. The rate of such photons is given by multiplying the total count rate $\lambda_{\beta Ml}(\tau)$ by the probability to have detected n photons, $^1P_{\beta Ml}(n|\tau)$. The initial conditions are $^1P_{\beta Ml}(n=0|\tau=0)=1$, and $^1P_{\beta Ml}(n|\tau=0)=0$ for all $n \neq 0$. Equation (30) is an infinite series of coupled first order differential equations. By solving these equations using, for example, the generating function $$^1G_{\beta Ml}(s|\tau) = \sum_{n=0}^{\infty} s^{n1} P_{\beta Ml}(n|\tau)$$

one obtains the Poisson distribution:

$$^1P_{\beta Ml}(n|\tau) = \exp[-\Lambda_{\beta Ml}(\tau)] \frac{[\Lambda_{\beta Ml}(\tau)]^n}{n!} \quad (31)$$

$$\equiv Poi(\Lambda_{\beta Ml}(\tau), n),$$

where $$\Lambda_{\beta Ml}(\tau) \equiv \int_0^\tau \lambda_{\beta Ml}(\tau') d\tau' \quad (32)$$

the cumulative intensity. The photon count probability distribution at a time $\tau$ for a particular path depends only on the cumulative intensity $\Lambda_{\beta Ml}(\tau)$, which depends on the history of the intensity path in a way not seen with the cross-correlation in the previous section. There, the evolution of the instantaneous spatial probability distribution was sufficient to calculate the correlation function. Here, it is necessary to know not only the probability distribution for where the molecules are at the time interval $\tau$, but where they have been since the start photon was detected.

Photon Count Probability Distribution for all Paths of a Single Molecule:

When all possible intensity paths are taken into account, the photon counting probability distribution for a molecule of species $\beta$, $^1P_{\beta M}(n|\tau)$, is a weighted average over all paths of the photon counting probability distribution $^1P_{\beta Ml}(n|\tau)$, $$^1P_{\beta M}(n|\tau) = \int_S D(l) P_\beta(l|\tau)^1 P_{\beta Ml}(n|\tau) \quad (33)$$

$P_\beta(l|\tau)$ is given by Eq. (28), and S is the set of paths from all initial positions to all final positions after a time interval $\tau$. The only variable in $^1P_{\beta Ml}(n|\tau)$ that depends on the path is the value $\Lambda_{\beta Ml}(\tau)$, given by Eqs. (29) and (32). So, the path integral can be recast in terms of a simple integral of $^1P_{\beta Ml}(n|\tau)=Poi(\Lambda_{\beta Ml}(\tau),n)$ against the probability for a given value of $\Lambda_{\beta Ml}(\tau)$, $$^1P_{\beta M}(n|\tau) = \int_0^\infty d\Lambda \, ^1\tilde{P}_{\beta M}(\Lambda|\tau) Poi(\Lambda, n) \quad (34)$$

The expression $^1P_{\beta M}(n|\tau)$ is the Poisson transform of $^1\tilde{P}_{\beta M}(\Lambda|\tau)$. There are two possible spaces to work in, the photon count n-space and the cumulative intensity $\Lambda$-space. Functions in $\Lambda$ space are denoted with a tilde. The probability density $^1\tilde{P}_{\beta M}(\Lambda|\tau)$ is given by the expression $$^1\tilde{P}_{\beta M}(\Lambda|\tau) = \int_S D(l) P_\beta(l|\tau) \delta(\Lambda - \Lambda_{\beta Ml}(\tau)) \quad (35)$$

This is the probability density, considering all possible paths, to have a particular value of the cumulative intensity $\Lambda$ at a time interval τ. This integral is approximated later using Monte Carlo sampling of possible diffusion paths. (NOTE: this function $^1\tilde{P}_{\beta M}(\Lambda|\tau)$ corresponds to the probability density P(E) in [54]). The function $^1\tilde{P}_{\beta M}(\Lambda|\tau)$ depends on the diffusion time $\tau_\beta^D$ and brightness $q_{\beta M}$ of each species. Working in Λ space is advantageous because changes in the brightness and diffusion time parameters for the species β can be taken into account by scaling in the appropriate dimensions. A change in $q_{\beta M}$ corresponds to a scaling in the Λ dimension since $\Lambda_{\beta M l}(\tau)$ is directly proportional to $q_{\beta M}$. A change in $\tau_\beta^D$ corresponds to scaling in both the Λ and τ dimensions. The diffusion time enters the model only as a product of the form $D_o \Delta_\tau$ (see Eq. (28)). A scaling in the time interval τ axis accounts for a change in diffusion time in that expression. The scaling in Λ is also necessary since $\Lambda_{\beta M l}(\tau)$ is a cumulative integral over time which increases proportionally with a scaling in the time interval axis. If $^1\tilde{P}_{\sigma M}(\Lambda|\tau)$ is computed for a standard species σ with the diffusion time $\tau_\sigma^D$ and brightness $q_{\sigma M}$, then for a different species β with diffusion time $\tau_\beta^D$ and brightness $q_{\beta M}$, we have the scaling law $$^1\tilde{P}_{\beta M}(\Lambda|\tau) = {}^1\tilde{P}_{\sigma M}\left(\Lambda \frac{\tau_\sigma^D q_{\sigma M}}{\tau_\beta^D q_{\beta M}} \middle| \tau \frac{\tau_\sigma^D}{\tau_\beta^D}\right) \tag{36}$$

So, if one calculates $^1\tilde{P}_{\sigma M}^{corr}(\Lambda|\tau)$ for the molecule that emitted the start photon, and $^1\tilde{P}_{\sigma M}^{unc}(\Lambda|\tau)$ for the molecules that did not, any differences in diffusion time and brightness between molecular species can be calculated using the scaling law.

For the background source β=0, assumed to be a pure Poisson source with intensity $k_{0M}$ in the monitor detection channel, the photon count probability distribution is $$P_{0M}(n|\tau) = Poi(k_{0M}\tau, n) \tag{37}$$

In Λ-space, this is $$\tilde{P}_{0M}(\Lambda|\tau) = \delta(\Lambda - k_{0M}\tau) \tag{38}$$

Photon Count Probability Distribution for all Molecules in Solution:

The photon count probability distributions for single molecules is combined to obtain the photon count probability distribution for all molecules in solution. The molecules are assumed to be non-interacting (at least within the diffusion time), so one can assume independence when the photon count distributions are combined. This means that the photon count distribution for the combined source of all molecules and background is the convolution of the photon count distributions for all molecules and background (section 2.4.1.8). The photon count distribution of probability for all molecules in solution given that molecule h=1 of species α emitted a start photon is then, $$P_{\alpha M}(n|\tau) = \left(P_{0M} * {}^1P_{\alpha M}^{corr} * \prod_{\beta=1}^{F} ({}^1P_{1M}^{unc} *)^{N_\beta - \delta(\alpha,\beta)}\right)(n|\tau) \tag{39}$$

Note that the symbol for convolution * is inside the parentheses, indicating repeated convolutions rather than products. This is the convolution of the distributions for the background, the molecule that emitted the start photon, and all the other molecules starting with species β=1, all the way up to β=F. If the start photon came from the background α=0, then $P_{\alpha 1M}^{corr}$ is removed from the above successive convolutions. For α=β, there are $N_\alpha - 1$ convolutions for the uncorrelated molecules, since one of molecules emitted the photon and is taken into account by $^1P_{\alpha M}^{corr}$. As shown in section 2.4.1.9, these convolutions can be performed equivalently in Λ-space and n space. To convert Eq. (39) to Λ-space, replace each n with aΛ, and place a tilde over each quantity $\tilde{P}$, $$\tilde{P}_{\alpha M}(\Lambda|\tau) = \left(\tilde{P}_{0M} * {}^1\tilde{P}_{\alpha M}^{corr} * \prod_{\beta=1}^{F} ({}^1\tilde{P}_{1M}^{unc} *)^{N_\beta - \delta(\alpha,\beta)}\right)(\Lambda|\tau) \tag{40}$$

To obtain the photon count probability distribution for an arbitrary start photon, one sums over all possible sources a of the start photon, $$P_M(n|\tau) = \sum_{\alpha=1}^{F} \frac{k_{\alpha S}}{k_S} P_{\alpha M}(n|\tau) \tag{41}$$

The weighting factor $$\frac{k_{\alpha S}}{k_S}$$

is the probability that the start photon came from source α.

FIMDA uses a series of photon counting histograms with different time bin widths to extract the occupancy, diffusion time, and brightness of several diffusing species simultaneously. A modification of Eq. (39) can be used to model the FIMDA histogram. In PAID, a photon is received at the start of each counting interval. Because of this, there is a distinction between correlated and uncorrelated molecules. However, in FIMDA, the start of the counting interval is uncorrelated with the photon sequence. If the correlated photon count distribution in Eq. (39) is removed, one obtains a model for the FIMDA histogram. The single-molecule photon count distributions used in this model are calculated as described above.

Photon Count Distribution of Stop Channel Intensity for a Single Molecule in Solution:

To model the PAID function, one can combine the expressions for the photon count distribution with the cross-correlation given in the previous sections. The primary task is to calculate the distribution of the intensity in the stop detection channel T over the monitor photon count variable n at a time interval τ, $k_{\alpha S \to \beta TM}(n|\tau)$, given that a start photon was received from source α at time interval τ=0. This distribution, $k_{\alpha S \to \beta TM}(n|\tau)$, is related to the PAID function considering only a single species β by a constant factor: a normalization is applied to $k_{\alpha S \to \beta TM}(n|\tau)$, similar to Eq. (27), $$^1C_{STM}(n|\tau) = \frac{k_{\alpha S} k_{\alpha S \to \beta TM}(n|\tau)}{k_S k_T}.$$

For a single path l of a molecule from source β, the monitor photon count distribution of the stop channel intensity is calculated by multiplying the rate in the stop channel by the probability to have received n monitor photons, $$^1k_{\beta MTl}(n|\tau) = {}^1P_{\beta Ml}(n|\tau)\lambda_{\beta Tl}(\tau) \tag{42}$$

The superscript 1 indicates that the expression is for a single molecule. As a function of time interval $\tau$, the total intensity in the stop channel is $\lambda_{\beta TI}(\tau)$. $^1k_{\beta MTI}(n|\tau)$ is how this intensity is on average divided up among the different values of the monitor photon counts n.

When all possible paths are taken into account, the monitor photon count distribution of the stop channel intensity for a single molecule of species $\beta$, $^1k_{\beta MT}(n|\tau)$, is a weighted average over all paths of the distribution for a single path $^1k_{\beta MTI}(n|\tau)$, $$^1k_{\beta MT}(n\mid\tau) = \int_S D(l)P_\beta(l\mid\tau)\,^1P_{\beta MI}(n\mid\tau)\lambda_{\beta TI}(\tau) \qquad (43)$$

As in Eq. (35), $P_\beta(l|\tau)$ is given by Eq. (28), and S is the set of paths from all initial positions to all final positions after a time interval $\tau$. Eq. (43) can be rewritten as an integration of the Poisson distribution against the contribution to the stop channel intensity for a given value of cumulative intensity $\Lambda$, $$^1k_{\beta MT}(n\mid\tau) = \int_0^\infty d\Lambda\,^1\tilde{k}_{\beta MT}(\Lambda\mid\tau)Poi(\Lambda, n) \qquad (44)$$

where $$^1\tilde{k}_{\beta MT}(\Lambda\mid\tau) = \int_S D(l)P_\beta(l\mid\tau)\lambda_{\beta TI}(\tau)\delta(\Lambda - \Lambda_{\beta Ml}(\tau)) \qquad (45)$$

The difference between this equation and Eq. (35) is the additional factor of the intensity in the stop channel of the path l, $\lambda_{\beta TI}(\tau)$. Because of this factor, Eq. (45) gives the cumulative intensity distribution of the stop channel intensity, rather than the cumulative intensity distribution of probability.

The scaling law in Eq. (36) also applies here, with one additional factor, the brightness in the stop detector channel $q_{\beta T}$. If $^1\tilde{k}_{\sigma MT}(\Lambda|\tau)$ is computed for a standard species $\sigma$ with the diffusion time $\tau_\sigma^D$ and brightness $q_{\sigma M}$ in the monitor channel and brightness $q_{\sigma T}$ in the stop channel, then for a different species $\beta$ with diffusion time $\tau_\beta^D$, brightness $q_{\beta M}$ in the monitor channel and brightness $q_{\beta T}$ in the stop channel, we have the following scaling law $$^1\tilde{k}_{\beta MT}(\Lambda\mid\tau) = \frac{q_{\beta T}}{q_{\sigma T}}\,^1\tilde{k}_{\sigma MT}\left(\Lambda\frac{\tau_\sigma^D q_{\sigma M}}{\tau_\beta^D q_{\beta M}}\,\bigg|\,\tau\frac{\tau_\sigma^D}{\tau_\beta^D}\right) \qquad (46)$$

As with the cumulative intensity probability distribution in Eq. (35), one evaluation of the cumulative intensity distribution of the stop channel intensity is made for the molecule that emitted the start photon, $^1\tilde{k}_{\beta MT}^{corr}(\Lambda|\tau)$, and one for the molecules that did not, $^1\tilde{k}_{\beta MT}^{unc}(\Lambda|\tau)$. Any changes in the parameters $\tau_\beta^D$, $q_{\beta M}$, and $q_{\beta T}$ can be taken into account by using the scaling law.

For the background sources $\beta=0$, assumed to be a pure Poisson source with intensity $k_{0M}$ in the monitor detection channel and intensity $k_{0T}$ in the stop detection channel, the photon count distribution of stop channel intensity is $$k_{0MT}(n|\tau)=k_{0T}Poi(k_{0M}\tau,n) \qquad (47)$$

In $\Lambda$-space this becomes, $$\tilde{k}_{0M}(\Lambda|\tau)=k_{0T}\delta(\Lambda-k_{0M}\tau) \qquad (48)$$

PAID Function for All Molecules in Solution:

To account for all of the other molecules in solution, $^1k_{\beta MT}(n|\tau)$ is convolved with the photon count probability distribution for all other molecules and background. If the molecule in question emitted the start photon, then $$k_{\alpha S\to\beta MT}^{corr}(n\mid\tau) = \delta(\alpha,\beta)\left(P_{0M}*\,^1k_{\alpha MT}^{corr}*\prod_{\gamma=1}^F(^1P_{\gamma M}^{unc}*)^{N_\gamma-\delta(\alpha,\gamma)}\right)(n\mid\tau) \qquad (49)$$

The first factor is the background photon count probability distribution. The second factor is the monitor photon count distribution of stop channel intensity for the molecule that emitted the start photon. The rest of the factors come from the molecules of all the species that did not emit the photon. These are successive convolutions, not products, as indicated by the star * inside the parentheses. For $\alpha=\gamma$, there are $N_\alpha-1$ convolutions for the uncorrelated molecules, since one of molecules emitted the photon and is taken into account by $^1k_{\alpha MT}^{corr}$.

If the molecule in question did not emit the start photon, then $$k_{\alpha S\to\beta MT}^{unc}(n\mid\tau) = (N_\beta - \delta(\alpha,\beta)) \qquad (50)$$
$$\left(P_{0M}*\,^1P_{\alpha MT}^{corr}*\,^1k_{\beta MT}^{unc}*\prod_{\gamma=1}^F(^1P_{\gamma M}^{unc}*)^{N_\gamma-\delta(\alpha,\gamma)-\delta(\beta,\gamma)}\right)(n\mid\tau)$$

The pre-factor is how many molecules of species $\beta$ there are in solution. The first convolved factor is the background photon count probability distribution. The second convolved factor is the monitor photon count probability distribution for the molecule that emitted the start photon. The third convolved factor is the monitor photon count distribution of stop channel intensity for the molecule of species $\beta$ that did not emit the start photon. The rest of the convolved factors come from the molecules of all the species that did not emit the photon. For $\alpha=\gamma$, there is one less convolution for the uncorrelated molecules, since one of molecules emitted the photon and is taken into account by $^1P_{\alpha MT}^{corr}$. For $\beta=\gamma$, there is one less convolution for the uncorrelated molecules, since one of molecules is the one whose intensity is being calculated and is taken into account with $^1k_{\beta MT}^{unc}$.

For the background, $$k_{\alpha S\to 0MT}(n\mid\tau) = \left(k_{0M}*\,^1P_{\alpha MT}^{corr}*\prod_{\gamma=1}^F(^1P_{\gamma M}^{unc}*)^{N_\gamma-\delta(\alpha,\gamma)}\right)(n\mid\tau) \qquad (51)$$

The first factor is the monitor photon count distribution of stop channel intensity for the background. The second factor is the monitor photon count probability distribution for the molecule that emitted the start photon. The rest of the factors come from the molecules of all the species that did not emit the photon. For $\alpha=\gamma$, there is one less convolution for the uncorrelated molecules, since one of molecules emitted the photon and is taken into account by $^1P_{\alpha MT}^{corr}$.

The contributions to $k_{\alpha S \to \beta TM}(n|\tau)$ of all molecules is now summed, obtaining, $$k_{\alpha S \to \beta TM}(n|\tau) = k_{\alpha S \to \beta TM}^{corr}(n|\tau) + k_{\alpha S \to \beta TM}^{unc}(n|\tau) \quad (52)$$

The first term on the right is for any contribution that is correlated with the start photon, and the second term is for the contribution that is uncorrelated with the start photon. To obtain the final expression for the PAID function, we sum over all possible sources α of the start photon, weighted by the intensity of each source in the start channel, just as with the cross-correlation. To normalize the result, one divides by the product of the total count rate in the start channel $k_S$ multiplied by the total count rate in the stop channel $k_T$, as in Eq. (27).

$$C_{STM}(n|\tau) = \frac{\sum_{\alpha=0}^{M}\sum_{\beta=0}^{M} k_{\alpha S} k_{\alpha S \to \beta TM}(n|\tau)}{k_S k_T} \quad (53)$$

Remember, to convert any of the n-space expressions to Λ-space, replace each n with a Λ, and place a tilde over each quantity $\tilde{P}$ or $\tilde{k}$. This is the final expression for the PAID function. It is calculated by adjusting the distributions $^1\tilde{P}_{\beta M}^{unc}(\Lambda|\tau)$, $^1\tilde{k}_{\beta MT}^{unc}(\Lambda|\tau)$, $^1\tilde{P}_{\beta M}^{corr}(\Lambda|\tau)$ and $^1\tilde{k}_{\beta MT}^{corr}(\Lambda|\tau)$ for the parameters of each species β, and using Eqs. (49)-(53). A more detailed description will be provided below that demonstrates how to calculate the PAID function.

Combination of Sources for Probability Distribution:

As an example, assume one is given two photon count probability distributions, $P_1(n_1)$ and $P_2(n_2)$, and one wants to determine the photon count probability distribution for the combined source $P(n)$, where $n=n_1+n_2$. This can be determined by $$P(n) = \sum_{n_1=0}^{n} P_1(n_1) P_2(n-n_1 | n_1) \quad (54)$$

To obtain the probability to count n photons from the combined source, one sums over all possible values of $n_1$. For each value $n_1$, the value of $n_2$ is restricted so that the value of the combined total counts is correct, $n_2=n-n_1$. The probability to have $n_1$ counts from source 1 is $P_1(n_1)$, and the probability to have $n_2=n-n_1$ counts in source 2 given that there were $n_1$ counts from source 1 is $P_2(n-n_1|n_1)$. It is assumed that sources 1 and 2 are independent, so that $P_2(n-n_1|n_1)=P_2(n-n_1)$, and Eq. (54) reduces to a convolution, $$P(n) = \sum_{n_1=0}^{n} P_1(n_1) P_2(n-n_1) \equiv (P_1 * P_2)(n) \quad (55)$$

To combine more than two independent sources, one simply performs successive convolutions, $P(n)=(P_1*P_2*P_3*P_4*\ldots)(n)$.

Equivalence of Convolutions in n-Space and Λ-Space:

One property that needs to be established is the equivalence of performing convolutions in n space and Λ space. Consider three distributions $f(n|\tau)$, $g(n|\tau)$, and $h(n|\tau)$, such that h is the convolution of f and g:

$$h(n|\tau) = \sum_{n'=0}^{n} f(n'|\tau) g(n-n'|\tau) \equiv (f*g)(n|\tau) \quad (56)$$

One can write each of these distributions in n as a Poisson transformation, $$f(n|\tau) = \int_0^\infty \tilde{f}(\Lambda|\tau) Poi(\Lambda, n) d\Lambda \quad (57)$$

$$g(n|\tau) = \int_0^\infty \tilde{g}(\Lambda|\tau) Poi(\Lambda, n) d\Lambda$$

$$h(n|\tau) = \int_0^\infty \tilde{h}(\Lambda|\tau) Poi(\Lambda, n) d\Lambda$$

By substituting the Poisson transformation expressions for $f(n,\tau)$ and $g(n,\tau)$ into Eq. (56), one gets $$h(n|\tau) = \int_0^\infty d\Lambda_f \tilde{f}(\Lambda_f|\tau) \int_0^\infty d\Lambda_g \tilde{g}(\Lambda_g|\tau) \quad (58)$$

$$\sum_{n'=0}^{n} Poi(\Lambda_f, n') Poi(\Lambda_g, n-n')$$

$$= \int_0^\infty d\Lambda_f \tilde{f}(\Lambda_f|\tau) \int_0^\infty d\Lambda_g \tilde{g}(\Lambda_g|\tau) Poi(\Lambda_f + \Lambda_g, n)$$

$$= \int_0^\infty d\Lambda \left[\int_0^\Lambda d\Lambda' \tilde{f}(\Lambda'|\tau) \tilde{g}(\Lambda-\Lambda'|\tau)\right] Poi(\Lambda, n)$$

Since it is known that $$h(n, \tau) = \int_0^\infty d\Lambda \tilde{h}(\Lambda, \tau) Poi(\Lambda, n),$$

one finds $$\tilde{h}(\Lambda|\tau) = \int_0^\Lambda d\Lambda' \tilde{f}(\Lambda'|\tau) \tilde{g}(\Lambda-\Lambda'|\tau) = (\tilde{f}*\tilde{g})(\Lambda|\tau) \quad (59)$$

This shows that convolutions can equivalently be performed either in n-space or Λ-space.

Combinations of Sources for the Monitor Photon Count Distribution of Stop Channel Intensity:

The way to combine the monitor photon count distributions of stop channel intensity for multiple sources will now be demonstrated. This distribution, $k_{\alpha S \to \beta TM}(n|\tau)$, is related to the PAID function considering only a single species β by a constant factor: a normalization is applied to $k_{\alpha S \to \beta TM}(n|\tau)$, similar to Eq. (27)

$$^1 C_{STM}(n|\tau) = \frac{k_{\alpha S} k_{\alpha S \to \beta TM}(n|\tau)}{k_S k_T}.$$

Consider two intensity paths η and ξ from independent sources 1 and 2, respectively. The intensity of each path as a function of time interval is given for each detector channel A, $\lambda_{A\eta}{}^1(\tau)$ and $\lambda_{A\xi}{}^2(\tau)$. Each source may be a single molecule, or more than one molecule. For each path, the monitor photon count distribution of the stop channel intensity is calculated by multiplying the rate in the stop channel by the probability to have received n monitor photons, $$k_{MT\eta}{}^1(n|\tau) = P_{M\eta}{}^1(n|\tau)\lambda_{T\eta}{}^1(\tau)$$

$$k_{MT\xi}{}^2(n|\tau) = P_{M\xi}{}^2(n|\tau)\lambda_{T\xi}{}^2(\tau) \quad (60)$$

For the path $\eta$ of source 1, the total intensity in the stop channel is $\lambda_{T\eta}{}^1(\tau)$ as a function of time interval $\tau$. $k_{MT\eta}{}^1(n|\tau)$ gives how much of that intensity on average is detected for a given value of monitor photon counts n. $k_{MT\xi}{}^2(n|\tau)$ is interpreted similarly.

When all possible paths are taken into account, the monitor photon count distributions of the stop channel intensity, $k_{MT}{}^1(n|\tau)$ and $k_{MT}{}^2(n|\tau)$, are weighted averages over all paths of $k_{MT\eta}{}^1(n|\tau)$ and $k_{MT\xi}{}^2(n|\tau)$, respectively, $$k_{MT}^1(n\mid\tau) = \int_{S^1} D(\eta) P^1(\eta\mid\tau) k_{MT\eta}^1(n\mid\tau) \quad (61)$$

$$k_{MT}^2(n\mid\tau) = \int_{S^2} D(\xi) P^2(\xi\mid\tau) k_{MT\xi}^2(n\mid\tau)$$

$P^1(\eta|\tau)$ is the probability for a given intensity path $\eta$, and $S^1$ is the set of all intensity paths from up to a time interval $\tau$. $P^2(\xi|\tau)$ and $S^2$ are defined analogously. The monitor photon count probability distributions $P_M{}^1(n|\tau)$ and $P_M{}^2(n|\tau)$ are calculated by similar weighted averages, $$P_M^1(n\mid\tau) = \int_{S^1} D(\eta) P^1(\eta\mid\tau) P_{M\eta}^1(n\mid\tau) \quad (62)$$

$$P_M^2(n\mid\tau) = \int_{S^2} D(\xi) P^2(\xi\mid\tau) P_{M\xi}^2(n\mid\tau)$$

When one desires to determine the monitor photon count distributions of stop channel intensity for the combined source, $$\lambda_{T\eta\xi}(\tau) = \lambda_{T\eta}{}^1(\tau) + \lambda_{T\xi}{}^2(\tau) \quad (63)$$

As before, the monitor photon count distribution of the stop channel intensity is calculated by multiplying the rate in the stop channel by the probability to have received n monitor photons, $$k_{MT\eta\xi}(n|\tau) = P_{M\eta\xi}(n|\tau)\lambda_{T\eta\xi}(\tau) \quad (64)$$

When all possible paths are taken into account, the monitor photon count distributions of the stop channel intensity for the combined source, $k_{MT}(n|\tau)$, is $$k_{MT}(n\mid\tau) = \int_{S^1} D(\eta) P^1(\eta\mid\tau) \int_{S^2} D(\xi) P^2(\xi\mid\tau) k_{MT\eta\xi}(n\mid\tau) \quad (65)$$

Now, since sources 1 and 2 are independent, the monitor photon count probability distribution for the combined source is the convolution of the distributions for the individual sources.

$$P_{M\eta\xi}(n|\tau) = (P_{M\eta}{}^1 * P_{M\xi}{}^2)(n|\tau) \quad (66)$$

Using this along with Eq. (63), Eq. (64) is rewritten, $$k_{MT\eta\xi}(n\mid\tau) = \left[\sum_{n'=0}^n P_{M\eta}^1(n'\mid\tau) P_{M\xi}^2(n-n'\mid\tau)\right](\lambda_{T\eta}^1(\tau) + \lambda_{T\xi}^2(\tau)) \quad (67)$$

By substituting this into Eq. (65) and grouping terms from the same source, one gets $$K_{MT}(n\mid\tau) = \sum_{n'=0}^n \left\{ \left[\int_{S^1} D(\eta) P^1(\eta\mid\tau) k_{MT\eta}^1(n'\mid\tau)\right] \times \right. \quad (68)$$

$$\left[\int_{S^2} D(\xi) P^2(\xi\mid\tau) P_{M\xi}^2(n-n'\mid\tau)\right] + \left[\int_{S^1} D(\eta) P^1(\eta\mid\tau) \right.$$

$$\left. P_{M\eta}^1(n'\mid\tau)\right] \times \left[\int_{S^2} D(\xi) P^2(\xi\mid\tau) k_{MT\xi}^2(n-n'\mid\tau)\right] \right\}$$

Now, using Eqs. (61) and (62), one gets $$k_{MT}(n|\tau) = (k_{MT}{}^1 * P_M{}^2)(n|\tau) + (k_{MT}{}^2 * P_M{}^1)(n|\tau) \quad (69)$$

This equation convolves the monitor photon count distribution of stop channel intensity for each source with the photon count distribution of the other, and then adds the results. This equation along with Eq. (66) can be applied successively to combine many sources, $$k_{MT}(n\mid\tau) = \left(\sum_{sources\ i} k_{MT}^i * \prod_{j\neq i} P_M^j\right)(n\mid\tau) \quad (70)$$

This expression is used in this description to combine the monitor photon count distributions of stop channel intensity for all of the molecules in solution.

Evaluation of Kernels for Model:

The distributions $^1\tilde{P}_{oM}{}^{unc}(\Lambda|\tau)$, $^1\tilde{K}_{oMT}{}^{unc}(\Lambda|\tau)$, $^1\tilde{P}_{oM}{}^{corr}(\Lambda|\tau)$ and $^1\tilde{K}_{oMT}{}^{corr}(\Lambda|\tau)$ for the standard species $\sigma$ are evaluated using Monte Carlo generation of possible diffusion paths l, a modification of the simulations described. The standard species has a diffusion time $\tau_\sigma{}^D=1$, a brightness $q_{oM}=1$ in the monitor channel and brightness $q_{oT}=1$ in the stop channel (each of these has arbitrary units.) As in the previous section, a diffusion path l is simulated by a series of three-dimensional random distance steps, with mean $\mu=0$ and standard deviations $\sigma=\sqrt{2D\Delta\tau}$, where D is the diffusion constant and $\Delta\tau=10^{-2}\tau_\sigma{}^D$ is the time interval step. The initial positions are drawn from a uniform distribution across the simulation box $$P(\vec{x}_l(0)) = \frac{1}{V_{box}}$$

for the uncorrelated molecules, and from the detection profile $P(\tilde{x}_1(0)) = P_\sigma{}^{corr}(\tilde{x}_1(0))$ for the correlated molecules. The uncorrelated distributions are formed from simulations restricted to a finite box of size $V_{box}$ with periodic boundary conditions. Since the probability density for the initial uncorrelated spatial position is a constant with respect to spatial position, the size of the simulation box must be restricted to have a significant number of diffusion-driven crossings of the detection volume. The periodic boundary conditions are necessary to avoid a drain in the number of the molecules from the simulation box. For the correlated distribution, there is no restriction on the simulation box size. The probability density for the initial correlated spatial position is restricted to the detection volume, and the exit of the molecule from the region of the detection volume causes the average number of molecules per detection volume to return its uncorrelated value. For the species σ, the joint probability for the whole path up to time interval τ is given by the following expression (Eq. (28) without the limit):

$$P_\sigma(l|\tau) = \left(\prod_{h=0}^{\tau/\Delta\tau}\int_{dV}\frac{d\vec{x}_l}{(4\pi D_\sigma \Delta\tau)^{3/2}}\right)P(\vec{x}_l(0))\exp\left\{-\frac{|\vec{x}_l^{h+1}-\vec{x}_l^{h}|^2}{4D_\sigma\Delta\tau}\right\} \quad (71)$$

The distributions are evaluated at a series of time intervals τ that is logarithmically spaced over 10 decades from $\tau=10^{-6}\tau_\sigma^D$ to $\tau=10^4\tau_\sigma^D$ with 100 bins per decade. The cumulative intensity Λ bins are logarithmically spaced over 10 decades from $\Lambda=10^{-6}q_{\sigma M}\tau_\sigma^D$ to $\Lambda=10^4 q_{\sigma M}\tau_\sigma^D$ with 10 bins per decade. At each time interval τ in the logarithmically spaced series, the cumulative intensity $$\Lambda_{\sigma Ml}(\tau) \equiv \int_0^\tau \lambda_{\sigma Ml}(\tau')d\tau'$$

and the intensity in the stop channel $\lambda_{\sigma Tl}(\tau)$ are evaluated. An entry of 1 is entered at the corresponding (τ,Λ) bin in the cumulative intensity probability distribution, $^1\tilde{P}_{\sigma M}^{corr}(\Lambda|\tau)$ or $^1\tilde{P}_{\sigma M}^{unc}(\Lambda|\tau)$. Also, an entry $\lambda_{\sigma Tl}(\tau)$ is added to the corresponding (τ,Λ) bin in the cumulative intensity distribution of stop channel intensity, $^1k_{\sigma MT}^{corr}(\Lambda|\tau)$ or $^1k_{\sigma MT}^{unc}(\Lambda|\tau)$. After simulating a total of $10^5$ paths in the correlated case, and $10^7$ paths in the uncorrelated case, the estimated distributions are divided by the number of paths used. In the uncorrelated case, there are actually only $10^4$ diffusion paths simulated. Each diffusion path is used with $10^3$ evenly spaced starting points to give a total of $10^7$ effective paths. We can use many different starting points in this case because the molecules are uncorrelated: there are no special properties of the initial position.

Implementation of the Model and Fitting Routine:

The following is a summary of how to calculate the PAID function for a given set of parameters for F diffusing species and background: the diffusion time $\tau_\alpha^D$, the occupancy $c_\alpha$, the brightness per molecule $q_{\alpha A}$, and the background intensity $q_{0A}$. For each species β, one calculates the single molecule cumulative intensity distributions of probability and stop channel intensity for both the correlated and uncorrelated initial positions. Eq. (36) is used to calculate $^1\tilde{P}_{\beta M}^{corr}(\Lambda|\tau)$ and $^1\tilde{P}_{\beta M}^{unc}(\Lambda|\tau)$ and one uses Eq. (46) to calculate $^1k_{\beta MT}^{corr}(\Lambda|\tau)$ and $^1k_{\beta MT}^{unc}(\Lambda|\tau)$ from the distributions estimated for the standard set of parameters. In this way, the diffusion time of each species $\tau_\beta^D$, brightness in the monitor channel $q_{\beta M}$, and brightness in the stop channel $q_{\beta T}$ are all accounted for.

In building up the PAID function $C_{STM}(n|\tau)$ from these initial distributions, many convolutions are necessary. In order to perform them quickly, we have developed an efficient algorithm to compute convolutions in a quasi-logarithmic scale (see next section). $^1\tilde{P}_{\beta M}^{unc}(\Lambda|\tau)$, $^1k_{\beta MT}^{unc}(\Lambda|\tau)$, $_1P_{\beta M}^{corr}(\Lambda|\tau)$ and $^1k_{\beta MT}^{corr}(\Lambda|\tau)$ are rebinned into the quasi-logarithmic scale described below, and the convolutions are performed in Λ-space.

Now, Eqs. (49)-(52) are used to calculate the monitor photon count distributions of stop channel intensity for all of the categories of molecules. For each diffusing species, β>0, there is a distribution for the correlated and uncorrelated molecules.

The simulations used to form the distributions $^1\tilde{P}_{\beta M}^{corr}(\Lambda|\tau)$ and $^1k_{\beta MT}^{corr}(\Lambda|\tau)$ for correlated initial positions are not restricted to a finite simulation box. Initially, the molecules are inside the detection volume, but the molecules are allowed to diffuse out of the detection volume without restriction as the simulation time passes. Because the size of the simulation box is unrestricted, the difference between $N_\gamma$ and $N_\gamma-\delta(\alpha,\gamma)$ is ignored: in Eqs. (49)-(52), the expression $\delta(\alpha,\gamma)$ is dropped.

The simulations used to form the distributions $^1\tilde{P}_{\beta M}^{unc}(\Lambda|\tau)$ and $^1k_{\beta MT}^{unc}(\Lambda|\tau)$ for uncorrelated initial positions are restricted to a box with a volume $V_{box}$, which is larger than the effective detection volume: $V_{box_1}V_{eff}$. The box has harmonic boundary conditions, so that a molecule that comes out of one side reenters the other side. The fundamental concentration for the distributions formed from these simulations is $$\frac{1}{V_{box}}.$$

Successive convolution of the distribution $^1\tilde{P}_{\beta M}^{unc}(\Lambda|\tau)$ models an increasing concentration, but only in discrete steps. If the number of uncorrelated molecules of species β inside this box is $N_{box,\beta}$, then one models the uncorrelated photon count probability distribution using $(^1\tilde{P}_{\beta M}^{unc}(\Lambda|\tau)*)^{N_{box,\beta}}$. To have the proper occupancy, then the following relation should be satisfied, $$\frac{N_{box,\beta}}{V_{box}} = \frac{N_\beta}{V_{sol}} = \frac{c_\beta}{V_{eff}}. \quad (72)$$

Because the volume of the simulation box used for the distributions for uncorrelated molecules is much smaller than the volume of solution, the distributions $^1\tilde{P}_{\beta M}^{unc}(\Lambda|\tau)$ and $^1k_{\beta MT}^{unc}(\Lambda|\tau$ account for a much larger concentration than described previously, $$\frac{1}{V_{box}}$$

rather than $$\frac{1}{V_{sol}}.$$

To obtain the proper occupancy, the number of molecules $N_\beta$ in Eqs. (49)-(52) is replaced by the number of molecules in the simulation box, $N_{box,\beta}$. Using the small box size $V_{box}$ for the uncorrelated molecules and the large box size $V_{sol}$ for the correlated molecules, Eq. (49), which is for correlated molecules, is rewritten in Λ-space, $$\tilde{k}_{\alpha S \to \beta MT}^{corr}(\Lambda \mid \tau) = \delta(\alpha, \beta)\left(\tilde{P}_{0M} *^1 \tilde{k}_{\alpha MT}^{corr} * \prod_{\gamma=1}^{F}(^1\tilde{P}_{\gamma M}^{unc}*)^{N_{box,\gamma}}\right)(\Lambda \mid \tau) \quad (73)$$

Equation (50), which is for the uncorrelated molecules, is rewritten $$\tilde{k}_{\alpha S \to \beta MT}^{unc}(\Lambda \mid \tau) = \quad (74)$$

$$N_{box,\beta}\left(\tilde{P}_{0M} *^1 \tilde{P}_{\alpha MT}^{corr} *^1 \tilde{k}_{\beta MT}^{unc} * \prod_{\gamma=1}^{F}(^1\tilde{P}_{\gamma M}^{unc}*)^{N_{box,\gamma}-\delta(\beta,\gamma)}\right)(\Lambda \mid \tau)$$

Equation (51), which is for the background, is rewritten $$\tilde{k}_{\alpha S \to 0 MT}(\Lambda \mid \tau) = \left(\tilde{k}_{0M} *^1 \tilde{P}_{\alpha MT}^{corr} * \prod_{\gamma=1}^{F}(^1\tilde{P}_{\gamma M}^{unc}*)^{N_{box,\gamma}}\right)(\Lambda \mid \tau) \quad (75)$$

Finally, Eq. (52), which combines these expressions, is rewritten $$\tilde{k}_{\alpha S \to \beta TM}(\Lambda \mid \tau) = \tilde{k}_{\alpha S \to \beta MT}^{corr}(\Lambda \mid \tau) + \tilde{k}_{\alpha S \to \beta MT}^{unc}(\Lambda \mid \tau) \quad (76)$$

If $N_{box,\beta}$ is not an integer, then the distributions are calculated with the closest integer number of molecules in the simulation box $N'_{box,\beta}$, adjusting the brightness $q'_{\beta M}$ to satisfy the relation $q'_{\beta M} N'_{box,\beta} = q_{\beta M} N_{box,\beta}$. This keeps the total count rate from the species β constant, while using the closest integer for the number of molecules in the simulation box. Note that the adjusted value for the brightness $q'_{\beta M}$ is used only for the expressions for the uncorrelated molecules, not the correlated molecules.

Converting Eq. (53) to Λ-space, one gets for the cumulative intensity distribution of correlation, $$\tilde{C}_{STM}(\Lambda \mid \tau) = \frac{\sum_{\alpha=0}^{M}\sum_{\beta=0}^{M} k_{\alpha S}\tilde{k}_{\alpha S \to \beta TM}(\Lambda \mid \tau)}{k_S k_T} \quad (77)$$

This is then converted to n-space to get the PAID function, $$C_{STM}(n \mid \tau) = \int_0^\infty d\Lambda \tilde{C}_{STM}(\Lambda \mid \tau) Poi(\Lambda, n) \quad (78)$$

The kernels used as the basis for the model have finite sized bins in Λ, which are indexed by b and have the range $[\Lambda_{min}^b, \Lambda_{max}^b)$. Because of the finite bin size, what is really calculated is the average over a bin $$\frac{\int_{\Lambda_{min}^b}^{\Lambda_{max}^b} d\Lambda' \tilde{C}_{STM}(\Lambda' \mid \tau)}{\Lambda_{max}^b - \Lambda_{min}^b}.$$

It is assumed that the amplitude is constant across the bins, so that $$\tilde{C}_{STM}(\Lambda \mid \tau) \approx \frac{\int_{\Lambda_{min}^b}^{\Lambda_{max}^b} d\Lambda' \tilde{C}_{STM}(\Lambda' \mid \tau)}{\Lambda_{max}^b - \Lambda_{min}^b}$$

for Λ in the range $[\Lambda_{min}^b, \Lambda_{max}^b)$.

The expression for $C_{STM}(n \mid \tau)$ as calculated until now gives the instantaneous rates at a particular τ. However, the time interval bins for the photon counting data have finite extent, and so $C_{STM}(n \mid \tau)$ must be averaged over the range of the time bin. To calculate $\tilde{C}_{STM}(\Lambda \mid \tau)$ within the time interval $\tau_{min}$ and $\tau_{max}$, one interpolates between $\tilde{C}_{STM}(\Lambda \mid \tau_{min})$ and $\tilde{C}_{STM}(\Lambda \mid \tau_{max})$. $\tilde{C}_{STM}(\Lambda \mid \tau_{min})$ is projected forward in time from $\tau_{min}$, noting that the limits of a bin in cumulative intensity scales with time interval, $$\Lambda'_{min}(\tau) = \Lambda_{min}^b \frac{\tau}{\tau_{min}} \quad \text{and} \quad \Lambda'_{max}(\tau) = \Lambda_{max}^b \frac{\tau}{\tau_{min}}.$$

The value interpolated forward from $\tau_{min}$ is $$\tilde{C}_{STM}(\Lambda \mid \tau) \approx \frac{\int_{\Lambda_{min}^b}^{\Lambda_{max}^b} d\Lambda' \tilde{C}_{STM}(\Lambda' \mid \tau)}{(\Lambda_{max}^b - \Lambda_{min}^b)\frac{\tau}{\tau_{min}}},$$

where b is chosen so that $$\Lambda_{min}^b \leq \Lambda \frac{\tau_{min}}{\tau} < \Lambda_{max}^b.$$

Similarly, the value interpolated backward from $\tau_{max}$ is $$\tilde{C}_{STM}(\Lambda \mid \tau) \approx \frac{\int_{\Lambda_{min}^b}^{\Lambda_{max}^b} d\Lambda' \overline{C}_{STM}(\Lambda' \mid \tau)}{(\Lambda_{max}^b - \Lambda_{min}^b)\frac{\tau}{\tau_{max}}},$$

where b is chosen so that $$\Lambda_{min}^b \leq \Lambda \frac{\tau_{max}}{\tau} < \Lambda_{max}^b.$$

The interpolated values are averaged over the rectangle bounded by $\tau_{min}, \tau_{max}, \Lambda_{min}^b$, and $\Lambda_{max}^b$. Note that more than one bin may contribute to the averaging.

The final integration over $\Lambda$ shown in Eq. (78) is implemented as a matrix multiplication. The approximation that the value of $\tilde{C}_{STM}(\Lambda|\tau)$ is constant over a bin with limits $\Lambda_{min}^b$, and $\Lambda_{max}$ leads to the approximation, $$C_{STM}(n|\tau) = \sum_b \frac{\int_{\Lambda_{min}^b}^{\Lambda_{max}^b} d\Lambda' \tilde{C}_{STM}(\Lambda'|\tau)}{\Lambda_{max}^b - \Lambda_{min}^b} \int_{\Lambda_{min}^b}^{\Lambda_{max}^b} d\Lambda' Poi(\Lambda', n) \quad (79)$$

The integral on the right can be expressed in terms of the incomplete gamma function $$\gamma(a, x) = \frac{1}{\Gamma(a)} \int_0^x e^{-t} t^{a-1} dt, \quad (80)$$

$$\int_{\Lambda_{min}^b}^{\Lambda_{max}^b} Poi(\Lambda, n) d\Lambda = \gamma(n+1, \Lambda_{max}^b) - \gamma(n+1, \Lambda_{min}^b)$$

The bin spacing is kept fixed, so the integrals in Eq. (80) need to be performed only once to create the matrix.

Figure 5:
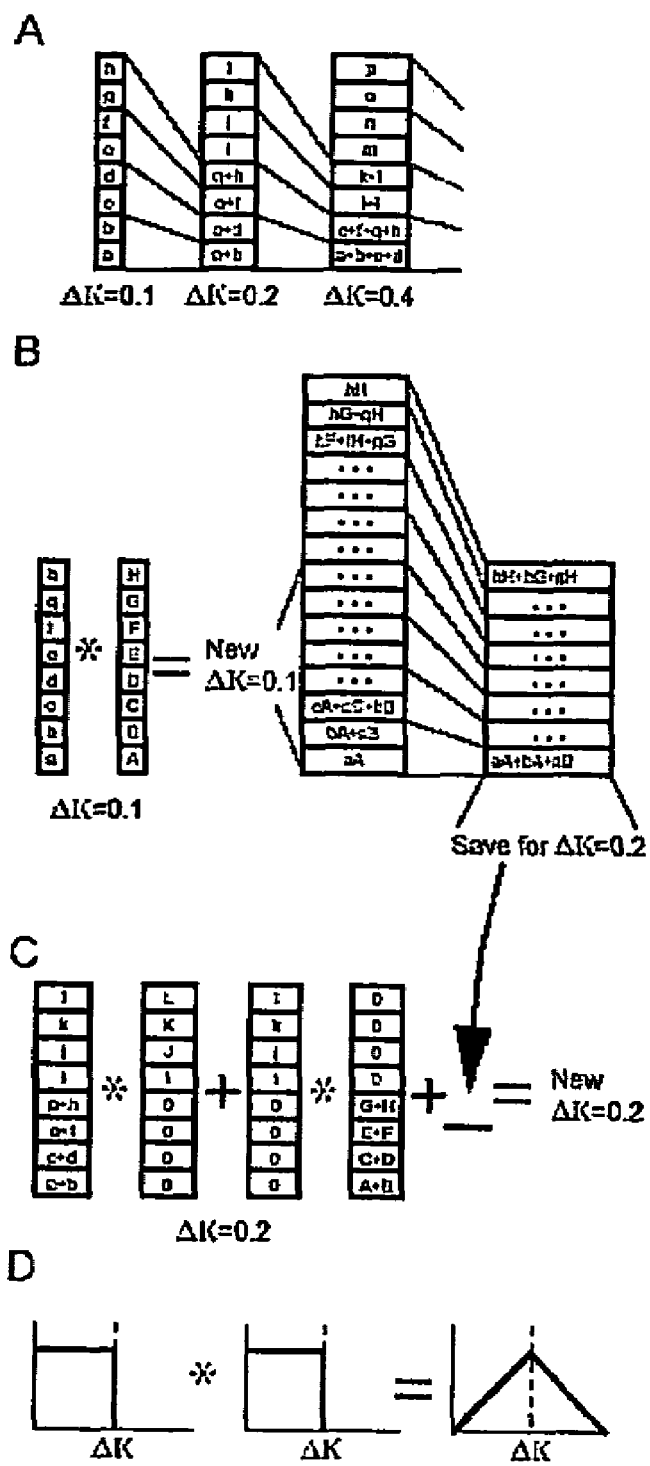
FIG. 5A shows the structure of the arrays with quasi-logarithmic spacing used for fast convolutions.
FIGS. 5B and 5C illustrate how the convolution of two series of such arrays is performed.
In FIG. 5D, the convolution of two-step functions is shown.

Efficient Calculation of Convolutions in a Quasi-Logarithmic Scale:

Because of the large number of convolutions necessary to calculate the PAID histogram, it is necessary to have an efficient algorithm for convolutions. The standard method is to Fast Fourier Transform (FFT) the data, multiply the data in the complex transform space, and then FFT back to real space (See for example Ch. 13 of [44]). The FFT, however, requires evenly spaced bins, which can produce huge arrays if one wants a large dynamic range. A convolution method inspired by the multiple-tau correlation technique [42, 43] that uses the FFT for small convolutions is preferred. For each vector (a and b) to be convolved, one produces a series of linearly spaced arrays of length 64, where the resolution of each is reduced by a factor of 2 compared to its predecessor. The structure of these vectors is shown in FIG. 5A. In the figure, the arrays are of length 8 (rather than 64) for each factor of 2 in resolution. The array with the smallest spacing is shown at the left. In FIG. 5A, the first array has a spacing of $\Delta\Lambda=0.1$. The second array has double the spacing, $\Delta\Lambda=0.2$. The first four elements are each made up of a sum of two elements from the first array. The third array has a spacing that is doubled again, $\Delta\Lambda=0.4$. Again, the first four elements are each made up of a sum of two elements from the second array. Continuing this structure to successively lower resolution, one obtains a series of linearly spaced arrays that can efficiently span a large dynamic range.

In FIGS. 5B and 5C, we illustrate how the convolution of two series of such arrays is performed. One array is labeled with lower-case letters, and the other is labeled with upper-case letters. To calculate the convolution of two vectors, a*b, the arrays with the smallest spacing ($\Delta\Lambda=0.1$) are convolved with each other first, as shown in FIG. 5B. The FFT procedure described above is used, where the arrays are zero-padded to twice the original length. The lower half of the array becomes the new array for the smallest spacing. The whole array is rebinned to the next largest spacing, and serves as a contribution to the convolution with spacing $\Delta\Lambda=0.2$.

In FIG. 5C, it is shown how the convolution for the larger spacing $\Delta\Lambda=0.2$ is performed. Because part of the convolution with that spacing has already been performed, one needs to exclude that contribution in subsequent calculations. This is done by setting (or "clipping") the lower half of one sub-array (lower-case) to 0, and convolving it with the other sub-array (upper-case). The clipped version from a is convolved with the full version from b, and vice versa. By adding these results with the array obtained by rebinning the result with spacing $\Delta\Lambda=0.1$, one obtains the final result for $\Delta\Lambda=0.2$. This allows the use of information from higher resolution arrays to contribute to the convolutions with lower resolution arrays.

In the quasi-logarithmically spaced arrays, the function to be convolved can be approximated by a series of steps; over the range of each bin, the function is assumed to be constant. When two such steps are convolved, one gets a triangle, shown in FIG. 5D. The convolution of the two steps leaks into the next bin. The discrete convolutions shown in FIGS. 5B and 5C do not account for this because they assume that the function is nonzero only at discrete values. In order to approximate the continuous functions with the method presented, the convolution is shifted one-half bin up after each FFT-based convolution in FIGS. 5B and 5C.

In Eqs (73)-(75), there are successive convolutions performed on the same array which have the form $({}^1\tilde{P}_{\gamma M}^{unc}*)^{N_{box,\gamma}}$. In order to compute $N_{box,\gamma}$ successive convolutions on the original distribution ${}^1\tilde{P}_{\gamma M}^{unc}$, we can use a trick to prevent performing $N_{box,\gamma}$ convolutions directly. The number $N_{box,\gamma}$ is expressed in binary. By recursively convolving the original array, one obtains a series of vectors for each convolved power of 2: 1,2,4,8, . . . By convolving only those convolved powers of 2 in the binary representation of $N_{box,\gamma}$, one obtains $({}^1\tilde{P}_{\gamma M}^{unc}*)^{N_{box,\gamma}}$. This allows the number of convolutions performed to increase logarithmically with $N_{box,\gamma}$.

EXAMPLES OF PAID APPLICATIONS

In the following examples of the present invention we use single- and dual-channel simulations and experiments to illustrate some of the applications of the use of PAID. Labeled DNA constructs as well as an RNA Polymerase-DNA interaction are used to show that PAID obtains expected results. These examples are not limiting; many other applications are possible, including those with multiple channels, and more monitor channels.

Materials and Methods

Preparation of DNA:

We used fluorescently-labeled DNA fragments as model systems for exploring the capabilities of PAID. The fluorophores used were Cy3B ($\lambda_{ex}$~560 nm, $\lambda_{em}$~580 nm), Cy3 ($\lambda_{ex}$~550 nm, $\lambda_{em}$~570 nm) and Cy5 ($\lambda_{ex}$~650 nm, $\lambda_{em}$~670 nm). Six DNA fragments were synthesized (the nomenclature used in the superscript report the fluorophore, the DNA position, and the DNA strand where the fluorophore was introduced; T: top strand, B: bottom strand): (1) DNA$^{Cy3B,1T}$, (2) DNA$^{Cy3B,1T/Cy3B,65B}$, (3) DNA$^{Cy5,1T}$, (4) DNA$^{Cy3,65B}$, (5) DNA$^{Cy5,1T/Cy3,65B}$ and (6) DNA$^{Cy5,65B}$. DNA fragments were prepared using standard PCR protocols [55] with one or two 5'-labeled DNA primers, followed by purification using non-denaturing gel electrophoresis. The sequence had 65 base pairs. Mixtures of DNA$^{Cy3B,1T}$ and DNA$^{Cy3B,1T/Cy3B,65B}$ were prepared for single-channel applications, and mixtures of DNA$^{Cy5,1T}$, DNA$^{Cy3,65B}$, and DNA$^{Cy5,1T/Cy3,65B}$ for dual-channel applications. In all cases, the intramolecular separation between the two fluorophores is large (65 bp, ~240 Å) to preclude FRET between the fluorophores. Data were acquired for 5 min using 30 μM-1 nM DNA in 20 mM HEPES-NaOH (pH 7), 50 mM NaCl, 5% glycerol, and 1 mM mercaptoethylamine (Fluka, Milwaukee, Wis.). We added 0.1% BSA (Panvera, Madison, Wis.) to the $DNA^{Cy3B,17/Cy3B,65B}$ and $DNA^{Cy3B,17}$ samples to reduce adsorption onto surfaces. The concentration of $DNA^{Cy5,17}$ was determined using UV-V is spectrophotometry and fluorescence spectrophotometry to calibrate concentrations determined from FCS measurements. Higher concentration (10-25 nM) samples were prepared for all DNA fragments, and occupancies and diffusion times were extracted using FCS as a basis for dilutions.

Preparation of RNAP and RNAP-DNA Complex:

*Escherichia coli* RNAP core was purchased from Epicentre (Milwaukee, Wis.), and RNAP σ subunit ($σ^{Cys569}$) was purified and labeled at amino acid Cys569 using tetramethylrhodamine (TMR) as described [56]. RNAP holoenzyme and RNAP-DNA complexes were formed essentially as described [56], using $DNA^{Cy5,65B}$ for the formation of the complex; the complex was diluted to 1 nM nominal concentration for the PAID measurements. The large distance (>>100 Å) between TMR and Cy5 in the RNAP-DNA open complex precludes FRET between the fluorophores [57]. After formation of the RNAP-DNA complex, the sample was loaded in non-denaturing 5% polyacrylamide gels and was electrophoresed at 10 V/cm for 1 hour; the resulting gels were imaged using an x-y fluorescence imager (Molecular imager FX, Biorad, Hercules, Calif.) equipped with 532-nm and 633-nm excitation lasers (for excitation of "yellow" and "red" fluorophores respectively), and 585BP60 and 640LP emission filters (for detecting "yellow" and "red" channel emissions, respectively).

Confocal Fluorescence Microscopy:

The instrumentation used is similar to that described in diffusion-FRET studies [(see FIG. 2) and [11, 12]]. For single-channel experiments, the 532 nm line from a solid-state pumped Nd:YAG laser (GCL-100-S, Crystalaser, Reno, Nev.; 100 kW/cm$^2$; excites Cy3 and Cy3B) was introduced using fiber optics. An excitation dichroic mirror (DM1) was used to reflect the laser light, while transmitting fluorescence emission (400-535-635 TBDR, Omega Optical, Brattleboro, Vt.). For the dual-channel experiments (DNA fragments and RNA Polymerase), two laser beams, 514 nm Ar$^+$ (543-A-A02, Melles-Griot, Carlsbad, Calif.; 200 kW/cm$^2$; excites Cy3 and 1M, and to a much lesser degree, Cy5), and 633 nm HeNe (05-LHP-171, Melles-Griot, Carlsbad, Calif.; 66 kW/cm$^2$; excites Cy5) were used. A different dichroic mirror (DM1; 390-510-630 TBDR, Omega optical, Brattleboro, Vt.) was used to reflect the two laser lines, while transmitting the emissions of TMR, Cy3, and Cy5. For both experiments, the laser excitation is focused 20 μm inside the solution by a 100×1.3 NA Zeiss Neofluar oil-immersion objective. Fluorescence from the detection volume is focused by the microscope tube lens (L1) on a 100 μm pinhole (PH) and split with a dichroic mirror (DM2; 630 DMLP, Omega Optical) into two detection channels: the Cy5 channel [filtered using a 650LP filter (BP1), Omega Optical], and the TMRCy3/Cy3B channel [filtered using a 580DF60 filter (BP2), Omega Optical]. Silicon avalanche photodiodes (APD1 and APD2; SPCM-AQR-14, PerkinElmer, Vaudreuil, QB, Canada) detect fluorescence photons, photon-associated electronic pulses are timed by a counter-timer board (PCI-6602, National Instruments, Austin, Tex.), and stored in a PC.

Simulation of Translational Diffusion of Molecules, and Photon Emission and Detection:

Simulations for translational diffusion, photon emission and detection of molecules were performed similarly to [58]. A Gaussian detection volume with ω=0.35 μm, l=1.75 μm is placed at the center of a 3D-simulation box with size $V_{box}$=3.5×3.5×17.5 μm$^3$, assuming periodic boundary conditions (a molecule that leaves $V_{box}$ reappears at the opposite side with the same lateral position); a fixed number of molecules is placed inside the box. Diffusion in and out of the detection volume is simulated by a series of steps of Δt=1 μs, a timescale short enough to ignore the effects of diffusion ($τ^D$≧100 μs for our systems) on the excitation rate of the molecules within one step. At each time step, the distance step for each dimension (x,y,z) is determined by a pseudorandom number generated with a Gaussian distribution [44], with mean μ=0 and standard deviation $σ=\sqrt{2DΔt}$, where D is the diffusion constant. The diffusion-step-generation distribution is taken directly from the Green's function for 3D-diffusion [50]. For each diffusion step, a series of pseudo-random numbers is generated with an exponential distribution with a decay rate λ that depends on the excitation rate for the molecule's position until time Δt is passed, thereby generating a series of arrival times for emitted photons; the fluorescence lifetime is assumed to be zero, thus ignoring saturation and other photophysical effects. Finally, a second pseudorandom number is generated to determine if the photon is detected, and, if it is, which channel detects the photon. The time of arrival and detection channel of each detected photon is saved. The resulting photon sequences can be subjected to any of the possible data reduction and analysis methods. The idealized conditions described above (Gaussian detection volume, neglected fluorescence lifetime) are used for the simulations since they are well-modeled by each of the data analysis methods.

Fitting Routine:

The Levenberg-Marquardt nonlinear least squares fitting procedure [59] is used to extract the parameters from the data, calculating the necessary partial derivatives numerically. The model used is described in detail above. To estimate the standard deviation of errors, we use ten independent instances of the histogram to calculate an estimate of the statistical errors of each bin. The statistical errors are used as weights in the fitting routine (this method is used for FCS in [58]. If a bin is nonzero in fewer than ten instances, it is excluded from the fit. Without this restriction, we found that only a few points dominate the value for χ$^2$ (the χ$^2$ merit function is not ideal for sparsely populated bins in histograms).

Calculation of Detection Volume and Diffusion Parameters:

A numerically-approximated, non-Gaussian volume is used for the analysis to account for our experimental conditions. The laser excitation profile for an oil-immersion objective focused 20 μm inside the aqueous solution was calculated using Monte Carlo integration of plane-wave contributions using expressions from [60, 61], simplified to scalar diffraction, and accounting for the water-glass dielectric interface. The effect of the pinhole in the detection path (100 μm) was calculated using geometric optics [45], accounting for the water-glass dielectric surface. The peaks of the excitation profile and detection profile were translated with respect to each other to assure good overlap in the z direction (adjustment of the pinhole or the APDs along the emission light path to maximize the signal would produce similar results). By multiplying the two profiles, we obtain the detection volume which forms the basis for calculating the kernels used for fitting the experimental data. The size of the calculated effective detection volume is 3.2 μm$^3$. For this volume, a concentration of 1 nM corresponds to an occupancy of 1.9. The diffusion time of a molecule of species α with a diffusion constant $D_α$ through this detection volume, was calculated by simulating many paths through the detection volume: $τ^D$= (2.8×10$^{-10}$ cm$^2$)/$D_α$. Since the persistence length of dsDNA is ~150 bp or 500 Å [62], one can treat the DNA fragments as rod-like polymers with length L≈240 Å, and diameter b≈20 Å, with averaged translational diffusion constant [19]:

$$D = \ln(L/b) k_B T / 3\pi \eta L \qquad (81)$$

η is the dynamic viscosity of the solution [η=1.16 mPa·s for aqueous solution with 5% v/v glycerol; [63]]. For T=25° C., D=3.9×10⁻⁷ cm²/s, using this diffusion constant, the DNA fragments have a diffusion time of $\tau^D$=710 µs in the calculated detection volume. We model the RNAP holoenzyme (dimensions 120×140×150 Å, [57]) as a sphere with radius in the range 60-75 Å, where $$D = k_B T / 6\pi \eta R \qquad (82)$$

In this case, the expected diffusion time is 0.9-1.1 ms.

Fitting Routine:

The Levenberg-Marquardt nonlinear least squares fitting procedure [59] is used to extract the parameters from the PAID histograms, calculating the necessary partial derivatives numerically. To estimate the standard deviation of errors, we use ten independent instances of the histogram to calculate an estimate of the statistical errors of each bin. The statistical errors are used as weights in the fitting routine [58]. If a bin is nonzero in fewer than ten instances, it is excluded from the fit. Without this restriction, we found that only a few points dominate the value for $\chi^2$ (the $\chi^2$ merit function is not ideal for sparsely populated bins in histograms). The ten independent instances were individually fitted (with a variety of initial conditions, checking for convergence), extracting the means and standard errors of the model parameters. The standard error of the mean with 10 instances is ~3 ($\sqrt{N}$, where N=10 is the sample size) times smaller than the sample standard deviation for each parameter. The same procedure is used for FIMDA, FCS, and FIDA. For each method, the model used was specialized to diffusion within a Gaussian detection volume (excluding triplet state fluctuations or other dynamics). FIMDA histograms were formed using the same bins as the PAID histograms, and the spacing between counted intervals was set to 10 µs for all time bin widths.

For the experimental data sets, 300 s of data were split into 10 sections of 30 s each; PAID histograms were calculated for each section, and the standard deviation of each bin was calculated to estimate the error of each bin; each section was fit separately, and the mean and error of the mean of each fitted parameter was calculated. Because the PAID model does not yet account for triplet state related fluctuations, the range of fitting for the experiments is restricted to time intervals greater than 10 µs to minimize the effects on fitting. The procedure was modified for the low-occupancy dual-channel experimental data since there were too few bursts from $DNA^{Cy5,1T/Cy3,65B}$ and $DNA^{Cy5,1T}$, resulting in large errors for the extracted diffusion times. To obtain better statistics, the histogram for all 300 s was fitted, and subsequent bootstrap sampling was used to obtain error estimates for the extracted parameters [64]. To obtain one bootstrap sample, the data were split into 10 30-s sections; 10 of these sections were randomly selected with replacement (the same section can be selected multiple times, or omitted). The PAID histograms for the selected sections were then averaged. We obtained 10 bootstrap samples in this manner, and fit each of the resulting histograms; the standard deviation of the 10 values extracted for each parameter is quoted as error bars for low-occupancy data.

Figure 6:
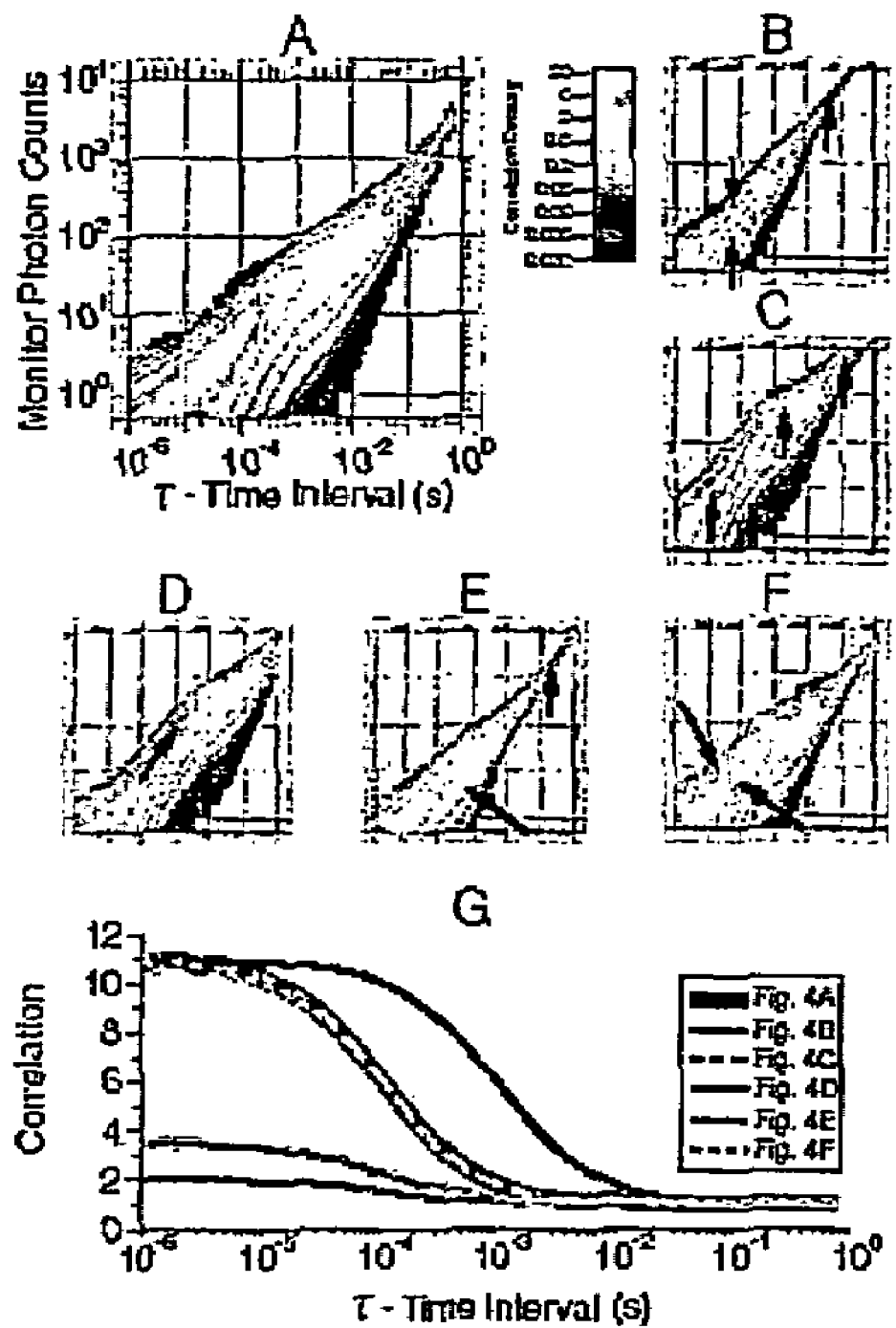
FIG. 6 shows the effects of changes in the characteristics of diffusing molecules on the single-channel PAID histogram. The first histogram (6A) was formed from a single-channel simulation, with a single diffusing species (start=stop=monitor channel). x axis, time interval between the start and stop photons; y axis, number of monitor photon counts between them. The occupancy is $c_1=0.1$, the diffusion time is $\tau_1^D=100$ µs, the brightness is $q_{11}=50$ kHz, and the background count rate is $q_{01}=0$ kHz.

Graphical Representation of Single-Channel Examples Using PAID:

The PAID histogram in accordance with the present invention is useful simultaneous measurements of diffusion time, brightness, and occupancy. We now describe how the parameters of a single diffusing species (occupancy, $c_1$; brightness per molecule in channel (A=1), $q_{11}$; diffusion time, $\tau_1^D$; and background count rate, $k_{01}$) affect the PAID histogram for a single-channel experiment. FIG. 6A shows the PAID histogram for a 30 s simulation with $c_1$=0.1, $\tau_1^D$100 µs, $q_{11}$=50 kHz, and $k_{01}$=0 kHz. At time interval τ=0, a photon from one of the diffusing molecules is detected; the position probability distribution for the molecule that emitted the photon matches $V_{eff}$. At τ=0, the autocorrelation amplitude from FCS is $C_{SS}$(τ=0)=($c_1$+1)/$c_1$[65]. This means that there are, on average, $c_1$+1 molecules of species α=1 inside $V_{eff}$ (since the molecules are assumed to be independent and there are numerous other molecules in a solution of a large volume, the presence of one molecule of a species does not affect the probability of a second molecule being present). While the molecule that emitted the photon is present (time interval τ $\tau_1^D$), the average count rate in channel A is (1+$c_1$)$q_{11}$. After a time interval $\tau_1 \tau_1^D$, the molecule that emitted the photon has diffused out of $V_{eff}$, and the average count rate returns to the value for an arbitrary time, $c_1 q_{11}$. There is a ridge of high correlation density at small τ, (FIG. 6A, white and red contours) that decays with a time scale τ $\tau_1^D$ (as with autocorrelation in FCS). Since the count rate at this time interval is (1+$c_1$)$q_{11}$, the peak of high correlation density follows a trajectory in the histogram of the form log $n_1$ log[(1+$c_1$)$q_{11}$]+ log τ, where log⌊(1+$c_1$)$q_{11}$⌋ is the "vertical offset" of the red ridge in FIG. 6A. After the molecule diffuses out of $V_{eff}$, the peak decays in height, indicating that the molecules present are uncorrelated with the initial photon. The count rate decreases to the average count rate, $c_1 q_{11}$, and the correlation density peak follows a trajectory in histogram of the form log n log ($c_1 q_{11}$)+log τ, where log ($c_1 q_{11}$) is the vertical offset of the second, orange ridge in FIG. 6A (upper-right corner).

Individual parameters influence specific features in the PAID histograms (FIGS. 6B-6E). When occupancy increases 10-fold (FIG. 6B), the histogram becomes narrower along the monitor photon count axis (shown by opposing arrows), the correlation amplitude decreases 10-fold, and the long time count rate increases 10-fold (shown by arrow on the upperright). When the brightness increases 10-fold (FIG. 6C), the histogram shifts up in the log-log plot (as indicated by the arrows), and becomes narrower along the monitor photon axis. When the diffusion time increases 10-fold (FIG. 6D), the red and white contours are extended 10-fold along the time interval axis as well as the monitor photon count axis (shown by arrow). When a constant background with rate $k_{01}$=5 kHz is added (FIG. 6E), the correlation density decreases (since many start photons are now uncorrelated background photons), the background component is seen as an additional shallow slope (shown by the arrow) of the histogram to the right of the main correlation peak, and the total count rate is doubled (seen at long time intervals τ). In FIG. 6F, a second brighter species with $q_{21}$=$q_{11}$×4, $c_2$=0.006, $\tau_2^D$=100 µs, and $k_{01}$=0.765 kHz is added; these parameters were chosen so that the correlation curves corresponding to FIGS. 6A and 6F would overlap, demonstrating the limitations of FCS.

The advantages of PAID over FCS can be seen in FIG. 6G, which shows the autocorrelations for each of the simulations in FIGS. 6A-6F. In FCS, the occupancy is extracted from the correlation amplitude, which is $C_{SS}$(τ=0)=1+1/$c_1$ for a single diffusing species with no background (n FIG. 6A, $c_1$=0.1, so $C_{SS}$(τ=0)=11.0 for black curve). One FCS limitation is that both occupancy increases and background increases decrease the correlation amplitude [cf red curve ($c'_1$=10×$c_1$) and cyan curve (with $k_{01}$=5 kHz) in FIG. 6G]. In contrast, with PAID, they are distinguishable (FIGS. 6B and 6E). Another FCS limitation is that changes in molecular brightness do not affect the correlation curve [cf. black curve and dashed green curve ($q'_{11}=10\times q_{11}$) in FIG. 6F], preventing the ability to distinguish between components with different brightness (cf. overlap of magenta line and black line in FIG. 6G to difference between FIG. 6A and FIG. 6F). Again, the PAID histograms (FIGS. 6A and 6C) can clearly distinguish such changes.

Simulations-Quantitative Analysis of Stoichiometry Using Single-Channel PAID:

Despite the short time bin, there is an upward bias in the occupancies, along with a downward bias in the brightness due to species diffusion during the time bin. The magnitude of these biases can be estimated using the corrections for the apparent occupancy $c_{app}=c/\Gamma_{diff}$ and brightness $q_{app}=q\Gamma_{diff}$ used in FIMDA [32]. $\Gamma_{diff}$ is calculated for Gaussian detection volumes using $\beta=\omega^2/l^2=0.04$ and $t=\tau/\tau^D=0.2$. We obtain $\Gamma_{diff}=0.94$, which gives the expected values of $c_{app}=0.107$ and $q_{app}=47$ kHz, which match well with the values given in Table 1.

TABLE 1

Parameters Extracted using PAID, FIMDA, FCS, and FIDA fits for single-channel, one-component simulations in a Gaussian detection volume

| Parameters | Simulation | PAID | FIMDA | FCS | FIDA |
|---|---|---|---|---|---|
| Averaged Fits for 10 Simulations (30 s each): Low Occupancy | | | | | |
| $\chi^2$ | — | 1.2 ± 0.1 | 4.7 ± 0.2 | 1.3 ± 0.1 | 0.6 ± 0.1 |
| $k_{01}$ (kHz) | 0.0 | 0.01 ± 0.01 | 0.01 ± 0.01 | N/A | 0.02 ± 0.01 |
| $c_1$ (mol) | 0.1 | 0.100 ± 0.001 | 0.100 ± 0.001 | 0.099 ± 0.001 | 0.105 ± 0.001 |
| $\tau_1^D$ (μs) | 100.0 | 98 ± 1 | 99 ± 1 | 100 ± 1 | N/A |
| $q_{11}$ (kHz/mol) | 50.0 | 48.9 ± 0.3 | 49.7 ± 0.3 | N/A | 47.3 ± 0.3 |
| Averaged Fits for 10 Simulations (10 s each): Intermediate Occupancy | | | | | |
| $\chi^2$ | — | 1.0 ± 0.1 | 1.0 ± 0.1 | 1.0 ± 0.1 | 0.7 ± 0.1 |
| $k_{01}$ (kHz) | 0.0 | 0.03 ± 0.01 | 0.13 ± 0.03 | N/A | 0.3 ± 0.1 |
| $c_1$ (mol) | 1.0 | 0.99 ± 0.01 | 0.99 ± 0.01 | 0.99 ± 0.01 | 1.05 ± 0.01 |
| $\tau_1^D$ (μs) | 100.0 | 99 ± 1 | 94 ± 1 | 100 ± 1 | N/A |
| $q_{11}$ (kHz/mol) | 50.0 | 49.5 ± 0.2 | 50.8 ± 0.2 | N/A | 47.6 ± 0.2 |

Fixed values are in italics, fitted parameters are quoted with error estimates
Parameter values listed as N/A (not applicable) are not able to be extracted using the listed method.

Figure 7:
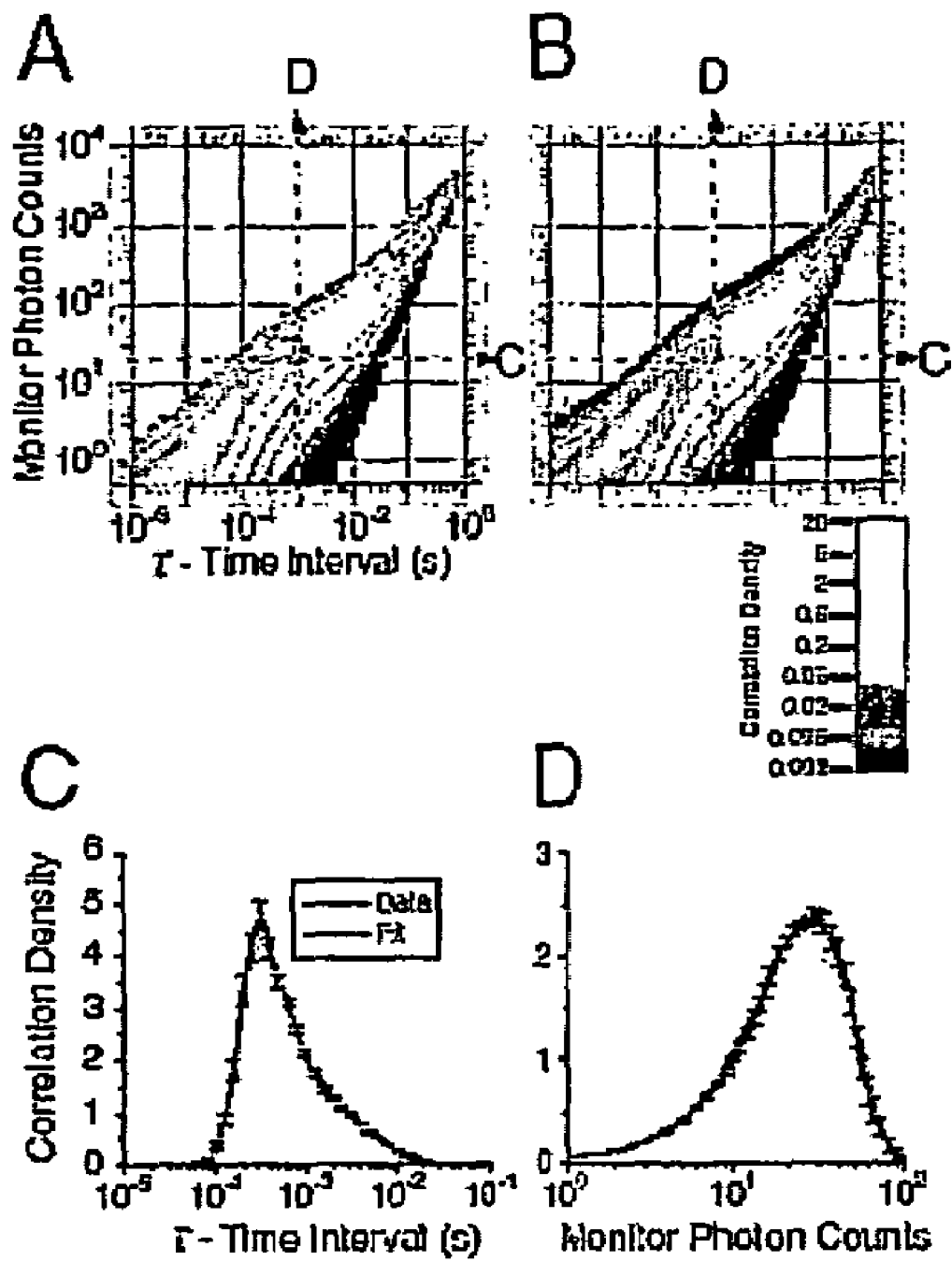
FIG. 7 shows an exemplary PAID fit from Table 1.

To demonstrate the ability of PAID to extract simultaneously occupancy, diffusion time, and brightness, and to compare it to FCS, FIDA/PCH, and FIMDA, we generated two series of single-channel (start=stop=monitor channel), single-component simulations in a Gaussian detection volume. The comparison of PAID with FIMDA is especially interesting, since both can simultaneously extract occupancy, diffusion, and brightness. These simulations provide comparisons between the methods under representative conditions where all methods have an appropriate model; we chose to use a Gaussian detection volume, ignoring triplet state induced fluctuations. FIDA and FIMDA, PCH, and PAID account for non-gaussian detection volumes differently, and PAID does not yet account for triplet state induced fluctuations. The low-occupancy series consists of 10 simulations with $c_1=0.1$, $\tau_1^D=100$ μs, $q_{11}=50$ kHz, and $k_{01}=0$ kHz. The intermediate-occupancy series is similar, but with $c_1=1.0$. PAID performed well in both series, with average error for each parameter<2% (Table 1); see FIG. 7 for a representative PAID fit for a low-occupancy simulation from Table 1. For low-occupancy simulations, FIMDA extracts values with accuracy similar to PAID, but with a significantly worse fit ($\chi^2\sim4$; mainly for time delay>diffusion time [66]). For the intermediate-occupancy simulations, the fits are good ($\chi^2\sim1$), and the extracted parameters are close to the simulation values (except for a 5% downward bias in the diffusion time). The accuracy of FCS-extracted parameters was similar to PAID and FIMDA. The errors of the FIDA-extracted parameters were similar to the errors found using the other methods. The time bin width used for the simulations was chosen to be ⅕ of the shortest diffusion time (20 μs), since FIDA assumes the molecules are stationary during the counting interval.

We also performed low-occupancy ($c_1=c_2=0.05$) and intermediate-occupancy ($c_1=c_2=0.5$ and $c_1=c_2=2.5$) simulations to test PAID for detection of stoichiometry in two-component experiments (Table 2). PAID performed well: low-occupancy simulations yielded low errors (1%-2%); intermediate-occupancy simulations ($c_1=c_2=0.5$) yielded somewhat higher errors (1%-8%), as well as biases up to 10% for the diffusion time and occupancy of the dimmer species. For somewhat higher occupancy ($c_1=c_2=2.5$), the quoted errors are still<10%, but the biases reach up to 20%. The errors and biases of the FIMDA-extracted parameters were in general similar to those extracted using PAID. However, for low-occupancy simulations, the occupancy biases were larger (~20%). For intermediate-occupancy simulations ($c_1=c_2=0.5$), occupancy biases were reduced, but the background count rate values were off by 25%. For the higher occupancy simulations ($c_1=c_2=2.5$), errors were in the range of 10-30%, with biases similar to PAID (up to 20%). The differences between PAID and FIMDA at low occupancy are primarily related to the models used, rather than the histograms used [66]. FCS fits with fixed brightness did not converge for either high- or low-occupancy simulations; significantly different results with the same $\chi^2$ were found with the same data set. This problem arises because FCS relies on diffusion time to detect the presence of subpopulations. If both occupancy and brightness are fixed, diffusion times can often be extracted, but with poorer accuracy than with PAID or FIMDA; since FIDA/PCH can (at best) fix the occupancies and brightnesses to their correct values, this demonstrates clearly that simultaneous fitting of FCS and FIDA/PCH cannot match the performance of PAID or FIMAD. The errors of the parameters extracted from the two-species simulations were larger for FIDA than for PAID or FIMDA.

TABLE 2

Parameters Extracted using PAID, FIMDA, FCS, and FIDA fits for single-channel, two-component simulations in a Gaussian detection volume

| Parameters | Simulation | PAID | FIMDA | FCS | FIDA |
|---|---|---|---|---|---|
| Averaged Fits for 10 Simulations (30 s each): Low Occupancy | | | | | |
| $\chi^2$ | — | 0.77 ± 0.04 | 1.1 ± 0.3 | 1.3 ± 0.2 | 0.5 ± 0.1 |
| $k_{01}$ (kHz) | 2.0 | 2.00 ± 0.01 | 1.90 ± 0.01 | 2.0 | 1.99 ± 0.03 |
| $c_1$ (mol) | 0.05 | 0.048 ± 0.001 | 0.064 ± 0.001 | 0.05 | 0.059 ± 0.002 |
| $\tau_1^D$ (µs) | 100.0 | 100 ± 2 | 117 ± 4 | 105 ± 7 | N/A |
| $q_{11}$ (kHz/mol) | 50.0 | 50 ± 1 | 51 ± 2 | 50.0 | 48 ± 2 |
| $c_2$ (mol) | 0.05 | 0.052 ± 0.001 | 0.042 ± 0.002 | 0.05 | 0.048 ± 0.003 |
| $\tau_2^D$ (µs) | 150.0 | 145 ± 2 | 146 ± 3 | 142 ± 3 | N/A |
| $q_{21}$ (kHz/mol) | 100.0 | 98 ± 1 | 106 ± 1 | 100.0 | 100 ± 2 |
| Averaged Fits for 10 Simulations (10 s each): Intermediate Occupancy | | | | | |
| $\chi^2$ | — | 0.9 ± 0.1 | 0.55 ± 0.02 | 1.4 ± 0.2 | 0.7 ± 0.1 |
| $k_{01}$ (kHz) | 2.0 | 2.03 ± 0.02 | 1.6 ± 0.2 | 2.0 | 1.6 ± 0.3 |
| $c_1$ (mol) | 0.5 | 0.45 ± 0.03 | 0.51 ± 0.04 | 0.5 | 0.57 ± 0.03 |
| $\tau_1^D$ (µs) | 100.0 | 88 ± 6 | 92 ± 5 | 120 ± 7 | N/A |
| $q_{11}$ (kHz/mol) | 50.0 | 53 ± 1 | 52 ± 2 | 50.0 | 46 ± 4 |
| $c_2$ (mol) | 0.5 | 0.53 ± 0.02 | 0.50 ± 0.04 | 0.5 | 0.52 ± 0.04 |
| $\tau_2^D$ (µs) | 150.0 | 153 ± 1 | 144 ± 4 | 141 ± 3 | N/A |
| $q_{21}$ (kHz/mol) | 100.0 | 96 ± 1 | 101 ± 2 | 100.0 | 97 ± 2 |
| $\chi^2$ | — | 0.63 ± 0.03 | 0.5 ± 0.1 | 0.5 ± 0.1 | 0.5 ± 0.1 |
| $k_{01}$ (kHz) | 2.0 | 2.3 ± 0.2 | 4 ± 2 | 2.0 | 0.4 ± 0.4 |
| $c_1$ (mol) | 2.5 | 2.8 ± 0.2 | 2.7 ± 0.3 | 2.5 | 3.0 ± 0.3 |
| $\tau_1^D$ (µs) | 100.0 | 110 ± 10 | 100 ± 30 | 127 ± 6 | N/A |
| $q_{11}$ (kHz/mol) | 50.0 | 55 ± 3 | 49 ± 2 | 50.0 | 50 ± 4 |
| $c_2$ (mol) | 2.5 | 2.1 ± 0.2 | 2.2 ± 0.2 | 2.5 | 2.2 ± 0.3 |
| $\tau_2^D$ (µs) | 150.0 | 150 ± 8 | 143 ± 5 | 136 ± 3 | N/A |
| $q_{21}$ (kHz/mol) | 100.0 | 101 ± 2 | 108 ± 3 | 100.0 | 102 ± 5 |

Experiments-Quantitative Analysis Using Single-Channel PAID:

Measurements were performed on DNA fragments to test the ability of PAID to detect subpopulations in solution based on the properties available in a single channel. Three samples were tested in the low-occupancy regime: 0.1 nM $DNA^{Cy3B,1T}$ only; 0.1 nM $DNA^{Cy3B,1T/Cy3B,65B}$ only; and a mixture of 0.05 nM $DNA^{Cy3B,1T}$ and 0.05 nM $DNA^{Cy3B,1T/Cy3B,65B}$ (Tables 34). Similarly, three samples were tested in the intermediate-occupancy regime: 1 nM $DNA^{Cy3B,1T}$ only; 1 nM $DNA^{Cy3B,1T/Cy3B,65B}$ only; and a mixture of 0.5 nM $DNA^{Cy3B,1T}$ and 0.5 nM $DNA^{Cy3B,1T/Cy3B65B}$ (Tables 3-4). For the fits of the one-species samples listed in Table 3, all parameters were fitted; the model fits well ($\chi^2$ in the range of 0.8-1.5). The important feature of the analysis is that the $DNA^{Cy3B,1T/Cy3B,65B}$ is ~2.1 times as bright as the $DNA^{Cy3B,1T}$ (Table 3), demonstrating the ability of PAID to evaluate stoichiometry; similar stoichiometry results are obtained using FCS in combination with the mean count rate. Based on the calculated detection volume, the occupancies of 1 nM and 0.1 nM samples are expected to be, respectively, 1.9 and 0.19. The occupancies extracted are within 30% of these values (errors attributed to pipetting errors and losses on surfaces). The measured diffusion times (620-760 µs) match well to the calculated diffusion time (710 µs). The measured background rates for three of the samples (0.2-0.4 kHz) are consistent with buffer-only measurements (0.24 kHz); the exception is the background in the intermediate-occupancy sample of $DNA^{Cy3B,1T/Cy3B,65B}$; however, the background makes up <1% of the signal.

TABLE 3

Parameters Extracted using single-component PAID fits for single-channel, single-species experiments

| Parameters | $DNA^{Cy3B,1T}$ | $DNA^{Cy3B,1T/Cy3B,65B}$ |
|---|---|---|
| Averaged Fits for 10 Measurements (30 s each): Low Occupancy | | |
| $\chi^2$ | 0.8 ± 0.1 | 1.2 ± 0.1 |
| $k_{01}$ (kHz) | 0.39 ± 0.03 | 0.37 ± 0.04 |
| $c_1$ (mol) | 0.19 ± 0.01 | 0.14 ± 0.01 |
| $\tau_1^D$ (µs) | 640 ± 20 | 760 ± 30 |
| $q_{11}$ (kHz/mol) | 9.9 ± 0.2 | 21.5 ± 0.7 |
| Averaged Fits for 10 Measurements (30 s each): Intermediate Occupancy | | |
| $\chi^2$ | 1.5 ± 0.1 | 1.2 ± 0.1 |
| $k_{01}$ (kHz) | 0.23 ± 0.04 | 2.2 ± 0.3 |
| $c_1$ (mol) | 2.21 ± 0.02 | 2.32 ± 0.04 |
| $\tau_1^D$ (µs) | 620 ± 10 | 650 ± 10 |
| $q_{11}$ (kHz/mol) | 8.7 ± 0.1 | 17.9 ± 0.2 |

Buffer-only measurements - $k_{01}$ = 0.24 ± 0.01 kHz

TABLE 4

Parameters Extracted using two-component PAID fits for single-channel, one- and two-species experiments

| Parameters | $DNA^{Cy3B,1T}$ Fixed ratio fit* | $DNA^{Cy3B,1T}$ Restricted fit† | $DNA^{Cy3B,1T/Cy3B,65B}$ Fixed ratio fit | $DNA^{Cy3B,1T/Cy3B,65B}$ Restricted fit | $DNA^{Cy3B,1T}$, $DNA^{Cy3B,1T/Cy3B,65B}$ Fixed ratio fit | $DNA^{Cy3B,1T}$, $DNA^{Cy3B,1T/Cy3B,65B}$ Restricted fit |
|---|---|---|---|---|---|---|
| Averaged Fits for 10 Measurements (30 s each): Low Occupancy | | | | | | |
| $\chi^2$ | 0.8 ± 0.1 | 1.9 ± 0.3 | 1.2 ± 0.1 | 2.3 ± 0.3 | 1.1 ± 0.1 | 1.9 ± 0.3 |
| $k_{01}$ (kHz) | 0.36 ± 0.02 | *0.24* | 0.35 ± 0.03 | *0.24* | 0.40 ± 0.02 | *0.24* |
| $c_1$ (mol) | 0.19 ± 0.01 | 0.210 ± 0.002 | 0.01 ± 0.01 | 0.01 ± 0.01 | 0.10 ± 0.02 | 0.130 ± 0.004 |
| $\tau_1^D$ (μs) | 680 ± 10 | *640* | 760 ± 20 | *640* | 760 ± 20 | *640* |
| $q_{11}$ (kHz/mol) | 9.7 ± 0.2 | *9.9* | 10.8 ± 0.3 | *9.9* | 9.6 ± 0.4 | *9.9* |
| $c_2$ (mol) | 0.01 ± 0.01 | 0.001 ± 0.001 | 0.14 ± 0.01 | 0.16 ± 0.01 | 0.08 ± 0.01 | 0.068 ± 0.003 |
| $\tau_2^D$ (μs) | 680 ± 10 | *640* | 760 ± 20 | *640* | 760 ± 20 | *640* |
| $q_{21}$ (kHz/mol) | 4.8 ± 0.1 | *19.9* | 21.6 ± 0.5 | *19.9* | 19.3 ± 0.8 | *19.9* |
| Averaged Fits for 10 Measurements (30 s each): Intermediate Occupancy | | | | | | |
| $\chi^2$ | 1.3 ± 0.1 | 1.6 ± 0.1 | 1.0 ± 0.1 | 1.3 ± 0.1 | 2.5 ± 0.1 | 2.8 ± 0.1 |
| $k_{01}$ (kHz) | 0.7 ± 0.1 | *0.24* | 0.5 ± 0.1 | *0.24* | 0.9 ± 0.1 | *0.24* |
| $c_1$ (mol) | 2.04 ± 0.04 | 2.19 ± 0.01 | 0.5 ± 0.1 | 0.2 ± 0.1 | 1.4 ± 0.1 | 1.99 ± 0.04 |
| $\tau_1^D$ (μs) | 640 ± 10 | *620* | 630 ± 10 | *620* | 680 ± 10 | *620* |
| $q_{11}$ (kHz/mol) | 9.0 ± 0.2 | *8.7* | 9.2 ± 0.1 | *8.7* | 7.4 ± 0.1 | *8.7* |
| $c_2$ (mol) | 0.10 ± 0.03 | 0.005 ± 0.002 | 2.1 ± 0.1 | 2.41 ± 0.04 | 1.0 ± 0.1 | 0.49 ± 0.03 |
| $\tau_2^D$ (μs) | 640 ± 10 | *620* | 630 ± 10 | *620* | 680 ± 10 | *620* |
| $q_{21}$ (kHz/mol) | 4.5 ± 0.1 | *17.4* | 18.5 ± 0.3 | *17.4* | 14.9 ± 0.3 | *17.4* |

*The ratio between the brightness of both components fixed to a factor of 2, and the diffusion times of the two components are linked.
†The brightness values are 1 and 2 times the values extracted from the $DNA^{Cy3B,1T}$ samples, and the diffusion times are fixed. The background rates were extracted from separate experiments.

PAID examples were performed using Cy3 (rather than Cy3B); in this case, the ratio in brightness between $DNA^{Cy3,1T/Cy3,65B}$ and $DNA^{Cy3,1T}$ was ~1.5 (data not shown). Even at low excitation intensities (<10 kW/cm$^2$), the factor of ~1.5 persisted, excluding triplet state saturation and photobleaching from the possible sources of the discrepancy. Using FCS, we observed a fluctuation that became faster with increasing excitation intensity without a corresponding change in the fluctuation amplitude (unlike triplet fluctuations). A similar effect was observed previously for Cy5, and was identified as photo-induced isomerization [67]. Since isomerization of two distinct fluorophores is uncorrelated, the amplitude of the fluctuation is reduced by a factor of 2 in the $DNA^{Cy3,1T/Cy3,65B}$, increasing the apparent concentration of the double-labeled species as compared to the single-labeled $DNA^{Cy3,1T}$, resulting in only a factor of ~1.5 difference in brightness. Using Cy3B, a conformationally-constrained analog of Cy3 which prevents isomerization, the fluctuation is absent. This emphasizes the importance of the choice of fluorophore when attempting to use brightness as a measure of stoichiometry. Dual-channel methods (discussed below) are less sensitive to such effects.

To determine if two species are present in a sample, it is necessary to perform two-component fits as well as one-component fits. Table 4 lists the results for two-component fits of the one- and two-species samples. For the "fixed ratio fit", the brightness of one species is fixed to be twice the brightness of the other, the total brightness can vary and the diffusion times of the two components are linked (set equal to each other). For the "restricted fit", only the occupancies are allowed to vary; the brightness values for the two components are set to be 1 and 2 times the brightness from the single-labeled species in Table 3, the diffusion times are taken from the same species, and the background is taken from separate, buffer-only measurements (not shown). For the single-species samples, only one component is fitted with a significant occupancy for most of the fits (ratio of occupancies>10:1); the only exception is the "fixed ratio fit" of the intermediate occupancy sample of $DNA^{Cy3B,1T/Cy3B,65B}$ (ratio is 4:1; however, the restricted fit has a ratio of 12:1). For the mixture samples, significant occupancies are fitted for both components for all of the fits. By dividing the single-species occupancies (extracted in Table 3) by 2, we obtain the expected occupancies for the mixture; the expected occupancies of $DNA^{Cy3B,1T}$ and $DNA^{Cy3B,1T/Cy3B,65B}$ are respectively 0.10 and 0.07 for the low-occupancy samples and 1.1 and 1.2 for the intermediate occupancy samples. The occupancies extracted from the low-occupancy mixture match the expected occupancies within 10% (except the lower brightness species is fit with a 30% higher occupancy with the restricted fit). The occupancies extracted from the intermediate occupancy mixture are biased toward the lower brightness species (identified with $DNA^{Cy3B,1T}$; 30% and 80% higher in the fixed ratio fit and restricted fit, respectively), decreasing the amount detected in the higher brightness species (identified with $DNA^{Cy3B,1T/Cy3B,65B}$; 20% lower and 50% lower in the fixed ratio fit and the restricted fit, respectively). These biases are most likely due to inadequate modeling of the detection volume; spurious components or biases are generally the result of imperfect overlap of model and data [68]. Improvements are expected upon measurement of the confocal detection volume and modeling of additional photophysical properties of fluorophores. Nevertheless, significant occupancies for two components were extracted in the mixtures, but not in the single-species samples; this demonstrates the capabilities of PAID to detect heterogeneity in single-channel experiments. For the fixed ratio fits, the diffusion times extracted (630-760 μs) match exactly the calculated value (710 μs). The brightness values are consistent with the values extracted from the single-component fits (all are within 15%).

Graphical representation of dual-channel experiments Using PAID: When applied to dual-channel examples the ability of PAID to extract brightness in multiple channels for each species becomes extremely important. Accordingly, the use of PAID for dual-channel systems is preferred. We use the example of a simple binding assay to illustrate what to expect when using PAID in dual-channel experiments. As illustrated in FIG. 1B, in a dual-color fluorescence binding assay, one molecule $A^y$ is labeled with a fluorophore of one color (for example "yellow", denoted y), while the second molecule $B^r$ is labeled with a fluorophore of a second color (for example "red", denoted r). Each fluorophore is excited by a distinct laser wavelength. Upon binding, there are three species present in solution: free $A^y$, free $B^r$, and complexes $A^yB^r$. The "yellow" and "red" fluorophores y and r have corresponding "yellow" and "red" detection channels, denoted, respectively, Y and R. Because of the vibronic tail of organic fluorophores toward the red end of their emission spectra, there is a small contribution from y into the channel R; the contribution from r into channel Y is typically negligible.

For each two-channel data set (from experiment or simulation), we performed a global fit of the series of all possible dual-channel PAID histograms, extracting brightness (in both channels), diffusion time, and occupancy for the species $A^yB^r$, $A^y$ and $B^r$. We write the channel assignments as a three letter code, STM, specifying the start, stop, and monitor channels (eg. the RYR PAID histogram uses S=R, T=Y, and M=R). For dual-channel experiments, there are 8 unique channel assignments for the PAID histogram: RRR, RRY, RYR, RYY, YRR, YRY, YYR, and YYY. The assignments of the start and stop channels (first two letters) select species of interest, which emit photons in both the start and stop channels. The choice of monitor channel determines the fluorophore which will be analyzed in terms of brightness using the PAID histogram. FIGS. 8A, 8D, 8G, and 8J show histograms for a dual-channel experiment if background, $A^y$, $B^r$, and $A^yB^r$ are present. FIGS. 8B, 8E, 8H, and 8K show the histograms if $A^yB^r$ is absent. The cartoons of the free molecules and complexes indicate which species contribute to any large correlation density peak. FIGS. 8C, 8F, 8I, and 8L compare vertical slices at time interval $\tau=1$ ms for the histograms in the presence and absence of $A^yB^r$.

Figure 8:
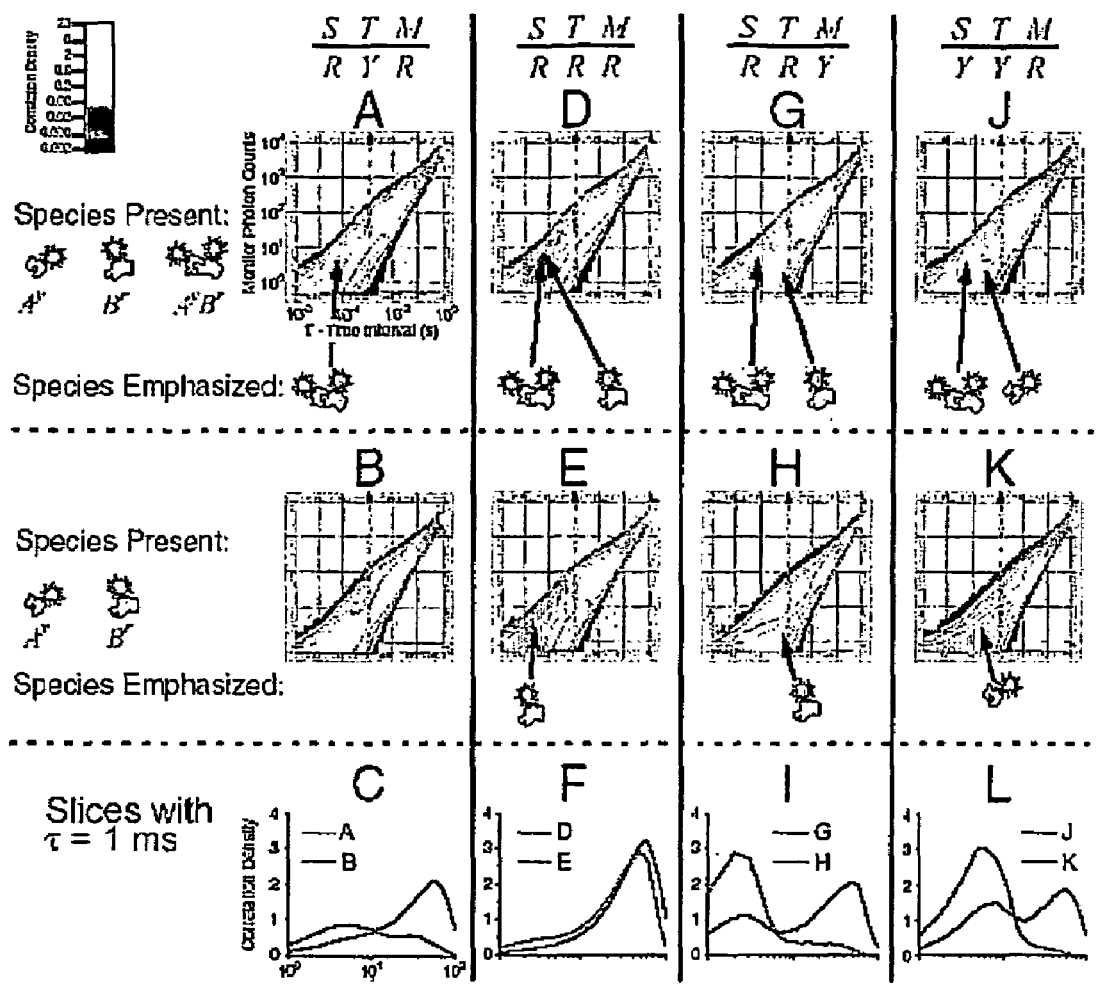
FIG. 8 shows dual-channel PAID histograms for simulations containing the species expected in an interaction study. Symbols r and y, red and yellow fluorophores, respectively. R and Y, red and yellow detector channels, respectively.

Taken together, the RYR, RYY, YRR, and YRY histograms determine the occupancy, diffusion time, and brightness in the Y and R channels of $A^yB^r$ (these are direct extensions of the cross-correlation functions used in FCCS). The histograms with S=R and T=emphasize time regions when $A^yB^r$ is present, since $A^yB^r$ emits photons in both R and Y whereas $A^y$ and $B^r$ emit only in one channel. Specifically, the RYR histogram monitors the brightness of r (FIG. 8A: RYR with $A^yB^r$ present; FIG. 8B: RYR with no $A^yB^r$). The correlation density peak in FIG. 8A corresponding to $A^yB^r$ (shown by arrow) is absent in FIG. 8B (the small correlation peak in FIG. 8B corresponds to the contribution of y into R). The RYY histogram (not shown) monitors the brightness of y, and is similar to RYR. The YRR and YRY histograms (not shown) are also similar to the RYR histogram in this case.

The histograms with S=R and T=R emphasize time regions where $B^r$ and $A^yB^r$ are present, since both emit photons in R. Specifically, for the RRR histogram, the correlation peaks from $B^r$ and $A^yB^r$ overlap since both have a similar brightness in R (FIGS. 8D-F). There is only one correlation peak visible, where $B^r$ and $A^yB^r$ both contribute (FIG. 8D, arrows), so the RRR histogram cannot distinguish well between $B^r$ and $A^yB^r$. However, for the RRY histogram, the correlation peaks from $B^r$ and $A^yB^r$ are well separated. $A^yB^r$ emits in Y (resulting in a correlation peak with high monitor photon count; left arrow), whereas $B^r$ does not emit in Y (resulting in a correlation peak with low monitor photon counts; right arrow) (FIGS. 8G and 8I). When $A^yB^r$ is absent, the corresponding correlation peak is noticeably absent, leaving only the correlation peak resulting from $B^r$ (FIGS. 8H and 8I). The YYY and YYR PAID histograms emphasize $A^y$ and $A^yB^r$ in a similar manner (FIG. 8J-L).

Figure 9:
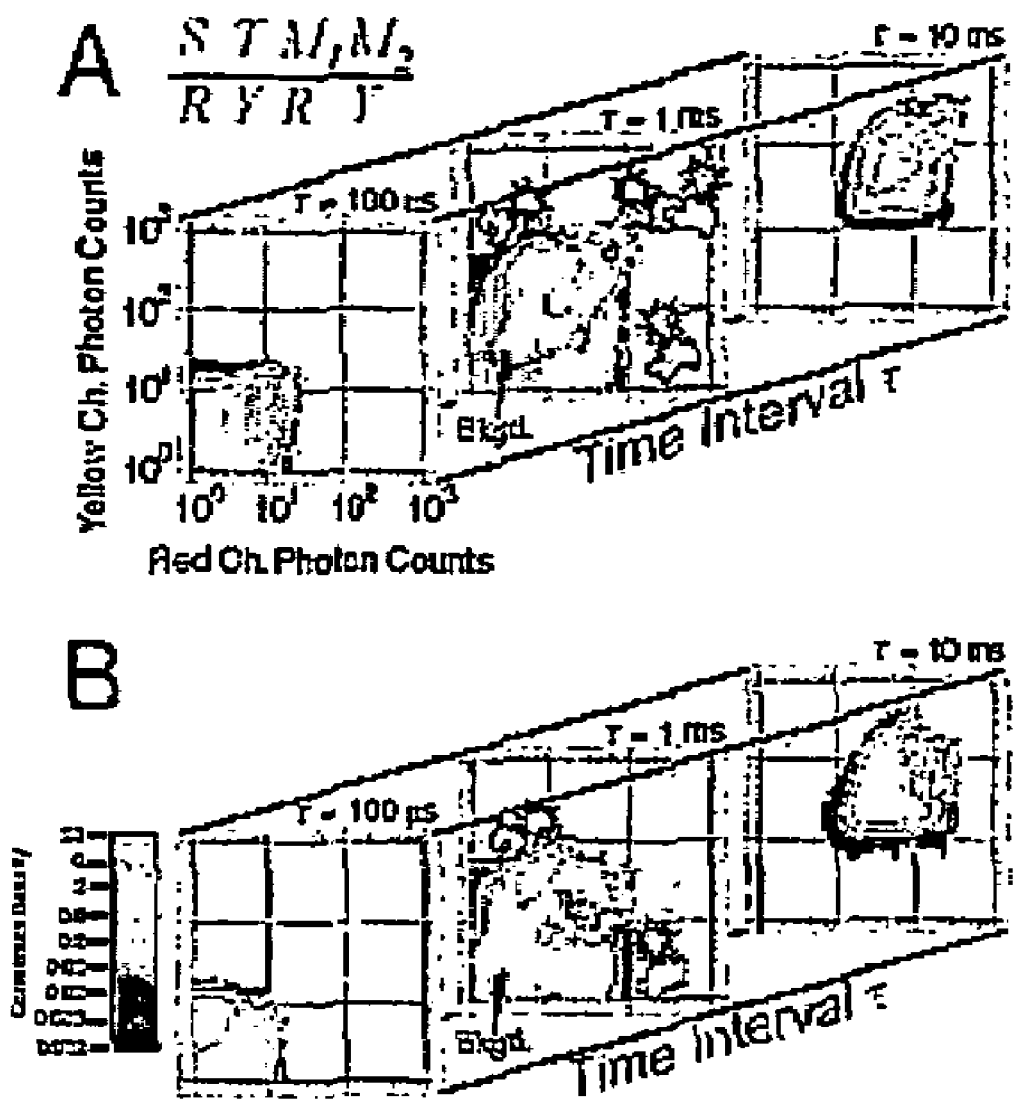
FIG. 9 shows two-channel, two monitor channel PAID histograms for the same simulations as in FIG. 8. The red channel is assigned as the start channel and the first monitor channel along the horizontal axis. The yellow channel is assigned as the stop channel and the second monitor channel along the vertical axis. Because the start and stop channels are assigned to different channels, these histograms emphasize the species that emits in both channels, the complex.

Higher sensitivity could be achieved if two monitor channels were used for the two-channel experiments, allowing the use of ratiometric information not available with a single monitor channel. Observables in single-molecule diffusion studies that depend on the ratio of two channels are more sensitive than brightness. A PAID histogram with two monitor channels has three axes: the time interval axis $\tau$, the number of photons in the red channel $n_R$, and the number of photons counted in the yellow channel $n_y$. FIG. 9A shows three slices of this histogram at different time intervals when $A^y$, $B^r$, and $A^yB^r$ are present, and FIG. 9B shows the same three slices when $A^yB^r$ is absent. The histograms shown are for the PAID histogram with the red channel assigned as the start channel (S=R), the yellow channel assigned as the stop channel (T=Y), and a monitor channel for each channel ($M_1$=R and $M_2$=Y). A cartoon of a particular type of molecule is placed in the $\tau=1$ ms slice at the approximate location where it contributes. The histograms in FIGS. 8A and 8B are the collapse of FIGS. 9A and 9B, respectively, summing along the yellow monitor channel axis, while keeping the time interval and red monitor channels axes. For an isolated burst, the number of photons counted depends on the diffusion path taken through the detection volume, whereas the ratio between two channels does not. For example, the correlation density peak in FIG. 9A at $\tau=1$ ms corresponding the complex is wider in the direction of the diagonal $n_R=n_y$ than in the perpendicular direction. The one monitor channel PAID histogram is a collapse of the two monitor channel histogram onto the Y or R axis. This collapse smears the central peak; the subpopulations of complex and free molecules are not clearly separated in the one monitor channel case, but are separated with two monitor channels (compare the $\tau=1$ ms slice in FIG. 9A with the corresponding single monitor channel histogram in FIG. 8A.) In view of these benefits, the fitting model can be extended to account for two monitor channels, if desired. The remainder of the examples will use only a single monitor channel.

Simulations-Quantitative Analysis of Binding Using Dual-Cannel PAID:

PAID and FCCS in dual-channel applications with two spectrally-separable fluorophores were investigated using multiple species simulations. The diffusion time of $A^yB^r$ was set to be 33% higher than $A^y$ and $B^r$; the brightness of each fluorophore was unchanged. As in the single-channel case, low- and intermediate-occupancy regimes were studied (Tables 5 and 6). The fluorophore y was set to have a total brightness of 50 kHz, 90% in channel Y and 10% in channel R. The fluorophore r was set to have a total brightness of 50 kHz, 100% in channel R. The background was set to $k_{OG}=k_{OR}=2$ kHz.

TABLE 5

Parameters Extracted using PAID and FCCS fits for two-channel, three-component simulations in a Gaussian detection volume at low occupancy

| Parameters | Simulation | PAID-Unrestricted Fit | PAID-Restricted Fit | FCCS |
|---|---|---|---|---|
| Averaged Fits for 10 Simulations (30 s each): Low Occupancy ||||
| $\chi^2$ | — | 0.72 ± 0.02 | 0.79 ± 0.02 | 0.95 ± 0.04 |
| $k_{OR}$ (kHz) | 2.0 | 2.00 ± 0.01 | 2.0 | 2.0 |
| $k_{OY}$ (kHz) | 2.0 | 2.00 ± 0.01 | 2.0 | 2.0 |

TABLE 5-continued

Parameters Extracted using PAID and FCCS fits for two-channel, three-component simulations in a Gaussian detection volume at low occupancy

| Parameters | Simulation | PAID-Unrestricted Fit | PAID-Restricted Fit | FCCS |
|---|---|---|---|---|
| $c_1$ (mol) | 0.05 | 0.049 ± 0.001 | 0.049 ± 0.001 | 0.050 ± 0.001 |
| $\tau_1^D$ (μs) | 300.0 | 287 ± 7 | 300.0 | 311 ± 4 |
| $q_{1R}$ (kHz/mol) | 50.0 | 50.3 ± 0.4 | 50.0 | 50.0 |
| $q_{1Y}$ (kHz/mol) | 0.0 | 0.05 ± 0.01 | 0.0 | 0.0 |
| $c_2$ (mol) | 0.05 | 0.049 ± 0.001 | 0.050 ± 0.001 | 0.050 ± 0.001 |
| $\tau_2^D$ (μs) | 300.0 | 294 ± 7 | 300.0 | 306 ± 4 |
| $q_{2R}$ (kHz/mol) | 5.0 | 4.8 ± 0.1 | 5.0 | 5.0 |
| $q_{2Y}$ (kHz/mol) | 45.0 | 44.8 ± 0.3 | 45.0 | 45.0 |
| $c_3$ (mol) | 0.05 | 0.050 ± 0.001 | 0.050 ± 0.001 | 0.051 ± 0.001 |
| $\tau_3^D$ (μs) | 400.0 | 394 ± 6 | 389 ± 7 | 404 ± 8 |
| $q_{3R}$ (kHz/mol) | 55.0 | 54.9 ± 0.3 | 55.2 ± 0.1 | 55.0 |
| $q_{3Y}$ (kHz/mol) | 45.0 | 44.7 ± 0.2 | 44.8 ± 0.1 | 45.0 |

Values that are fixed are shown in italics, with no errors listed.

TABLE 6

Parameters Extracted using PAID and FCCS fits for two-channel, three-component simulations in a Gaussian detection volume at intermediate occupancy

| Parameters | Simulation | PAID-Unrestricted Fit | PAID-Restricted Fit | FCCS |
|---|---|---|---|---|
| Averaged Fits for 10 Simulations (10 s each): Intermediate Occupancy | | | | |
| $\chi^2$ | — | 0.81 ± 0.02 | 0.90 ± 0.04 | 0.76 ± 0.09 |
| $k_{0R}$ (kHz) | 2.0 | 2.02 ± 0.02 | 2.0 | 2.0 |
| $k_{0Y}$ (kHz) | 2.0 | 2.00 ± 0.02 | 2.0 | 2.0 |
| $c_1$ (mol) | 0.5 | 0.50 ± 0.01 | 0.49 ± 0.01 | 0.050 ± 0.01 |
| $\tau_1^D$ (μs) | 300.0 | 320 ± 9 | 300.0 | 313 ± 3 |
| $q_{1R}$ (kHz/mol) | 50.0 | 49.1 ± 0.2 | 50.0 | 50.0 |
| $q_{1Y}$ (kHz/mol) | 0.0 | 0.06 ± 0.02 | 0.0 | 0.0 |
| $c_2$ (mol) | 0.5 | 0.49 ± 0.01 | 0.49 ± 0.01 | 0.50 ± 0.01 |
| $\tau_2^D$ (μs) | 300.0 | 306 ± 11 | 300.0 | 303 ± 7 |
| $q_{2R}$ (kHz/mol) | 5.0 | 4.9 ± 0.2 | 5.0 | 5.0 |
| $q_{2Y}$ (kHz/mol) | 45.0 | 44.5 ± 0.4 | 45.0 | 45.0 |
| $c_3$ (mol) | 0.5 | 0.50 ± 0.01 | 0.49 ± 0.01 | 0.49 ± 0.01 |
| $\tau_3^D$ (μs) | 400.0 | 395 ± 4 | 390 ± 6 | 407 ± 5 |
| $q_{3R}$ (kHz/mol) | 55.0 | 54.3 ± 0.4 | 55.0 ± 0.2 | 55.0 |
| $q_{3Y}$ (kHz/mol) | 45.0 | 44.5 ± 0.5 | 45.1 ± 0.2 | 45.0 |

For each simulation, three fits were performed The $1^{st}$ fit (Tables 5 and 6, $3^{rd}$ column) uses PAID with all parameters unrestricted The $2^{nd}$ fit (Tables 5 and 6, $4^{th}$ column) also uses PAID, with all parameters of the free components except for the occupancies being fixed. For the $1^{st}$ and $2^{nd}$ fits, all combinations of the dual-channel PAID histogram are fitted simultaneously; since each histogram emphasizes different species, parameters for all species can be extracted. The $3^{rd}$ fit (Tables 5 and 6, $5^{th}$ column) uses FCCS to simultaneously fit the autocorrelations of the red and yellow channels and the two cross-correlations, with all brightness and background values fixed.

The unrestricted fit extracted reliable values, within 1-10% for all parameters in both sets of simulations. Unexpectedly, fixing the brightness of the free components and the background resulted only in a modest improvement for the brightness values for the complex and no improvement for the diffusion time or for the occupancies. The parameters extracted using FCCS had similar statistical accuracy (~1% range) to those found using PAID. The extracted diffusion times are somewhat better with FGCS (the error bars were ~20% smaller), mainly due to the smaller numbers of fitted parameters (brightness and background were fixed to their simulation values; for experiments, it would be necessary to measure the brightness and background values using a method different than FCS.)

Experiments-quantitative analysis using dual-channel PAID: We performed measurements on fluorescently labeled DNA fragments to test the ability of dual-channel PAID to detect multiple species in solution and measure their properties, as is necessary for analysis of interactions. The fluorophores used in these experiments were Cy3 (as the "yellow" fluorophorey) and Cy5 (as the "red" fluorophore r). Based on the occupancies measured at higher concentration and the dilutions used, the occupancies for the intermediate-occupancy samples were expected to be 0.85±0.09 for DNA$^{Cy5,1T}$, 1.15±0.05 for DNA$^{Cy3,65B}$, and 0.84±0.03 for DNA$^{Cy5,1T/Cy3,65B}$. The fragments were prepared as free components and in the following mixtures: DNA$^{Cy5,1T}$/DNA$^{Cy3,65B}$ (to simulate non-interacting species); and DNA$^{Cy5,1T/Cy3,65B}$/DNA$^{Cy5,1T}$/DNA$^{Cy3,65B}$ (to simulate interacting species). The same samples were also prepared for 10-fold lower occupancies (low-occupancy samples). The value for DNA$^{Cy5,1T/Cy3,65B}$ was found by analyzing the Cy3 fluorescence, so the occupancy quoted includes DNA$^{Cy5,1T/Cy3,65B}$ and DNA$^{Cy5dark,1T/Cy3,65B}$ (with non-fluorescent Cy5—as seen in previous studies [12, 69]).

Figure 10:
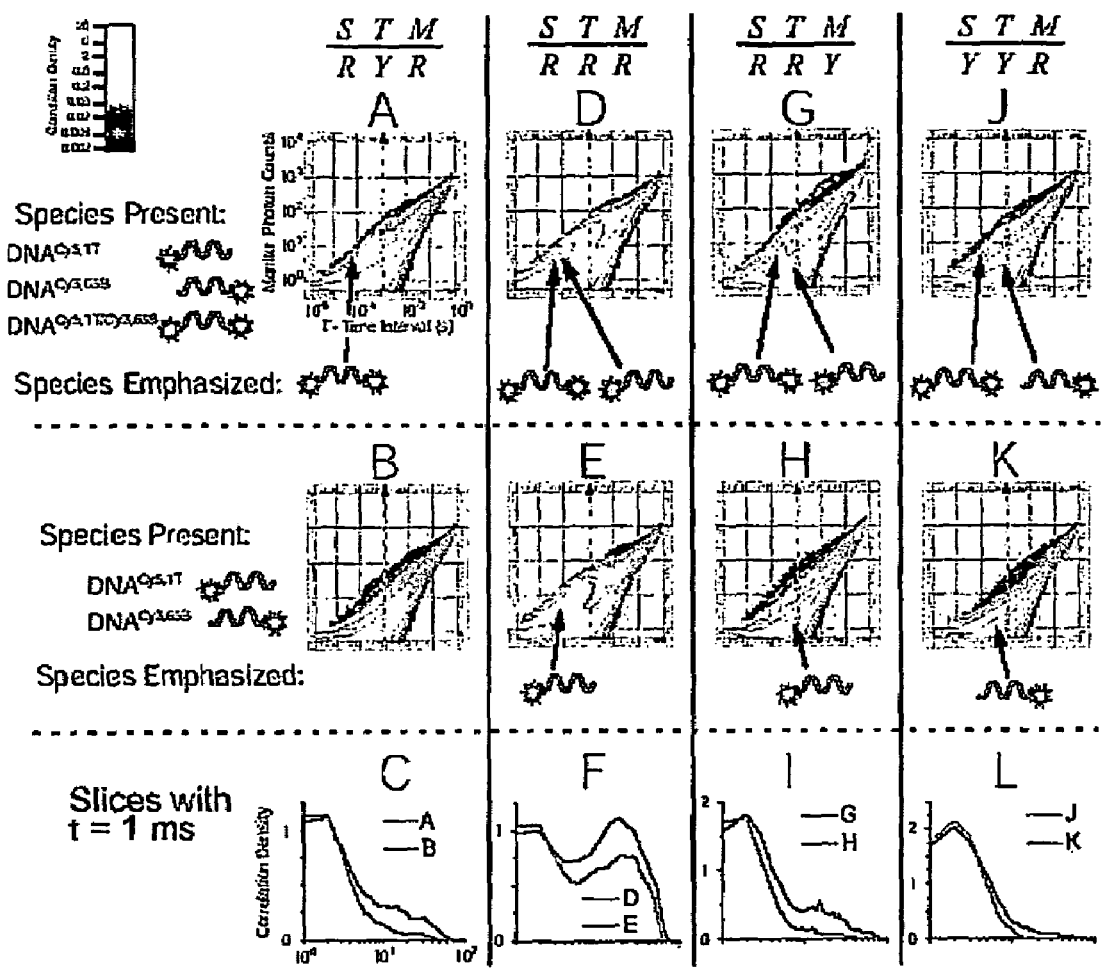
FIG. 10 shows dual-channel PAID histograms for samples containing species of labeled DNA fragments corresponding to those expected in an interaction study. The histograms chosen are the same as in FIGS. 8A, D, G, and J, are PAID histograms RYR, RRR, RRY, and YYR of a $DNA^{Cy5,1T}$, $DNA^{Cy3,65B}$, and $DNA^{Cy5,1T/Cy3,65B}$ mixture.

FIG. 10 shows how to visually detect the presence of the double-labeled DNA$^{Cy5,1T/Cy3,65B}$ using PAID histograms; two low-occupancy data sets are shown: DNA$^{Cy5,1T/Cy3,65B}$ / DNA$^{Cy5,1T}$/DNA$^{Cy3,65B}$ (FIGS. 10A, 10D, 10G, and 10J) and DNA$^{Cy5,1T}$/DNA$^{Cy3,65B}$ (FIGS. 10B, 10E, 10H, and 10K). FIGS. 10C, 10F, 10I, and 10L compare vertical slices at time interval τ=1 ms for the two data sets. By comparing the two sets of histograms, we can identify DNA$^{Cy5,1T/Cy3,65B}$. The RYR histogram (FIGS. 10A-C) emphasizes DNA$^{Cy5,1T/Cy3,65B}$; without DNA$^{Cy5,1T/Cy3,65B}$, the peak shown by the arrow in FIG. 10A disappears. The RRR histogram (FIGS. 10D-F) emphasizes DNA$^{Cy5,1T}$ and DNA$^{Cy5,1T/Cy3,65B}$, but does not distinguish well between these species since they both emit equally in R; absence of DNA$^{Cy5,1T/Cy3,65B}$ decreases amplitude of the correlation density peak (cf FIGS. 10D and 10E). The RRY histogram (FIGS. 10G-I) also emphasizes DNA$^{Cy5,1T}$ and DNA$^{Cy5,1T/Cy3,65B}$, but is able to distinguish between them since DNA$^{Cy5,1T}$ does not emit in Y whereas DNA$^{Cy5,1T/Cy3,65B}$ does. Finally, the YYR histogram (FIGS. 10J-L) emphasizes DNA$^{Cy3,65B}$ and DNA$^{Cy5,1T/Cy3,65B}$, separating them by their emission in R. In this case, because the occupancy of DNA$^{Cy3,65B}$ is higher than DNA$^{Cy5,1T/Cy3,65B}$, the peak corresponding to DNA$^{Cy5,1T/Cy3,65B}$ is less pronounced.

Using PAID, occupancy, diffusion time, and brightness was extracted from dual-channel experiments performed on single-species samples (Tables 7 and 8), then from dual-channel experiments performed on mixtures of those species (Tables 9 and 10). Consistency between the values extracted from fits of data from single species samples and values extracted from multiple-species fits of mixtures demonstrates the ability of PAID to analyze mixtures of species.

TABLE 7

Parameters extracted using PAID fits for two-channel, single-species, low occupancy experiments

| Parameters | DNA$^{Cy5,1T}$ | DNA$^{Cy3,65B}$ | DNA$^{Cy5,1T/Cy3,65B}$ |
|---|---|---|---|
| *Fit for 1 Measurement\* (300 s): Low occupancy* | | | |
| $\chi^2$ | 9.3 ± 0.2 | 5.5 ± 0.1 | 1.9 ± 0.3 |
| $k_{0R}$ (kHz) | 0.82 ± 0.01 | 0.76 ± 0.01 | 0.68 ± 0.01 |
| $k_{0Y}$ (kHz) | 1.30 ± 0.01 | 1.14 ± 0.03 | 0.95 ± 0.01 |
| DNA Fragment 1 | DNA$^{Cy5,1T}$ | DNA$^{Cy3,65B}$ | DNA$^{Cy5dark,1T/Cy3,65B}$ |
| $c_1$ (mol) | 0.022 ± 0.001 | 0.073 ± 0.003 | 0.023 ± 0.003 |
| $\tau_1^D$ (µs) | 430 ± 10 | 570 ± 10 | 670 ± 60 |
| $q_{1R}$ (kHz/mol) | 12.0 ± 0.1 | 0.94 ± 0.03 | 0.8 ± 0.1 |
| $q_{1Y}$ (kHz/mol) | 0.02 ± 0.01 | 10.0 ± 0.3 | 9.2 ± 0.8 |
| DNA Fragment 2 | None | None | DNA$^{Cy5,1T/Cy3,65B}$ |
| $c_2$ (mol) | | | 0.012 ± 0.001 |
| $\tau_2^D$ (µs) | | | 650 ± 10 |
| $q_{2R}$ (kHz/mol) | | | 6.8 ± 0.3 |
| $q_{2Y}$ (kHz/mol) | | | 6.7 ± 0.3 |

*All 300 s of low occupancy data fit at once to improve statistics.

TABLE 8

Parameters extracted using PAID fits for two-channel, single-species, intermediate occupancy experiments

| Parameters | DNA$^{Cy5,1T}$ | DNA$^{Cy3,65B}$ | DNA$^{Cy5,1T/Cy3,65B}$ |
|---|---|---|---|
| *Averaged Fits for 10 Measurements (30 s): Intermediate occupancy* | | | |
| $\chi^2$ | 4.7 ± 0.2 | 2.2 ± 0.1 | 1.4 ± 0.1 |
| $k_{0R}$ (kHz) | 1.30 ± 0.01 | 0.99 ± 0.01 | 0.92 ± 0.01 |
| $k_{0Y}$ (kHz) | 1.33 ± 0.01 | 1.44 ± 0.01 | 1.29 ± 0.01 |
| DNA Fragment 1 | DNA$^{Cy5,1T}$ | DNA$^{Cy3,65B}$ | DNA$^{Cy5dark,1T/Cy3,65B}$ |
| $c_1$ (mol) | 0.68 ± 0.01 | 1.08 ± 0.01 | 0.32 ± 0.01 |
| $\tau_1^D$ (µs) | 390 ± 10 | 550 ± 20 | 700 ± 10 |
| $q_{1R}$ (kHz/mol) | 9.4 ± 0.2 | 0.82 ± 0.01 | 0.70 ± 0.03 |
| $q_{1Y}$ (kHz/mol) | 0.02 ± 0.01 | 9.0 ± 0.1 | 10.7 ± 0.2 |
| DNA Fragment 2 | None | None | DNA$^{Cy5,1T/Cy3,65B}$ |
| $c_2$ (mol) | | | 0.24 ± 0.01 |
| $\tau_2^D$ (µs) | | | 580 ± 10 |
| $q_{2R}$ (kHz/mol) | | | 7.6 ± 0.1 |
| $q_{2Y}$ (kHz/mol) | | | 7.6 ± 0.2 |

TABLE 9

Parameters extracted using PAID fits for two-channel, multiple-species, low occupancy experiments

| Parameters | DNA$^{Cy3,65B}$, DNA$^{Cy5,1T}$ Unrestricted 2 component | DNA$^{Cy3,65B}$, DNA$^{Cy5,1T}$ Restricted 3 component | DNA$^{Cy3,65B}$, DNA$^{Cy5,1T}$, DNA$^{Cy5,1T/Cy3,65B}$ Unrestricted 3 component | DNA$^{Cy3,65B}$, DNA$^{Cy5,1T}$, DNA$^{Cy5,1T/Cy3,65B}$ Restricted 3 component |
|---|---|---|---|---|
| *Fit for 1 Measurement (300 s): Low occupancy* | | | | |
| $\chi^2$ | 2.8 ± 0.2 | 3.5 ± 0.1 | 2.3 ± 0.4 | 3.9 ± 0.1 |
| $k_{0R}$ (kHz) | 0.87 ± 0.01 | 0.88 ± 0.01 | 0.80 ± 0.01 | 0.78 ± 0.01 |
| $k_{0Y}$ (kHz) | 1.04 ± 0.01 | 1.04 ± 0.01 | 1.12 ± 0.01 | 1.08 ± 0.01 |
| DNA Fragment 1 | DNA$^{Cy5,1T}$ | DNA$^{Cy5,1T}$ | DNA$^{Cy5,1T}$ | DNA$^{Cy5,1T}$ |
| $c_1$ (mol) | 0.018 ± 0.001 | 0.016 ± 0.001 | 0.011 ± 0.001 | 0.016 ± 0.001 |
| $\tau_1^D$ (µs) | 430 ± 10 | *430* | 360 ± 10 | *420* |
| $q_{1R}$ (kHz/mol) | 11.0 ± 0.2 | *12.0* | 15.4 ± 0.4 | *12.5* |
| $q_{1Y}$ (kHz/mol) | 0.01 ± 0.02 | *0.02* | 0.02 ± 0.03 | *0.0* |
| DNA Fragment 2 | DNA$^{Cy3,65B}$ | DNA$^{Cy3,65B}$ | DNA$^{Cy3,65B}$* | DNA$^{Cy3,65B}$* |
| $c_2$ (mol) | 0.068 ± 0.001 | 0.067 ± 0.001 | 0.077 ± 0.003 | 0.088 ± 0.001 |
| $\tau_2^D$ (µs) | 530 ± 10 | *570* | 570 ± 10 | *570* |
| $q_{2R}$ (kHz/mol) | 0.95 ± 0.02 | *0.94* | 0.89 ± 0.02 | *0.94* |
| $q_{2Y}$ (kHz/mol) | 10.2 ± 0.1 | *10.0* | 1.12 ± 0.3 | *10.0* |
| DNA Fragment 3 | None | DNA$^{Cy5,1T/Cy3,65B}$ | DNA$^{Cy5,1T/Cy3,65B}$ | DNA$^{Cy5,1T/Cy3,65B}$ |
| $c_3$ (mol) | | 0.0001 ± 0.0001 | 0.015 ± 0.002 | 0.013 ± 0.001 |
| $\tau_3^D$ (µs) | | *650* | 680 ± 40 | *650* |
| $q_{3R}$ (kHz/mol) | | *6.8* | 7.3 ± 0.7 | *6.8* |
| $q_{3Y}$ (kHz/mol) | | *6.7* | 6.8 ± 0.3 | *6.7* |

*Includes contributions from DNA$^{Cy5dark,1T/Cy3,65B}$

TABLE 10

Parameters extracted using PAID fits for two-channel, multiple-species, intermediate occupancy experiments

| Parameters | $DNA^{Cy3,65B}$, $DNA^{Cy5,1T}$ Unrestricted 2 component | $DNA^{Cy3,65B}$, $DNA^{Cy5,1T}$ Restricted 3 component | $DNA^{Cy3,65B}$, $DNA^{Cy5,1T}$, $DNA^{Cy5,1T/Cy3,65B}$, Unrestricted 3 component | $DNA^{Cy3,65B}$, $DNA^{Cy5,1T}$, $DNA^{Cy5,1T/Cy3,65B}$, Restricted 3 component |
|---|---|---|---|---|
| Averaged Fits for 10 Measurements (30 s each): Intermediate occupancy | | | | |
| $\chi^2$ | 1.8 ± 0.1 | 3.0 ± 0.2 | 3.0 ± 0.1 | 4.8 ± 0.2 |
| $k_{OR}$ (kHz) | 1.4 ± 0.1 | 0.71 | 1.66 ± 0.01 | 0.71 |
| $k_{OY}$ (kHz) | 1.44 ± 0.01 | 1.15 | 1.3 ± 0.1 | 1.15 |
| DNA Fragment 1 | $DNA^{Cy5,1T}$ | $DNA^{Cy5,1T}$ | $DNA^{Cy5,1T}$ | $DNA^{Cy5,1T}$ |
| $c_1$ (mol) | 0.43 ± 0.01 | 0.57 ± 0.01 | 0.37 ± 0.01 | 0.74 ± 0.01 |
| $\tau_1^D$ (µs) | 350 ± 10 | 389 | 360 ± 10 | 389 |
| $q_{1R}$ (kHz/mol) | 11.0 ± 0.1 | 9.4 | 14.5 ± 0.4 | 9.4 |
| $q_{1Y}$ (kHz/mol) | 0.20 ± 0.03 | 0.02 | 0.3 ± 0.1 | 0.02 |
| DNA Fragment 2 | $DNA^{Cy3,65B}$ | $DNA^{Cy3,65B}$ | $DNA^{Cy3,65B}$* | $DNA^{Cy3,65B}$* |
| $c_2$ (mol) | 0.86 ± 0.01 | 0.96 ± 0.01 | 1.0 ± 0.1 | 1.56 ± 0.01 |
| $\tau_2^D$ (µs) | 560 ± 10 | 554 | 500 ± 10 | 554 |
| $q_{2R}$ (kHz/mol) | 0.75 ± 0.02 | 0.82 | 0.5 ± 0.1 | 0.82 |
| $q_{2Y}$ (kHz/mol) | 9.8 ± 0.1 | 9.0 | 11.5 ± 0.3 | 9.0 |
| DNA Fragment 3 | None | $DNA^{Cy5,1T/Cy3,65B}$ | $DNA^{Cy5,1T/Cy3,65B}$ | $DNA^{Cy5,1T/Cy3,65B}$ |
| $c_3$ (mol) | | 0.01 ± 0.01 | 0.58 ± 0.05 | 0.22 ± 0.01 |
| $\tau_3^D$ (µs) | | 575 | 450 ± 10 | 575 |
| $q_{3R}$ (kHz/mol) | | 7.6 | 5.3 ± 0.4 | 7.6 |
| $q_{3Y}$ (kHz/mol) | | 7.6 | 6.4 ± 0.1 | 7.6 |

*Includes contributions from $DNA^{Cy5dark,1T/Cy3,65B}$

Figure 11:
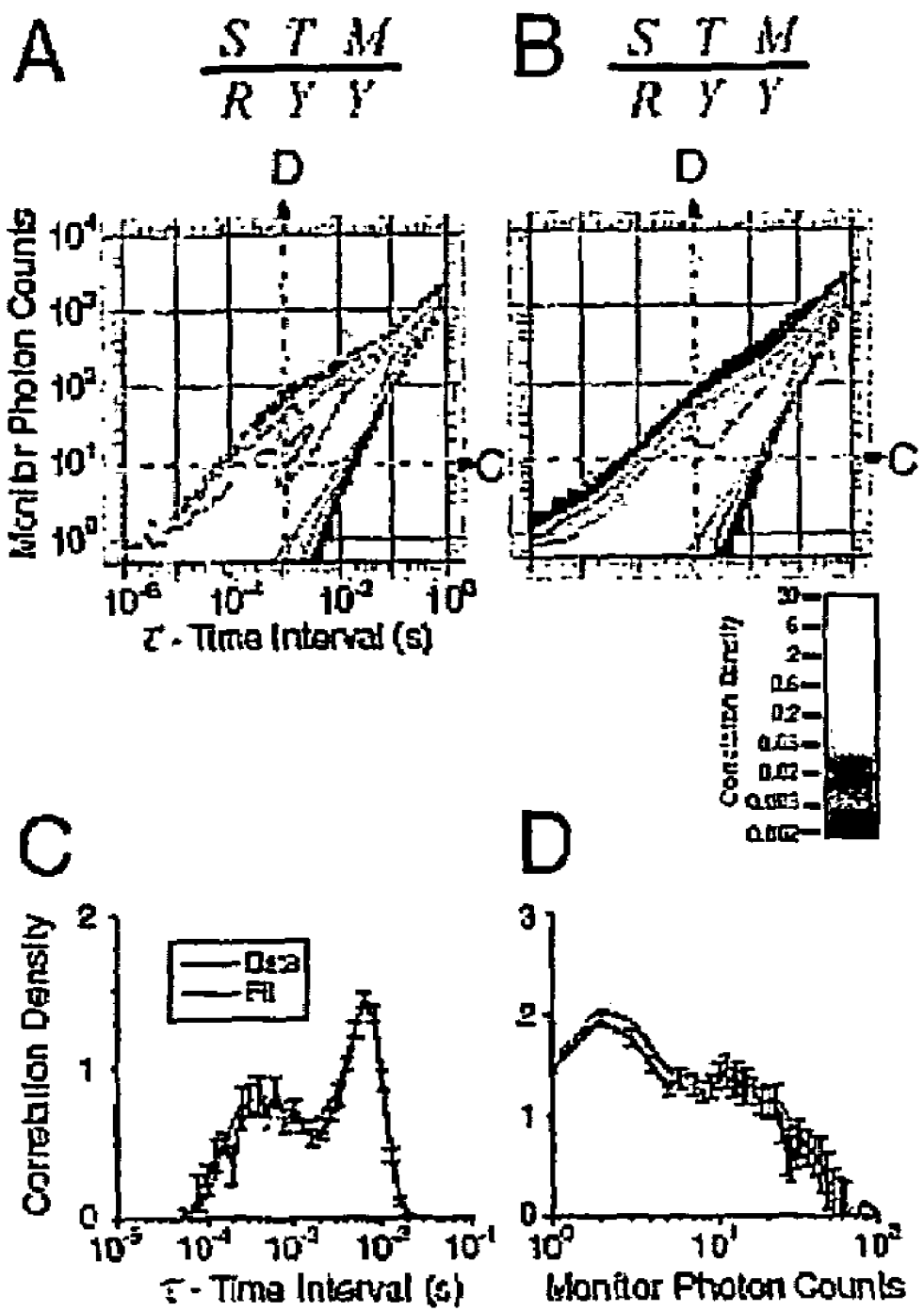
FIG. 11 shows PAID histograms with STM=RYY and fit (Table 9).

FIG. 11 shows a representative fit of the RYY histogram (emphasizing $DNA^{Cy5,1T/Cy3,65B}$) for the low-occupancy mixture sample (Table 9); this is one of the eight histograms fitted simultaneously over time intervals between 10 µs and 1 s. The peak toward higher photon counts in the vertical slice is caused by $DNA^{Cy5,1T/Cy3,65B}$. The fit is generally within the error bars, and follows the data to within 10%.

As shown in Tables 7-10, we obtained fits with $\chi^2$ in the range $10 > \chi^2 > 1$ (ideally $\chi^2 = 1$). The quality of the fits is sufficient to extract values with generally excellent accuracy and consistency, but the deviations indicated by the higher $\chi^2$ give rise to biases in certain values (see below). The deviations between model and fit can be attributed to two general sources. First, many photophysical properties of the fluorophores are not yet modeled in PAID, such as triplet state fluctuations and fluorescence saturation [15], photobleaching [16, 70], and photo-induced isomerization [67]. Although time intervals less than 10 µs are excluded from the fit to minimize photophysical effects, these properties still affect fitted values. Second, deviations of the experimental detection volume from the modeled volume may also play a role in the increased $\chi^2$ [68]. The model used for the fits in Tables 7-10 was based on a non-Gaussian detection volume; using a simpler Gaussian detection volume, significantly higher $\chi^2$ values are found. For example, fitting the $DNA^{Cy3,65B}$ data resulted in fits with $\chi^2 = 13.1$ and $\chi^2 = 32.5$ for the low-occupancy and intermediate-occupancy data sets, respectively; the non-Gaussian volume yielded $\chi^2 = 5.5$ and $\chi^2 = 2.2$ respectively. This highlights the critical role of detection volume for the model, and indicates that further improvement may be possible.

Tables 7 and 8 show fitted values for the samples containing only one species of labeled DNA, where the background rates, occupancies, diffusion times, and brightness in each channel were fitted parameters. To fit the data for $DNA^{Cy5,1T/Cy3,65B}$, two components were necessary, one with Cy3-only and another with Cy3 and Cy5. This is due to non-fluorescent Cy5; single-species fits and inspection of time traces both indicate the presence of a species emitting only in Cy3 channel [12, 69]. When parameters corresponding to $DNA^{Cy5,1T}$ were added to check if there was a species with non-emitting Cy3 (restricted to fit emission only in R), there was only a small occupancy fitted (~0.001, not shown). For the single-species, low-occupancy data (Table 7), the extracted occupancies were 35%-70% lower than expected from higher-concentration FCS experiments, whereas for the single-species, intermediate-occupancy data (Table 8), they are 4%-20% lower than expected (note: for $DNA^{Cy5,1T/Cy3,65B}$, the occupancies for $DNA^{Cy5,1T/Cy3,65B}$ and $DNA^{Cy5dark,1T/Cy3,65B}$ are added). The difference between extracted and estimated occupancies can be attributed to loss of DNA on surfaces during handling. The diffusion times extracted for $DNA^{Cy5,1T/Cy3,65B}$ and $DNA^{Cy3,65B}$ are similar to the theoretical ones (550-700 µs vs. 710 µs); diffusion times for $DNA^{Cy5,1T}$ are shorter (~400 µs), largely due to the effects of photo-induced isomerization [67], although photobleaching of Cy5 within the detection volume and triplet state fluctuations may play a role. The brightness values extracted are similar to what was found earlier in the single-channel experiments.

We performed two fits for mixtures of DNA fragments simulating non-interacting and interacting species (Tables 9-10). The $1^{st}$ assumes the correct number of species, but allows all parameters to freely vary; the $2^{nd}$ fit uses the single-species parameters already extracted to restrict the parameters for the free components, except for occupancy. These fits show that a sample with two species can be distinguished from a sample with three species, as is necessary for measuring interactions. In Tables 9 and 10, PAID performed extremely well in all the restricted fits and in three of the four unrestricted fits. Although the three-component, unrestricted fit at intermediate occupancy identified three species, it produced values less consistent with values obtained with other fits.

The restricted fits in Table 10 fix the background rates to values obtained from buffer-only measurements. The fits in Table 9 allow the background rates to freely vary since, under low-occupancy conditions, contributions from the background photons to the PAID histograms are well-separated from contributions from the DNA species (when the background values are fixed to those used in the restricted fits in Table 10, small variations in background between measurements cause $\chi^2$ to be as high as 40). The occupancies extracted from the mixtures using restricted fits were consistent with the occupancies extracted from the single-species samples (within 15%, except for $DNA^{Cy5,1T}$ at low occupancy, which is 27% lower).

For the unrestricted low-occupancy data fits in Table 9, the occupancies extracted for $DNA^{Cy3,65B}$ and $DNA^{Cy5,1T/Cy3,65B}$ are consistent with the values obtained using the restricted fits (typically within 10%). However, the occupancy extracted for $DNA^{Cy5,1T}$ in the three species sample is smaller (30%), with compensating increases in the brightness extracted in R. For the unrestricted intermediate-occupancy fits in Table 10, the occupancies for $DNA^{Cy5,1T}$ were smaller (25%-50%), with compensating increases in the brightness in R. The occupancies extracted using the unrestricted fit from $DNA^{Cy3,65B}$ and $DNA^{Cy5,1T/Cy3,65B}$ in the three-fragment mixture are different from those obtained with the restricted fit (a 33% decrease and a 160% increase). With the unrestricted fits, the diffusion times extracted for $DNA^{Cy5,1T/Cy3,65B}$ and $DNA^{Cy3,65B}$ are similar to the theoretical one (500-700 µs vs. 710 µs). The diffusion times for $DNA^{Cy5,1T}$ are shorter (~400 µs). The consistency found for brightness is excellent for all fits (typically ~10%).

The effects of triplet state fluctuations and fluorescence saturation [15], photobleaching [16, 70], and photo-induced isomerization [67] are well-characterized in FCS; many of these features are evident in the data analyzed here. To compare with results using PAID, the data from Tables 8 and 10 were analyzed using FCS over the same range of time intervals, modeling only diffusion (not shown). Variations in diffusion time that correlated with those in Table 8 and 10 were found, indicating that the photophysical properties that affect FCS have similar effects on PAID. Improvement of accuracy and consistency of fitted values is expected when these effects are incorporated into the PAID model.

Analysis of RNA Polymerase—DNA Interactions:

PAID was used to study the formation of RNA polymerase complexes with DNA, and to show that PAID can resolve and quantitate species with differences in brightness and/or diffusion time. DNA was labeled with Cy5 (as the "red" fluorophore r) to yield $DNA^{Cy5,65B}$; RNAP was labeled with TMR (as the "yellow" fluorophore y) on the a subunit to yield $R\sigma^{TMR}$. In the $R\sigma^{TMR}$-$DNA^{Cy5}$ complex, the distance between TMR and Cy5 is >>100 Å, excluding interactions between the fluorophores [57]. We examined free $DNA^{Cy5}$, free $R\sigma^{TMR}$, and an interaction mixture that contains the $R\sigma^{TMR}$-$DNA^{Cy5,65B}$ complex along with free species ("RNAP+DNA" sample; Table 11). PAID analysis of $DNA^{Cy5,65B}$ recovered brightness and diffusion times similar to ones of the previous DNA fragments (8.9 kHz vs. 9.4-10.2 kHz, and 440 µs vs. ~400 µs, respectively). Analysis of $R\sigma^{TMR}$ recovered brightness of ~10 kHz, while the diffusion time of ~710 µs was larger than that of $DNA^{Cy5}$, but smaller than the theoretical value (~1 ms; Materials and Methods). In addition to possible causes for deviation mentioned in the previous section, the smaller value may also be due to imperfect modeling of the hydrodynamic radius of the protein.

Figure 12:
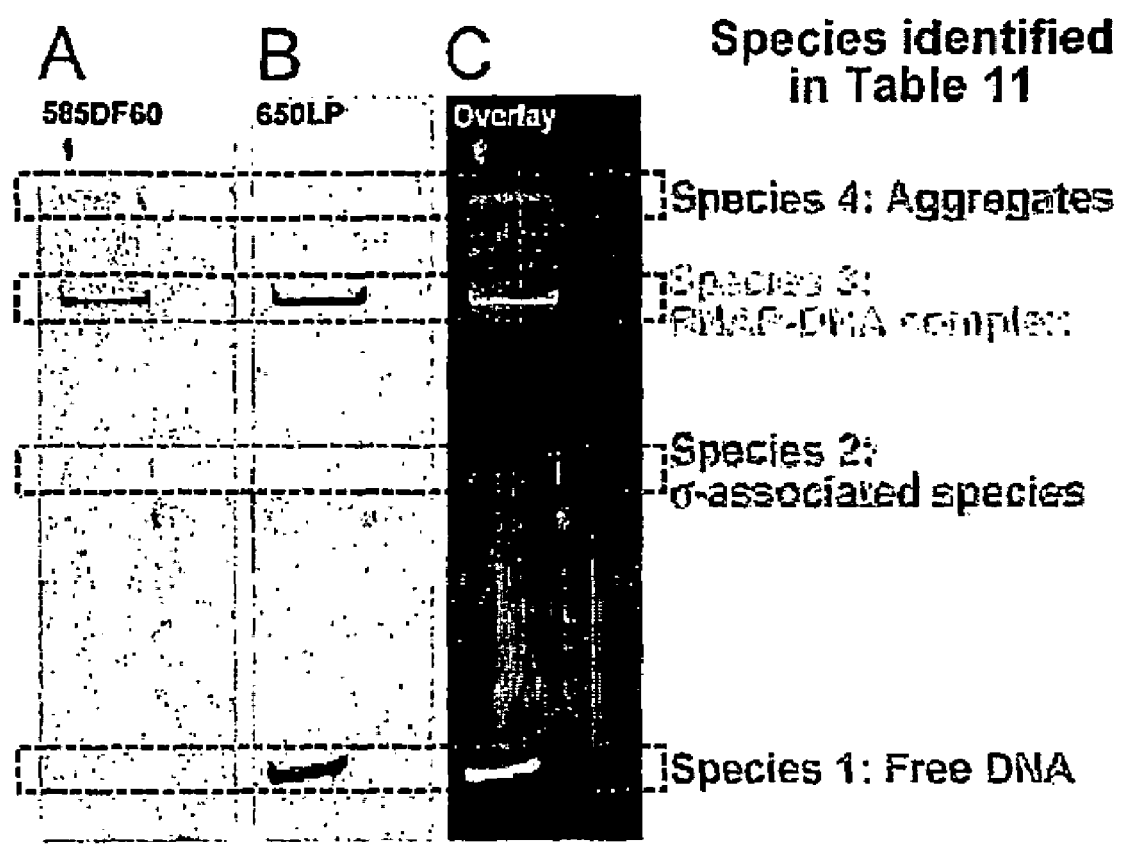
FIG. 12 shows fluorescence-based gel images showing the major species present in RNAP+DNA samples. Image A shows species with TMR-based signals (532 excitation, 585BP60 emission); species identified as aggregates (found in the wells of the gel), RNAP-DNA complex and a-associated species are visible. Image B shows species with Cy5-based signals (633 excitation, 650LP emission); species identified as RNAP-DNA complex and DNA are visible. Image C shows an overlay of images A (green color) and B (red color); coincidence of red and green signal is shown as orange. The only species showing coincidence is the RNAP-DNA complex.
Figure 13:
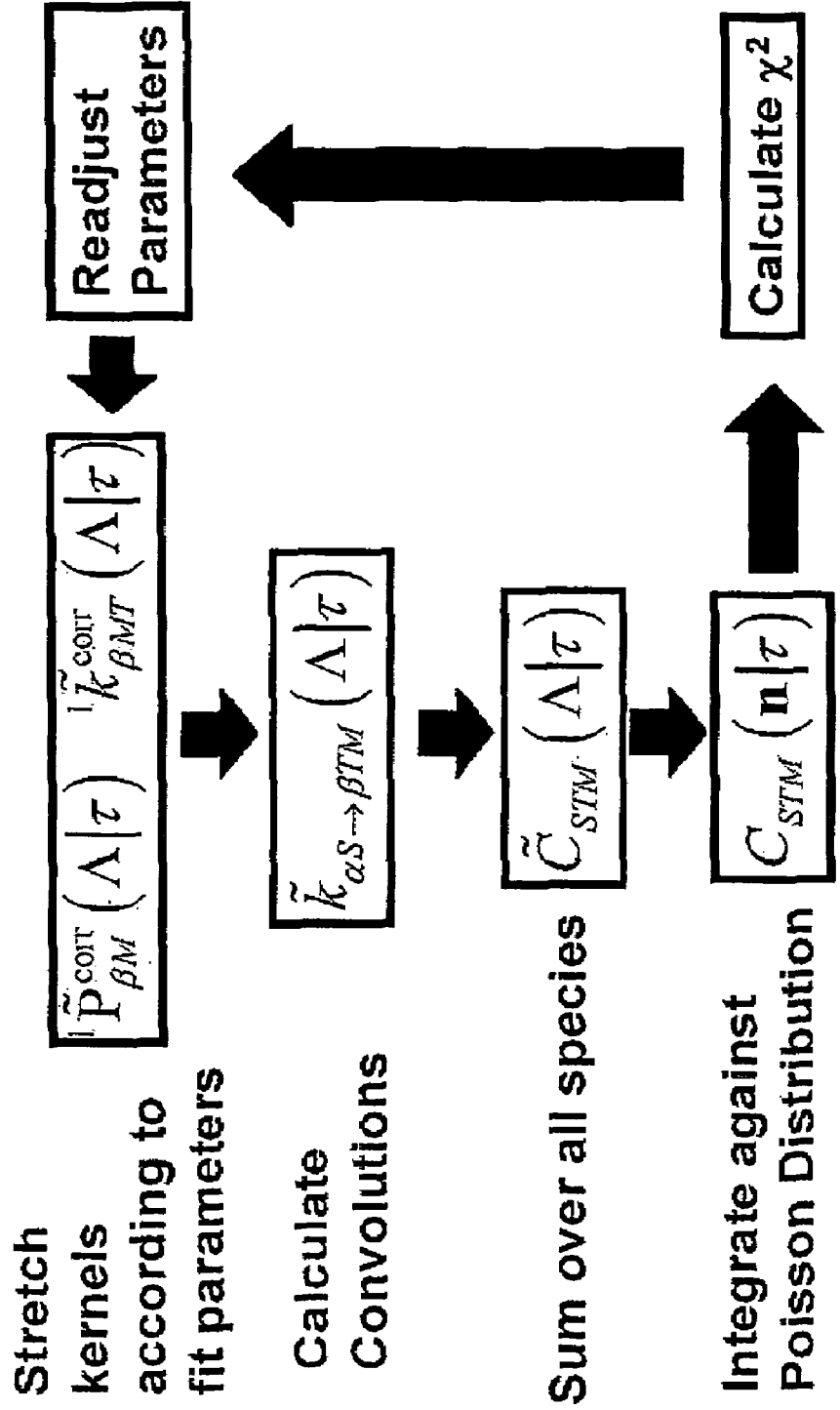
FIG. 13 is an illustration showing flow of PAID model calculation. In the first step, the kernels are stretched using the scaling law in Eqs. (36) and (46). To account for many species the expressions $\tilde{K}_{\alpha S \to \beta TM}(\Lambda|\tau)$ are calculated using Eqs. (73)-(76), where the convolutions are performed using the method in section 2.4.4. Equation (77) is used to sum over all species, and then the final expression is obtained by converting from cumulative intensity space to photon count space (described at end of section 2.4.3). During a model fit, this final expression is compared with the data (for example by calculating $\chi^2$), then the model parameters are adjusted.

The RNAP+DNA sample shows the presence of 4 major species that are also observed after resolution of RNAP+DNA samples on polyacrylamide gels (FIG. 12). For the RNAP-DNA interaction, distinct species can be identified on the basis of their gel mobility and their Y:R emission ratio (note that electrophoretic mobility depends on size and charge, and is not simply related to free translational diffusion measured by PAID). The major species are characterized as i) free DNA; ii) σ-associated species; iii) RNAP-DNA complex; and iv) aggregates (a heterogeneous species with large variety of sizes ranging from smaller oligomers to large aggregates). When a 3-component PAID fit was performed on RNAP+ DNA sample (not shown), a single species with only Y-channel emission was extracted, with brightness corresponding to ~2 copies of TMR per species. This result was inconsistent with the biochemical system (FIG. 12), with visual inspection of the PAID histograms, and with fluorescence-intensity time traces showing few exceptionally bright bursts in the Y channel (such bursts were absent in the buffer or $DNA^{Cy5,65B}$, and were extremely rare in the $R\sigma^{TMR}$ sample). Therefore, a 4-component PAID fit was performed on the RNAP+DNA data, recovering 4 species with diffusion times and Y:R brightness ratios that correspond well to gel-resolved species of RNAP+DNA samples (FIG. 12). This fit yielded additional information inaccessible to ensemble fluorescence imaging or other FFS methods.

Species 1 has properties consistent with those of free $DNA^{Cy5,65B}$ (emission only at the R channel, corresponding to a single copy of Cy5); we identify this species as "free-DNA". Species 2 shows emission only at the Y channel (corresponding to a single copy of TMR), and diffusion time smaller than the RNAP-DNA complex or holoenzyme, but similar to DNA (compared with the 600-700 µs found with Cy3 in previous sections); we identify this species as a combination of a "a-associated species" generated during the preparation of RNAP-DNA complex (Materials and methods), and of RNAP-DNA complex with non-fluorescent Cy5 (analogous to $DNA^{Cydark,1T/Cy3,65B}$ in the previous section). Species 3 shows comparable emission at both Y and R channels (corresponding to a single copy of TMR and a single copy of Cy5), and diffusion time (790 µs) slightly larger than the free holoenzyme (710 µs) and larger than free DNA (440 -480 µs with Cy5 attached, 550 -700 µs with Cy3); we identify this species as "RNAP-DNA complex". Species 4 shows emission only at the Y channel, with high brightness (corresponding to a mean of ~3 copies of TMR per species), and has the longest average diffusion time (850 µs) of all species; we identify this species as "aggregates". Species 4 is a heterogeneous species, likely containing aggregates with varying numbers of subunits; different sections of data contained bursts of highly variable height and duration (most of the bright bursts from species 4 are of ~1 ms duration; however, we have observed "yellow"-labeled species that generated bursts longer that 1 s with a peak height of 60 kHz). This variability is manifested in the PAID fits by the larger uncertainties found for the brightness and diffusion time of species 4. PAID also recovered the occupancy of the various species; however, since PAID measurements are performed in a different concentration regime, matrix, and buffer than the gel mobility assays, quantitative agreement of PAID results with the gel results is not expected. Therefore, this comparison was not performed.

The qualitative agreement between PAID and gel-imaging in terms of molecular size (measured as PAID-based diffusion time or gel-based electrophoretic mobility) and relative brightness (measured as ratio of PAID-based molecular brightness or gel-based fluorescence intensity ratio) of the major species demonstrates the use of PAID for analysis of complex mixtures. Such a complicated mixture will present a great challenge for other popular FFS methods, such as FCS, FCCS, PCH/FIDA, 2 D-FIDA or FIMDA. These methods are not able to simultaneously monitor the diffusion time and brightness on both channels, preventing the reliable detection and characterization of the species obtained using PAID (2 D-FIDA would be able to separate and identify the species, but would lack the information on diffusion time). PAID reliably separates the species by extracting the relative brightness in the two channels; the diffusion time assists in the separation, but also proves very useful in species identification. For example, the diffusion time provides additional evidence for the discrimination between the aggregates and the dimmer, σ -associated species that emit in the same channel.

Fluorescence fluctuation methods are valuable tools for in vitro and in vivo analysis of macromolecular interactions. The most significant advantage of these methods is the ability to detect distinct subpopulations and extract their individual properties. The subpopulations are best identified and characterized by analysis methods that measure several of each species' properties. PAID is a multi-dimensional method that is applicable to multiple channels. The above examples demonstrate that PAID provides robust and simultaneous extraction of occupancy, diffusion time, and brightness in single- and dual-channel formats for multiple species. The examples show that PAID matches or exceeds the statistical accuracy of existing methods.

In single-channel applications, PAID monitors occupancy, diffusion time, and brightness of several species as functions of experimental conditions or time. Monomeric species can be distinguished from oligomeric species by differences in their brightness and diffusion time (FIG. 1A). The examples on DNA model systems demonstrate that brightness measured by fluorescence fluctuation experiments can be used for accurate determination of the number of fluorophores attached to a diffusing species, demonstrating the ability to use brightness in fluorescence fluctuation methods for extracting stoichiometry. Previously, other groups have performed studies that suggest that this is possible, but since no systematic attempts to control stoichiometry or purity were undertaken, their results can not be considered as rigorous tests of the ability of FFS to extract stoichiometry [24, 25]. In contrast, the careful design, construction and purification of the DNA model systems used in the present examples, combined with PAID analysis establishes this capability. The examples also demonstrate that PAID is capable of detecting heterogeneity in brightness, while extracting diffusion times.

Due to background, due to oligomerization-induced species carrying variable numbers of monomers (for example, aggregation induced heterogeneity), and due to other complications (incomplete labeling, quenching of fluorescence, and photobleaching), non-ideal systems contain several species with different brightness. To better characterize such systems, the analysis method should detect heterogeneity in brightness and diffusion time. Correlations between increases in brightness and increases in diffusion time can help verify molecular interactions, providing more evidence than if brightness and diffusion time were determined individually. FCS is not able to detect heterogeneity in brightness, and relies on using diffusion time differences to detect subpopulations. PCH/FIDA detect brightness heterogeneity, but do not account for diffusion (which can differentiate aggregates with quenched fluorescence from monomers without quenched fluorescence). The time bin size must be kept shorter than the diffusion time, preventing full use of the photon data stream. FIMDA has capabilities similar to single-channel PAID. PAID and FIMDA show similar accuracy for most of the simulations, but FIMDA shows lower accuracy for the parameters extracted from simulations in low-occupancy conditions (an experimental comparison has not been performed). On the other hand, FIMDA already accounts for triplet-state fluctuations, whereas these remain to be incorporated into the PAID model. It is possible to use a simultaneous fit of FCS and FIDA/PCH to extract information about brightness and diffusion time simultaneously [31]. However, our fits show that, even if FIDA/PCH fixes the occupancy and brightness of two species to their correct values, FCS is not able to extract the values for the diffusion times as reliably as PAID or FIMDA (Table 2). Using its capabilities, single-channel PAID can be applied to areas such as assembly and stoichiometry of membrane proteins (receptors, ion channels) [71, 72], and amyloid plaque formation [73-75]. FCS has been applied to the characterization of amyloid -peptide polymerization [76, 77]; a fixed concentration (10 nM) of labeled monomer was combined with a varying concentration of unlabeled monomer. The presence of aggregates was detected as large changes in diffusion times. Single-channel PAID allows both brightness and diffusion time to be quantified, providing two observables for the degree of aggregation.

Dual-channel methods provide improved sensitivity over single-channel methods for the analysis of the interactions using fluorescence fluctuation methods [8]. The examples demonstrate PAID-based extraction of coincidence, diffusion time, brightness, and occupancy of several species in a single data set. Control experiments were used to restrict many parameters, increasing confidence in the remaining fitted parameters. The PAID analysis of the RNAP-DNA interaction demonstrates the ability of PAID to analyze complex systems, detecting concentration, brightness and diffusion time for multiple species present in a mixture. This ability allows quantitation of the various free and bound species present in equilibrium binding reactions, thus paving the way for generating binding constants between interacting partners in a high-throughput, low-volume assay format By extending FCCS to PAID, brightness information can be used to discriminate between species and background. In FCCS, leakage and background can hamper extraction of the occupancy of complexes [33]; although control experiments can extract leakage and background, it is often essential to extract all parameters from one data set, requiring control experiments only for checking consistency. PAID simultaneously extracts parameters, and is useful in cases where precise control experiments are impractical or impossible. For example, cellular autofluorescence changes as a function of position, preventing background measurements for a particular spatial position in a cell that contains different fluorescent species. PAID can replace FCCS when it is necessary to extract the brightness of a species in addition to occupancy and diffusion time. FCCS was used to monitor the endocytosis of Cy2- and Cy5-labeled cholera toxin (CTX) into cells [78]. PAID can improve the characterization of the species by determining the brightness in each channel and the number of CTX subunits per vesicle, while analyzing the rare events with long diffusion times and high brightness that caused difficulties in the cross-correlation experiments.

For systems with more than two channels, PAID can be used by picking a series of histograms with channel assignments STM. Previously, single-pair FRET measurements were used to monitor the folded and unfolded subpopulations of the protein Chymotrypsin Inhibitor 2 at different concentrations of denaturant [69]. By splitting the emitted signal by polarization as well as by emission spectrum (into donor and acceptor; 4 channels total), fluorescence anisotropy can be used in conjunction with FRET to obtain more accurate distance measurements [36]. The single-molecule burst identification methods used in these studies can suffer from biases due to unequal detection efficiencies for different channels since the burst searching algorithms preferentially exclude dimmer species. In extracting occupancies, brightness and diffusion time in all four channels, PAID can provide unbiased estimates critical for characterization of protein folding. Moreover, while single-molecule burst-analysis methods are restricted to low-occupancy samples, PAID is applicable to low- and intermediate-occupancy samples, expanding the dynamic range of the analysis of interactions. In addition, with appropriate extensions to the PAID model, conformational dynamics of individual subpopulations on time scales shorter than diffusion may be monitored.

PAID provides a convenient visual representation of important features of diffusing species over a large dynamic range. This is advantageous, since clear visual features in histograms provide the first clues to interesting findings (such as additional subpopulations) or experimental problems. The PAID histogram focuses on photon-rich time intervals, retaining the intuitive nature of correlation functions, while simultaneously providing information available from photon counting histograms. In contrast, the photon counting histograms used in FIDA/PCH and FIMDA weigh all time intervals equally; at low occupancy, most of the bins correspond to time intervals when no molecule is present and few photons are counted. In addition, the log axes used in PAID allow for easy visualization of effects over a large dynamic range.

The model used for the detection volume has a large impact on the accuracy of the method. Using our theoretical model for the detection volume rather than a Gaussian detection volume improved the $\chi^2$ considerably. Similar effects are found in FCS and other FFS methods [68]. Improvement in the quality of PAID fits will come from improved characterization of the detection volume. The FIDA family of methods model the detection volume as a volume density per intensity level; a polynomial expression is used whose parameters are determined using experiments on a standard sample. While attractive for its simplicity, this prevents the modeling of possible trajectories through the detection volume. The model used for PAID is able to account for different possible trajectories through the detection volume.

PAID can impact measurements where simultaneous determination of coincidence and diffusion (or other temporal dynamics) are critical. PAID can be used to monitor protein-protein interactions, such as protein oligomerization. The PAID model can also be extended to include photophysical properties of the dyes (triplet-state induced blinking, singlet and triplet state saturation, photobleaching), and to incorporate an experimentally-measured detection volume; these improvements will increase confidence and might uncover additional dynamics or species not assumed in the fit. The model can be extended to account for two monitor channels, and to become compatible with studies of immobilized molecules and systems involving flow. These extensions of PAID will allow in vitro analysis of dynamics (such as aspects of protein folding), protein-protein interactions and protein-DNA interactions, as well as analysis of interactions in a cellular environment.

"Transit time" for the purposes of this specification includes diffusion time and/or flow time of species within the detection volume. In addition, the term "fluorophore" is intended to cover not only organic fluorescent fluorophores, but also any label or tag, intrinsic or extrinsic, that emits or scatters photons when subjected to light excitation. The PAID method is also useful for measuring temporal dynamics of species within the detection volume.

Having thus described exemplary embodiments of the present invention, it should be noted by those skilled in the art that the within disclosures are exemplary only and that various other alternatives, adaptations and modifications may be made within the scope of the present invention. Accordingly, the present invention is not limited to the above preferred embodiments and examples, but is only limited by the following claims.

REFERENCES

1. Walhout, A. J. M. and M. Vidal, *Protein interaction maps for model Organisms*. Nat. Rev. Mol. Cell. Biol., 2001. 2 (1): p. 55-62.
2. Mendelsohn, A. R. and R. Brent *Protein biochemistry—Protein interaction methods—Toward an endgame*. Science, 1999. 284 (5422): p. 1948-1950.
3. Yanagida, M., *Functional proteomics; current achievements*. J. Chromatogr. B Analyt. Technol. Biomed. Life Sci., 2002. 771 (1-2): p. 89-106.
4. Chalmers, M. J. and S. J. Gaskel, *Advances in mass spectrometry for proteome analysis*. Curr. Opin. Biotechnol., 2000. V 11 (N4): p. 384-390.
5. De Angelis, D. A., *Why FRET over genomics?* Physiol. Genomics, 1999. 1 (2): p. 93-99.
6. Rigler, R. and E. Elson, *Fluorescence correlation spectroscopy: theory and applications*. 2001, Berlin; New York: Springer. xx, 487.
7. Schwille, P., *Fluorescence Correlation Spectroscopy and Its Potential for Intracellular Applications*. Cell Biochemistry and Biophysics, 2001. 34: p. 383-408.
8. Rarbach, M., et al., *Dual-color fluorescence cross-correlation spectroscopy for monitoring the kinetics of enzyme-catalyzed reactions*. Methods, 2001. 24 (2): p. 104-116.
9. Keller, R. A., et al., *Single Molecule Fluorescence Analysis in Solution*. Appl. Spectrosc., 1996. 50 (7): p. A12-A32.
10. Fries, J. R., et al., *Quantitative identification of different single molecules by selective time-resolved confocal fluorescence spectroscopy*. J. Phys. Chem. A., 1998. 102 (33): p. 6601-6613.
11. Dahan, M., et al., *Ratiometric measurement and identification of single diffusing molecules*. Chem. Phys. (Netherlands), 1999. 247 (1): p. 85-106.
12. Deniz, A. A., et al., *Single-pair fluorescence resonance energy transfer on freely diffusing molecules: observation of Förster distance dependence and subpopulations*. Proc. Natl. Acad. Sci. U.S.A., 1999. 96 (7): p. 3670-5.
13. Elson, E. L. and D. Magde, *Fluorescence correlation spectroscopy. I. Conceptual Basis and Theory*. Biopolymers, 1974. 13 (1): p. 1-27.
14. Ehrenberg, M. and R. Rigler, *Rotational Brownian motion and fluorescence intensity fluctuations*. Chem. Phys. (Netherlands), 1974. 4 (3): p. 390-401.
15. Widengren, J., U. Mets, and R. Rigler, *Fluorescence Correlation Spectroscopy of Triplet States in Solution—a Theoretical and Experimental Study*. J. Phys. Chem., 1995. 99 (36): p. 13368-13379.
16. Widengren, J. and R. Rigler, *Mechanisms of photobleaching investigated by fluorescence correlation spectroscopy*. Bioimaging, 1996. 4(3): p. 149-57.
17. Magde, D., E. Elson, and W. W. Webb, *Thermodynamic fluctuations in a reacting system: measurement by fluorescence correlation spectroscopy*. Phys. Rev. Lett., 1972. 29 (11): p. 705-8.

18. Magde, D., E. L. Elson, and W. W. Webb, *Fluorescence correlation spectroscopy. II. An experimental realization*. Biopolymers, 1974. 13 (1): p. 29-61.

19. Doi, M. and S. F. Edwards, *The theory of polymer dynamics*. 1988, Oxford Oxfordshire, N.Y.: Clarendon Press, Oxford University Press. xiii, 391.

20. Qian, H. and E. L. Elson, *On the analysis of high order moments of fluorescence fluctuations*. Biophys. J., 1990. 57 (2): p. 375-80.

21. Qian, H. and E. L. Elson, *Distribution of molecular aggregation by analysis of fluctuation moments*. Proc. Natl. Acad. Sci. U.S.A., 1990. 87 (14): p. 5479-83.

22. Palmer, A. G., III and N. L. Thompson, *Optical spatial intensity profiles for high order autocorrelation in fluorescence spectroscopy*. Appl. Opt., 1989. 28(6): p. 1214-20.

23. Chen, Y., et al., *The photon counting histogram in fluorescence fluctuation spectroscopy*. Biophys. J., 1999. 77 (1): p. 553-67.

24. Kask, P., et al., *Fluorescence-intensity distribution analysis and its application in biomolecular detection technology*. Proc. Natl. Acad. Sci. U.S.A., 1999. 96(24): p. 13756-61.

25. Muller, J. D., Y. Chen, and E. Gratton, *Resolving heterogeneity on the single molecular level with the photon-counting histogram*. Biophys. J., 2000. 78 (1): p. 474-486.

26. Chen, Y., et al., *Probing ligand protein binding equilibria with fluorescence fluctuation spectroscopy*. Biophys. J., 2000. 79 (2): p. 1074-1084.

27. Margeat, E., et al., *The human estrogen receptor alpha dimer binds a single SRC-1 coactivator molecule with an affinity dictated by agonist structure*. J. Mol. Biol., 2001. 306 (3): p. 433-42.

28. Van Rompaey, E., et al., *Fluorescence fluctuation analysis for the study of interactions between oligonucleotides and polycationic polymers*. Biol. Chem., 2001. 382 (3): p. 379-86.

29. Scheel, A. A., et al., *Receptor-ligand interactions studied with homogeneous Fluorescence-based assays suitable for miniaturized screening*. J. Biomol. Screen., 2001. 6(1): p. 11-18.

30. Rudiger, M., et al., *Single-molecule detection technologies in miniaturized high throughput screening: Binding assays for G protein-coupled receptors using fluorescence intensity distribution analysis and fluorescence anisotropy*. Journal of Biomolecular Screening, 2001. V 6 (N1): p. 29-37.

31. Chen, Y., et al., *Molecular brightness characterization of EGFP in vivo by fluorescence fluctuation spectroscopy*. Biophys. J., 2002. 82 (1): p. 133-144.

32. Palo, K., et al., *Fluorescence intensity multiple distributions analysis: concurrent determination of diffusion times and molecular brightness*. Biophys. J., 2000. 79 (6): p. 2858-66.

33. Schwille, P., F. J. Meyer-Almes, and R. Rigler, *Dual-color fluorescence cross-correlation spectroscopy for multicomponent diffusional analysis in solution [see comments]*. Biophys. J., 1997. 72 (4): p. 1878-86.

34. Heinze, K. G., A. Koltemann, and P. Schwille, *Simultaneous two-photon excitation of distinct labels for dual-color fluorescence cross-correlation analysis*. Proc. Natl. Acad. Sci. U.S.A., 2000. 97 (19): p. 10377-82.

35. Schwille, P. and K. G. Heinze, *Two-photon fluorescence cross-correlation Spectroscopy*. Chemphyschem., 2001. 2 (5): p. 269-272.

36. Deniz, A. A., et al., *Ratiometric single-molecule studies of freely diffusing Biomolecules*. Annu. Rev. Phys. Chem., 2001. 52: p. 233-253.

37. Tellinghuisen, J., et al., *Analysis of Fluorescence Lifetime Data for Single Rhodamine Molecules in Flowing Sample Streams*. Anal. Chem., 1994. 66(1): p. 64-72.

38. Eggeling, C., et al., *Monitoring conformational dynamics of a single molecule by selective fluorescence spectroscopy* Proc. Natl. Acad. Sci. U.S.A., 1998. 95 (4): p. 1556-61.

39. Kask P., et al., *Two-dimensional fluorescence intensity distribution analysis: theory and applications*. Biophys. J., 2000. 78 (4): p. 1703-13.

40. Reynaud, S., *Resonance fluorescence: the dressed atom approach*. Ann. Phys., 1983. 8 (4): p. 315-70.

41. Edman, L. and R. Rigler, *Memory landscapes of single-enzyme molecules*. Proc. Natl. Acad. Sci. U.S.A., 2000. 97 (15): p. 8266-71.

42. Schatzel, K., *New concepts in correlator design*. Inst. Phys. Conf. Ser. No. 77: session 4, 1985. No. 77: session 4: p. 175-185.

43. Schatzel, K. and R. Peters, *Noise on Multiple-Tau Photon Correlation Data*. SPIE vol. 1430 Photon Correlation Spectroscopy: Multicomponent Systems, 1991. 1430: p. 109-115.

44. Press, W. H., S. A. Teukolsky, W. T. Vetterling, and B. P. Flannery, *Numerical recipes in C: the art of scientific computing*. 2 nd ed. 1992, Cambridge, U.K.: Cambridge University Press. xxvi, 994.

45. Rigler, R., et al., *Fluorescence Correlation Spectroscopy With High Count Rate and Low Background—Analysis of Translational Diffusion*. Eur. Biophys. J., 1993. 22 (3): p. 169-175.

46. Mets, U., *Antibunching and Rotational Diffusion in FCS*, in *Fluorescence Correlation Spectroscopy*, R. Rigler, and E. S. Elson, Editor. 2001, Springer. p. 346-359.

47. Creighton, T. E., *Proteins: structures and molecular principles*. 1983, New York: W. H. Freeman. xi, 515.

48. Enderlein, J., David L. Robbins, W. Patrick Ambrose, Peter M. Goodwin, and Richard A. Keller, *Statistics of Single-Molecule Detection*. J. Phys. Chem. B, 1997. 101: p. 3626-3632.

49. Maiti, S., U. Haupts, and W. W. Webb, *Fluorescence correlation spectroscopy: diagnostics for sparse molecules*. Proc. Natl. Acad. Sci. U.S.A., 1997. 94 (22): p. 11753-7.

50. Kubo, R. O., M. Toda, and N. Hashitsume, *Statistical physics II: nonequilibrium statistical mechanics*. 2 nd ed. Springer series in solid-state sciences; 31. 1991, Berlin; New York: Springer. 279.

51. Enderlein, J., *Path Integral Approach to Fluorescence Correlation Experiments*. Phys. Lett. A, 1996. 221 (6): p. 427-433.

52. Gardiner, C. W., *Handbook of stochastic methods for physics, chemistry, and the natural sciences*. 2 nd ed. 1985, Berlin; New York: Springer-Verlag. xix, 442.

53. Mandel, L., *Fluctuations of Photon Beams and their Correlation*. Proc. Phys. Soc., 1958. 72: p. 1037-1048.

54. Mandel, L., *Fluctuations of Photon Beams: The Distribution of the Photo-Electrons*. Proc. Phys. Soc., 1959. 74 (3): p. 233-243.

55. Sambrook, J. and D. W. Russell, *Molecular cloning: a laboratory manual*. 3 rd ed. 2001, Cold Spring Harbor, N.Y.: Cold Spring Harbor Laboratory Press. 3 v.

56. Mukhopadhyay, J., et al., *Translocation of sigma (70) with RNA polymerase during transcription: fluorescence resonance energy transfer assay for movement relative to DNA*. Cell, 2001. 106 (4): p. 453-63.

57. Murakami, K. S., et al., *Structural basis of transcription initiation: an RNA polymerase holoenzyme -DNA complex*. Science, 2002. 296 (5571): p. 1285-90.

58. Wohland, T., R. Rigler, and H. Vogel, *The standard deviation in fluorescence correlation spectroscopy*. Biophys. J., 2001. 80 (6): p. 2987-99.

59. Marquardt, D. W., *An algorithm for least-squares estimation of nonlinear Parameters*. J. Soc. Indust. Appl. Math., 1963. 11 (2): p. 431-441.

60. Richards, B. and E. Wolt, *Electromagnetic diffraction in optical systems. II. Structure oft he image field in an aplanatic system*. Proc. Phys. Soc. A, 1959. 253: p. 358-379.

61. Wol, E., *Electromagnetic diffraction in optical systems. I. An integral representation of the image field*. Proc. Phys. Soc. A, 1959. 253: p. 349-357.

62. Cantor, C. R. and P. R. Schimmel, *Biophysical chemistry*. 1980, San Francisco: W. H. Freeman. v. <1>.

63. Lide, D. R., *CRC handbook of chemistry and physics*. 3rd electronic ed ed. 2001, Boca Raton, Fla.: CRC Press.

64. Efron, B. and R. Tibshirani, *An introduction to the bootstrap*. Monographs on statistics and applied probability; 57. 1993, New York: Chapman & Hall. xvi, 436.

65. Eigen, M. and R. Rigler, *Sorting Single Molecules—Application to Diagnostics and Evolutionary Biotechnology*. Proc. Natl. Acad. Sci. U.S.A., 1994. 91 (13): p. 5740-5747.

66. Laurence, T. A., *Photon-counting single -molecule spectroscopy for studying conformational dynamics and macromolecular interactions*, in Physics. 2002, University of California: Berkeley, Calif. p. 182.

67. Widengren, J. and P. Schwille, *Characterization of photoinduced isomerization and back -isomerization of the cyanine dye Cy5 by fluorescence correlation spectroscopy*. J. Phys. Chem. A., 2000. 104 (27): p. 6416-6428.

68. Hess, S. T. and W. W. Webb, *Focal volume optics and experimental artifacts in confocal fluorescence correlation spectroscopy*. Biophys. J., 2002. 83 (4): p. 2300-17.

69. Deniz, A. A., et al., *Single -molecule protein folding: diffusion fluorescence resonance energy transfer studies of the denaturation of chymotrypsin inhibitor 2*. Proc. Natl. Acad. Sci. U.S.A., 2000. 97 (10): p. 5179-84.

70. Dittrich, P. S. and P. Schwille, *Photobleaching and stabilization of fluorophores used for single -molecule analysis with one - and two -photon excitation*. Applied Physics B-Lasers and Optics, 2001. 73 (8): p. 829-837.

71. Hebert, T. E. and M. Bouvier, *Structural and functional aspects of G protein -coupled receptor oligomerization*. Biochem. Cell. Biol., 1998. 76(1): p. 1-11.

72. Milligan, G., *Neurobiology. Receptors as kissing cousins*. Science, 2000. 288(5463): p. 65-7.

73. Bieschke, J., et al., *Ultrasensitive detection of pathological prion protein aggregates by dual -color scanning for intensely fluorescent targets*. Proc. Natl. Acad. Sci. U.S.A., 2000. 97 (10): p. 5468-73.

74. Cohen, F. E., *Protein misfolding and prion diseases*. J. Mol. Biol., 1999. 293(2): p. 313-20.

75. Prusiner, S. B., *Prions*. Proc. Natl. Acad. Sci. U.S.A., 1998. 95 (23): p. 13363-83.

76. Tjernberg, L. O., et al., *Amyloid beta -peptide polymerization studied using fluorescence correlation spectroscopy*. Chem. Biol., 1999. 6(1): p. 53-62.

77. Pitschke, M., et al., *Detection of single amyloid beta -protein aggregates in the cerebrospinal fluid of Alzheimer's patients by fluorescence correlation spectroscopy*. Nat. Med., 1998. 4 (7): p. 832-4.

78. Bacia, K., I. V. Majoul, and P. Schwille, *Probing the endocytic pathway in live cells using dual -color fluorescence cross-correlation analysis*. Biophys. J., 2002. 83 (2): p. 1184-93.

What is claimed is:

1. A method for analyzing properties of one or more species that are labeled with fluorophores, said method comprising the steps of:
    using a detector to detect a plurality of photons that are emitted in a photon stream from a species that is labeled with a fluorophore located in a detection volume wherein each of said photons arrives at said detector at an arrival time;
    determining the arrival time of each of said photons in said plurality of photons;
    identifying the intervals between the arrival time of a given photon and the arrival time of other photons in said plurality of photons to thereby provide photon pair intervals that are a measure of the time between the arrival of each pair of photons in said plurality of photons;
    determining the number of photons that have arrival times that are within said photon pair intervals to provide a measure of intervening photons located within said photon pair intervals; and
    calculating properties of said species that are located in said detection volume based on a relationship between said photon pair intervals and said measure of intervening photons.

2. A method for analyzing properties of one or more species that are labeled with fluorophores according to claim 1 wherein said species that are located in said detection volume comprise a first species labeled with a first fluorophore and a second species labeled with a second fluorophore wherein said first and second species are capable of binding to each other in said detection volume to provide a third species that is labeled with both said first and second fluorophores.

3. A method for analyzing properties of one of more species that are labeled with fluorophores according to claim 1 wherein said properties of said species that are analyzed include brightness, concentration and transit time.

4. A method for analyzing properties of one or more species that are labeled with fluorophores according to claim 2 wherein said properties of said species that are analyzed include brightness, concentration and transit time.

5. A method for analyzing properties of one or more species that are labeled with fluorophores according to claim 1 wherein at least two different plurality of photons are emitted from said detection volume in two different photon streams, said method comprising the steps of:
    determining the arrival time for each of said photons in both of said plurality of photons located in said different photon streams;
    identifying the intervals between the arrival time of a given photon and the arrival time of other photons in each of said plurality of photons to thereby provide photon pair intervals that are a measure of the time between the arrival of each pair of photons in each of said plurality of photons;
    determining the number of photons that have arrival times that are within said photon pair intervals to provide a measure of intervening photons located within said photon pair intervals for each of said plurality of photons; and
    calculating properties of said species that are located in said detection volume based on a relationship between said photon pair intervals and said measure of intervening photons for each of said plurality of photons.

6. A method for analyzing properties of one or more species that are labeled with fluorophores according to claim 5 wherein said species that are located in said detection volume comprise a first species labeled with a first fluorophore and a second species labeled with a second fluorophore wherein said first and second species are capable of binding to each other in said detection volume to provide a third species that is labeled with both said first and second fluorophores.

7. A method for analyzing properties of one or more species that are labeled with fluorophores according to claim 5 wherein said properties of said species that are analyzed include brightness, concentration, coincidence and transit time.

8. A method for analyzing properties of one or more species that are labeled with fluorophores according to claim 6 wherein said properties of said species that are analyzed include brightness, concentration, coincidence and transit time.

9. In a method for analyzing properties of one or more species that are labeled with fluorophores and that are located within a detection volume where a detector is used to detect a plurality of photons that are emitted as part of a photon stream from said species, the improvement comprising:
   determining the time when said photons in said plurality of photons arrive at said detector to provide an arrival time for each of said photons;
   identifying the intervals between the arrival time of a given photon and the arrival time of other photons in said plurality of photons to thereby provide photon pair intervals that are a measure of the time between the arrival of each pair of photons in said plurality of photons;
   determining the number of photons that have arrival times that are within said photon pair intervals to provide a measure of intervening photons located within said photon pair intervals; and
   calculating properties of said one or more species that are located in said detection volume based on a relationship between said photon pair intervals and said measure of intervening photons.

10. An improved method for analyzing properties of one or more species that are labeled with fluorophores according to claim 9 wherein said species that are located in said detection volume comprise a first species labeled with a first fluorophore and a second species labeled with a second fluorophore wherein said first and second species are capable of binding to each other in said detection volume to provide a third species that is labeled with both said first and second fluorophores.

11. An improved method for analyzing properties of one or more species that are labeled with fluorophores according to claim 9 wherein said properties of said species that are analyzed include brightness, concentration and transit time.

12. An improved method for analyzing properties of one or more molecules that are labeled with fluorophores according to claim 10 wherein said properties of said species that are analyzed include brightness, concentration and transit time.

13. An improved method for analyzing properties of one or more species that are labeled with fluorophores according to claim 9 wherein at least two different plurality of photons are emitted as part of two different photon streams from said detection volume, said improvement comprising the steps of:
   determining the arrival time for each of said photons in both of said plurality of photons;
   identifying the intervals between the arrival time of a given photon and the arrival time of other photons in each of said plurality photon to thereby provide photon pair intervals that are a measure of the time between the arrival of each pair of photons in each of said plurality of photons;
   determining the number of photons that have arrival times that are within said photon pair intervals to provide a measure of intervening photons located within said photon pair intervals for each of said plurality of photons; and
   calculating properties of said species that are located in said detection volume based on a relationship between said photon pair intervals and said measure of intervening photons for each of said plurality of photons.

14. An improved method for analyzing properties of one or more species that are labeled with fluorophores according to claim 13 wherein said species that are located in said detection volume comprise a first species labeled with a first fluorophore and a second species labeled with a see end fluorophore wherein said first and second species are capable of binding to each other in said detection volume to provide a third species that is labeled with both said first and second fluorophores.

15. An improved method for analyzing properties of one or more species that are labeled with fluorophores according to claim 13 wherein said properties of said species that are analyzed include brightness, concentration, coincidence and transit time.

16. An improved method for analyzing properties of one or more species that are labeled with fluorophores according to claim 14 wherein said properties of said species that are analyzed include brightness, concentration, coincidence and transit time.

17. A method for analyzing properties of one or more species that are labeled with fluorophores according to claim 1 wherein said step of analyzing said properties comprises forming a histogram having one axis that is a measure of said photon pair intervals and a second axis that is a measure of said intervening photons located within said photon pair intervals.

18. An improved method for analyzing properties of one or more species that are labeled with fluorophores according to claim 9 wherein said step of analyzing said properties comprises forming a histogram having one axis that is a measure of said photon pair intervals and a second axis that is a measure of said intervening photons located within said photon pair intervals.

* * * * *

UNITED STATES PATENT AND TRADEMARK OFFICE
CERTIFICATE OF CORRECTION

PATENT NO. : 7,599,059 B2
APPLICATION NO. : 10/521632
DATED : October 6, 2009
INVENTOR(S) : Laurence et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 608 days.

Signed and Sealed this

Twenty-eighth Day of September, 2010

David J. Kappos
*Director of the United States Patent and Trademark Office*